United States Patent
Chappie et al.

(10) Patent No.: US 10,669,279 B2
(45) Date of Patent: Jun. 2, 2020

(54) IMIDAZOPYRIDAZINE COMPOUNDS

(71) Applicant: Pfizer Inc., New York, NY (US)

(72) Inventors: Thomas Allen Chappie, Carlisle, MA (US); Nandini Chaturbhai Patel, Waban, MA (US); Matthew Merrill Hayward, Old Lyme, CT (US); Christopher John Helal, Mystic, CT (US); Simone Sciabola, Cambridge, MA (US); Erik Alphie LaChapelle, Uncasville, CT (US); Joseph Michael Young, Castro Valley, CA (US); Patrick Robert Verhoest, Newton, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 16/455,020

(22) Filed: Jun. 27, 2019

(65) Prior Publication Data
US 2019/0322674 A1    Oct. 24, 2019

Related U.S. Application Data

(63) Continuation of application No. 16/056,968, filed on Aug. 7, 2018, which is a continuation of application No. 15/426,423, filed on Feb. 7, 2017, now Pat. No. 10,077,269, which is a continuation of application No. 14/817,606, filed on Aug. 4, 2015, now Pat. No. 9,598,421.

(60) Provisional application No. 62/157,129, filed on May 5, 2015, provisional application No. 62/033,684, filed on Aug. 6, 2014.

(51) Int. Cl.
C07D 487/04    (2006.01)
C07D 519/00    (2006.01)

(52) U.S. Cl.
CPC ......... *C07D 487/04* (2013.01); *C07D 519/00* (2013.01)

(58) Field of Classification Search
CPC .................................................. C07D 487/04
See application file for complete search history.

(56) References Cited

U.S. PATENT DOCUMENTS

| | | | |
|---|---|---|---|
| 5,814,651 A | 9/1998 | Duplantier |
| 6,579,882 B2 | 6/2003 | Stewart |
| 6,924,287 B1 | 8/2005 | Janssens |
| 7,544,684 B2 | 6/2009 | Eggenweiler |
| 7,605,168 B2 | 10/2009 | Ibrahim |
| 7,709,518 B2 | 5/2010 | Chen |
| 7,723,323 B2 | 5/2010 | Andersen |
| 7,985,753 B2 | 7/2011 | Danysz |
| 9,120,788 B2 | 9/2015 | Chappie |
| 9,193,736 B2 | 11/2015 | Player |
| 9,598,421 B2 | 3/2017 | Chappie |
| 2003/0064031 A1 | 4/2003 | Humphrey |
| 2003/0064374 A1 | 4/2003 | Ikhlef |
| 2003/0069260 A1 | 4/2003 | Guadilliere |
| 2003/0092706 A1 | 5/2003 | Barsig |
| 2003/0153595 A1 | 8/2003 | Walker |
| 2003/0176450 A1 | 9/2003 | Atkinson |
| 2003/0187257 A1 | 10/2003 | Gaudilliere |
| 2003/0187261 A1 | 10/2003 | Havlicek |
| 2003/0191086 A1 | 10/2003 | Hanus |
| 2004/0087588 A1 | 5/2004 | Beaton |
| 2004/0157933 A1 | 8/2004 | Akiyama |
| 2004/0162314 A1 | 8/2004 | Dube |
| 2004/0176252 A1 | 9/2004 | Eggenweiler |
| 2004/0176419 A1 | 9/2004 | Knowles |
| 2004/0180918 A1 | 9/2004 | Knowles |
| 2004/0235845 A1 | 11/2004 | Eggenweiler |
| 2004/0242597 A1 | 12/2004 | Klein |
| 2004/0254212 A1 | 12/2004 | Denholm |
| 2004/0259863 A1 | 12/2004 | Eggenweiler |
| 2005/0009829 A1 | 1/2005 | Nazare |

(Continued)

FOREIGN PATENT DOCUMENTS

| | | |
|---|---|---|
| CA | 2931026 | 6/2017 |
| EP | 3177624 | 6/2017 |

(Continued)

OTHER PUBLICATIONS

Burgin, et al., "Design of phosphodiesterase 4D (PDE4D) allosteric modulators for enhancing cognition with improved safety", Nature Biotechnology Advance Online Publication, 2010, pp. 63-72, vol. 28.

Deninno Michael P., "Future Directions in Phosphodiesterase Drug Discovery", Bioorganic and Medicinal Chemistry Letters, Nov. 15, 2012, pp. 6794-6800, 22(22).

Donnell, et al., "Identification of pyridazio[4,5-b]indolizines as selective PDE4B Inhibitors", Bioorganic & Medicinal Chemistry Letters, Apr. 1, 2010, pp. 2163-2167, 20(7).

Dorange, et al., "Discovery of novel pyrrolopyridazine scaffolds as transient receptor potential vanilloid ;TRPV1) antagonists", Bioorganic & Medicinal Chemistry Letters, 2012, pp. 6888-6895, vol. 22.

(Continued)

*Primary Examiner* — Paul V Ward
(74) *Attorney, Agent, or Firm* — Haley Guiliano LLP; James F. Haley, Jr.; Brittany J. Barrett

(57) ABSTRACT

The present invention is directed to compounds of Formula I:

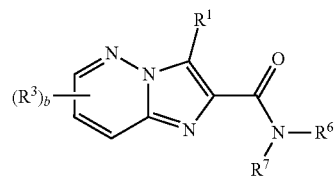

or a pharmaceutically acceptable salt thereof, wherein the substituents $R^1$, $R^3$, $R^6$, $R^7$, and b are as defined herein. The invention is also directed to pharmaceutical compositions comprising the compounds, methods of treatment using the compounds, and methods of preparing the compounds.

22 Claims, No Drawings

(56) References Cited

U.S. PATENT DOCUMENTS

| | | |
|---|---|---|
| 2005/0014762 A1 | 1/2005 | Beume |
| 2005/0020587 A1 | 1/2005 | Bailey |
| 2005/0020593 A1 | 1/2005 | Mailliet |
| 2005/0049255 A1 | 3/2005 | Bictash |
| 2005/0049263 A1 | 3/2005 | Kasibhatla |
| 2005/0070514 A1 | 3/2005 | Rapeport |
| 2005/0070569 A1 | 3/2005 | Guay |
| 2005/0101000 A1 | 5/2005 | Bennett |
| 2005/0137234 A1 | 6/2005 | Bressi |
| 2005/0272803 A1 | 12/2005 | Ruiping |
| 2005/0289660 A2 | 12/2005 | Wang |
| 2006/0025426 A1 | 2/2006 | Fraley |
| 2006/0041006 A1 | 2/2006 | Ibrahim |
| 2006/0148805 A1 | 7/2006 | Chen |
| 2006/0183909 A1 | 8/2006 | Schmitt |
| 2007/0010521 A1 | 1/2007 | Ukita |
| 2007/0191426 A1 | 8/2007 | Edlin |
| 2007/0275984 A1 | 11/2007 | Imogai |
| 2008/0096884 A1 | 4/2008 | Edlin |
| 2008/0096903 A1 | 4/2008 | Chen |
| 2008/0102475 A1 | 5/2008 | Kan |
| 2009/0029938 A1 | 1/2009 | Renzi |
| 2009/0176778 A1 | 7/2009 | Schmit |
| 2009/0275586 A1 | 11/2009 | Govek |
| 2010/0105729 A1 | 4/2010 | Govek |
| 2010/0130737 A1 | 5/2010 | Itoh |
| 2010/0204265 A1 | 8/2010 | Baskaran |
| 2010/0240663 A1 | 9/2010 | Christos |
| 2010/0267714 A1 | 10/2010 | Jorgensen |
| 2011/0003820 A1 | 1/2011 | Henrich |
| 2011/0173726 A1 | 7/2011 | Grab |
| 2011/0275623 A1 | 10/2011 | Baker |
| 2011/0275622 A1 | 11/2011 | Bake |
| 2012/0041045 A1 | 2/2012 | Harvey |
| 2012/0122888 A1 | 5/2012 | Ku |
| 2012/0283274 A1 | 11/2012 | Plitt |
| 2012/0289474 A1 | 11/2012 | Flockerzi |
| 2014/0235612 A1 | 2/2014 | Chappie |
| 2017/0204099 A1 | 7/2017 | Chappie |
| 2018/0346475 A1 | 12/2018 | Chappie |

FOREIGN PATENT DOCUMENTS

| | | |
|---|---|---|
| IN | 55MUM2009 | 9/2010 |
| JP | H08295667 | 11/1996 |
| WO | WO 2000075145 | 12/2000 |
| WO | WO 2001083481 | 11/2001 |
| WO | WO 2003000697 | 1/2003 |
| WO | WO 2003008373 | 1/2003 |
| WO | WO 2003008396 | 1/2003 |
| WO | WO 2003015789 | 2/2003 |
| WO | WO 2003035650 | 5/2003 |
| WO | WO 2004042390 | 5/2004 |
| WO | WO 2004089471 | 10/2004 |
| WO | WO 2006034312 | 3/2006 |
| WO | WO 2006050976 | 5/2006 |
| WO | WO 2006089689 | 8/2006 |
| WO | WO 2007107499 | 9/2007 |
| WO | WO 2008004117 | 1/2008 |
| WO | WO 2008006050 | 1/2008 |
| WO | WO 2008006051 | 1/2008 |
| WO | WO 2008006052 | 1/2008 |
| WO | WO 2008025822 | 3/2008 |
| WO | WO 2008033739 | 3/2008 |
| WO | WO 2008056176 | 5/2008 |
| WO | WO 2009023623 | 2/2009 |
| WO | WO 2009108551 | 9/2009 |
| WO | WO 2010004306 | 1/2010 |
| WO | WO 2010059836 | 5/2010 |
| WO | WO 2011051342 | 5/2011 |
| WO | WO 2011093924 | 8/2011 |
| WO | WO 2011119465 | 9/2011 |
| WO | WO 2013028263 | 2/2013 |
| WO | WO2014128585 | 8/2014 |
| WO | WO2016012896 | 1/2016 |
| WO | WO2016020786 | 2/2016 |

OTHER PUBLICATIONS

English Translation of Japanese Patent Application Publication No. 8-295667, published Nov. 12, 1996.

Fujita, et al., "Downregulation of Brain Phosphodiesterase Type IV Measured with 11C-(R)-Rolipram Position Emission Tomography in Major Depressive Disorder", Biological Psychiatry, Oct. 1, 2012, pp. 548-554, 72(7).

Hess, et al., "Blockade of TNF-a rapidly inhibits pain responses in the central nervous system", Proceedings of the National Academy of Sciences of the United States of American, Mar. 1, 2011, pp. 3731-3736, 108(9).

Jatan, et al., "Efficacy and safety of apremilast, an oral phosphodiesterase 4 inhibitor, in ankylosing spondylitis", Annals of Rheumatic Diseases, September 1, 2013, pp. 1475-1480, 72(9), Abstract Only.

Jatriciu, et al., "Smiles Rearrangement as a Tool for the Preparation of Dihydrodipyridopyrazines", Organic Letter, 2009, pp. 5502-5505, vol. 11.

Jorange, et al., "Discovery of novel pyrrolopyridazine scaffolds as transient receptor potential vanilloid (TRPV1) antagonists", Bioorg. Med. Chem. Letter., 2012, pp. 6888-6895, 22(22).

Kapp, et al., "Efficacy of apremilast in the treatment of moderate to severe psoriasis: a randomized controlled trial", Lancet, Aug. 25-31, 2012, pp. 738-746, 380(9843).

Kim, et al., "Type 4 Cyclic Adenosine Monophosphate Phosphodiesterase as a Therapeutic Target in Chronic Lymphocytic Leukemia", Blood Journal of the American Society of Hematology, Oct. 1, 1998, pp. 2484-2494, 92 7).

Kodimuthali, "Evaluation of Novel 7-(hetero)aryl-substituted Pyrazolo[1,5-a]pyrimidinesas Phosphodiesterase-4 Inhibitors", Letters in Drug Design & Discovery, Jul. 6, 2010, pp. 402-408, 7(6).

Kumar, et al., "(Pd/C-mediated) coupling-iodocyclization-coupling strategy in discovery of novel PDE4 inhibitors: a new synthesis of pyrazolopyrimidines", Medchemcomm, Jan. 1, 2012, pp. 667-672, 3(6).

Kumar, Neal, et al., "Phosphodiesterase 4-targeted treatments for autoimmune diseases", BMC Medicine, 2013, pp. 1-8, 11(96).

Marquette, et al., "ERK and PDE4 cooperate to induce RAF isoform switching in melanoma", Nature Structural Si Molecular Biology, May 2011, pp. 584-591, 18(5).

Millar, et al., "Disrupted in schizophrenia 1 and phosphodiesterase 4B: towards an understanding of 3sychiatric illness", Journal of Physiology, Oct. 2007, pp. 401-405, 584(2).

Naganuma, et al., "Discovery of selective PDE4B inhibitors", Bioorganic & Medicinal Chemistry Letters, Jul. 15, 2009, pp. 3174-3176, 19(12).

PCT International Patent Application No. PCT/IB2015/055232, filed Jul. 10, 2015, International Preliminary Report on Patentability, dated Feb. 2, 2017, 7 pages.

PCT International Patent Application PCT/16015/055597, filed Jul. 23, 2015 International Preliminary Report on Patentability, dated Feb. 16, 2017, 7 pages.

PCT International Search Report and Written Opinion, PCT/162014/058840, filed Feb. 6, 2014, dated Mar. 25, 2014, 13 pages.

PCT International Patent Application No. PCT/IB2014/058840, filed Feb. 6, 2014, International Preliminary Report on Patentability, dated Aug. 25, 2015, 7 pages.

PCT International Patent Application No. PCT/IB2015/055232, filed Jul. 10, 2015, International Search Report and Written Opinion, dated Oct. 13, 2015, 12 pages.

PCT International Patent Application PCT/1B2015/055597, filed Jul. 23, 2015 International Search Report and Written Opinion, dated Oct. 16, 2015, 12 pages.

Ram, et al., "Regioselective synthesis of substituted and fused pyrazolo[1,5-a]pyrimidines as eishmanichides", Chemical Abstracts, Jan. 1, 1995, Database accession No. 1995-537248, XP002745198.

Robichaud, et al., "Deletion of phosphodiesterase 4D in mice shortens a2-adrenoreceptor-mediated anesthesia, a behavioral correlate of emesis", Journal of Clinical Investigation, Oct. 1, 2002, pp. 1045-1052, 110(7).

(56) References Cited

OTHER PUBLICATIONS

Routers, et al., "Effect of the Phosphodiesterase 4 Inhibitor Roflumilast on Glucose Metabolism in Patients with Treatment-Naïve, Newly Diagnosed Type 2 Diabetes Mellitus", Journal of Clinical Endocrinology and Metabolism, Sep. 2012, pp. 1720-1725, vol. 97, Abstract Only.

Sarboxamides: Potent Human Histamine H4 Antagonists, Journal of Medicinal Chemistry, 2005, pp. 8289-8298, vol. 4.

Schafer, et al., "A premilast mechanism of action and application to psoriasis and psoriatic arthritis", 3iochemical Pharmacology, Jun. 15, 2012, pp. 1583-1590, 83(12).

Schett, et al., "premilast: A novel PDE4 inhibitor in the treatment of autoimmune and inflammatory diseases", Therapeutic Advances Museuloskeletal Diseases, Aug. 16, 2010, pp. 271-278, 2(5).

Schmidt, et al., "BDNF and PDE4, but not the GRPR, Regulate Viability of Human Medulloblastoma Cells", Journal of Molecular Neuroscience, Mar. 2010, pp. 303-310, 40(3).

Seeger, et al., "Immunohistochemical localization of PDE10A in the rat brain", Brain Research, Sep. 26, 2003, pp. 113-126, 985(2).

Siuciak, et al., "Antipsychotic profile of rolipram: efficacy in rats and reduced sensitivity in mice deficient in the 3hosphodiesterase-4B (PDE4B) enzyme", Psychopharmacology, Jun. 2007, pp. 415-425, 192(3).

Spina, Review "PDE4 inhibitors: current status", British Journal of Pharmacology, 2008, pp. 308-315, 3(155).

Sun, et al., "Rolipram promotes remyelination possibly via MEK-ERK signal pathway in cuprizone-induced lemyelination mouse", Experimental Neurology, 2012, pp. 304-311, 237(2).

Tehuang, et al., "The synthesis of Daidzein Derivatives", The Journal of National Taiwan Normal University, 1985, pp. 537-545, vol. 30.

Venable, et al., Preparation and Biological Evaluation of Indole, Benzimidazole, and Thienopyrrole Piperazine.

Vollert, et al., "The glucose-lowering effects of the PDE4 roflumilast inhibitors roflumilast and-N-oxide in db/db nice", Diabetologia, Oct. 2012, pp. 2779-2788, 55(10).

Wang, et al., "The phosphodiesterase-4 inhibitor rolipram reverses An-induced cognitive impairment and neuroinflammatory and apoptotie responses in rats", International Journal of Neuropsychopharmacology, Jul. 2012, pp. 749-766, 15(6).

Yutilov, et al., Khimiya Geterotsiklicheskikh Soedinenii, 1975, (10), pp. 1389-1393.

IMIDAZOPYRIDAZINE COMPOUNDS

This application is a continuation of U.S. patent application Ser. No. 16/056,968, filed Aug. 7, 2018 (pending), which is a continuation of U.S. patent application Ser. No. 15/426,423 filed Feb. 7, 2017, now U.S. Pat. No. 10,077,269, which is a continuation of U.S. patent application Ser. No. 14/817,606 filed Aug. 4, 2015, now U.S. Pat. No. 9,598,421, which claims the benefit under 35 U.S.C. 119(e) of U.S. Provisional Patent Application No. 62/033,684, filed on Aug. 6, 2014, and U.S. Provisional Patent Application No. 62/157,129, filed May 5, 2015, the disclosures of all of said applications are hereby incorporated by reference in their entireties.

FIELD OF THE INVENTION

The present invention relates to imidazopyridazine compounds of Formula I, which are inhibitors of PDE4 isozymes, especially with a binding affinity for the PDE4B isoform, and to the use of such compounds in methods for treating central nervous system (CNS), metabolic, autoimmune and inflammatory diseases or disorders.

BACKGROUND OF THE INVENTION

Phosphodiesterases (PDEs) are a class of intracellular enzymes that cleave the phosphodiester bond in second messenger molecules adenosine 3',5'-cyclic monophosphate (cGMP) and guanosine 3',5'-cyclic monophosphate (cGMP). The cyclic nucleotides cAMP and cGMP serve as secondary messengers in various cellular pathways.

cAMP functions as a second messenger regulating many intracellular processes within the body. One example is in the neurons of the central nervous system, where the activation of cAMP-dependent kinases and the subsequent phosphorylation of proteins are involved in acute regulation of synaptic transmission as well as neuronal differentiation and survival. The complexity of cyclic nucleotide signaling is indicated by the molecular diversity of the enzymes involved in the synthesis and degradation of cAMP. There are at least ten families of adenylyl cyclases, and eleven families of phosphodiesterases. Furthermore, different types of neurons are known to express multiple isozymes of each of these classes, and there is good evidence for compartmentalization and specificity of function for different isozymes within a given neuron.

A principal mechanism for regulating cyclic nucleotide signaling is via phosphodiesterase-catalyzed cyclic nucleotide catabolism. The eleven known families of PDEs are encoded by 21 different genes; each gene typically yields multiple splice variants that further contribute to the isozyme diversity. The PDE families are distinguished functionally based on cyclic nucleotide substrate specificity, mechanism(s) of regulation, and sensitivity to inhibitors. Furthermore, PDEs are differentially expressed throughout the organism, including in the central nervous system. As a result of these distinct enzymatic activities and localization, different PDEs' isozymes can serve distinct physiological functions. Furthermore, compounds that can selectively inhibit distinct PDE isozymes may offer particular therapeutic effects, fewer side effects, or both (Deninno, M., Future Directions in Phosphodiesterase Drug Discovery. *Bioorganic and Medicinal Chemistry Letters* 2012, 22, 6794-6800).

The present invention relates to compounds having a binding affinity for the fourth family of PDEs (i.e., PDE4A, PDE4B, PDE4C, and PDE4D), and, in particular, a binding affinity for the PDE4B isoform.

The PDE4 isozymes carry out selective, high-affinity hydrolytic degradation of the second messenger adenosine 3',5'-cyclic monophosphate (cAMP). Beneficial pharmacological effects resulting from that inhibition have been shown in a variety of disease models. A number of PDE4 inhibitors have been discovered in recent years. For example, Roflumilast (Daliresp®), marketed by Forest Pharmaceuticals, Inc., is approved for severe chronic obstructive pulmonary disease (COPD) to decrease the number of flare-ups or prevent exacerbations of COPD symptoms. Apremilast (Otezla®) has been approved by the U.S. Food and Drug Administration for the treatment of adults with active psoriatic arthritis.

While beneficial pharmacological activity of PDE4 inhibitors has been shown, a common side effect of these treatments has been the induction of gastrointestinal symptoms such as nausea, emesis, and diarrhea, which are currently believed to be associated with inhibition of the PDE4D isoform. Attempts have been made to develop compounds with an affinity for the PDE4B isoform over the PDE4D isoform (See: Donnell, A. F. et al., Identification of pyridazino[4,5-b]indolizines as selective PDE4B inhibitors. *Bioorganic & Medicinal Chemistry Letters* 2010, 20, 2163-7; and Naganuma, K. et al., Discovery of selective PDE4B inhibitors. *Bioorganic and Medicinal Chemistry Letters* 2009, 19, 3174-6). However, there remains a need to develop selective PDE4 inhibitors, especially those having an affinity for the PDE4B isoform. In particular, compounds with enhanced binding affinity for the PDE4B isoform over the PDE4D isoform are anticipated to be useful in the treatment of various diseases and disorders of the central nervous system (CNS). The discovery of selected compounds of the present invention addresses this continued need, and provides additional therapies for the treatment of various diseases and disorders of the central nervous system (CNS), as well as metabolic, autoimmune and inflammatory diseases or disorders.

Treatment with the PDE4B inhibitors of the present invention may also lead to a decrease in gastrointestinal side effects (e.g., nausea, emesis and diarrhea) believed to be associated with inhibition of the PDE4D isoform (Robichaud, A. et al., Deletion of Phosphodiesterase 4D in Mice Shortens α2-Adrenoreceptor-Mediated Anesthesia, A Behavioral Correlate of Emesis. *Journal of Clinical Investigation* 2002, 110, 1045-1052).

SUMMARY OF THE INVENTION

The present invention is directed to compounds of Formula I:

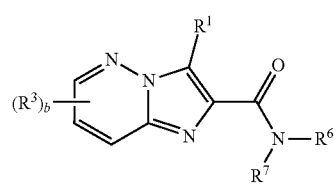

or a pharmaceutically acceptable salt thereof, wherein:
R$^1$ is selected from the group consisting of —(CH$_2$)$_m$—(C$_3$-C$_8$)cycloalkyl, —(CH$_2$)$_m$-(4- to 10-membered)heterocycloalkyl, —(CH$_2$)$_m$—(C$_6$-C$_{10}$)aryl and —(CH$_2$)$_m$-(5- to 14-membered)-heteroaryl, and, where chemically permissible, the $(C_3-C_8)$cycloalkyl, (4- to 10-membered)heterocycloalkyl, $(C_6-C_{10})$aryl and (5- to 14-membered)heteroaryl moieties are optionally substituted with one to five $R^2$;

when present, each $R^2$ is independently selected from the group consisting of halogen, oxo, cyano, hydroxy, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, —$N(R^4)(R^5)$, —$N(R^4)(C(=O)R^5)$, —$C(=O)N(R^4)(R^5)$, —$C(=O)$—$O$—$N(R^4)(R^5)$, —$C(=O)$—$R^4$, —$C(=O)$—$OR^4$, and optionally substituted $(C_3-C_8)$cycloalkyl;

when present, each $R^3$ is independently selected from the group consisting of halogen, cyano, hydroxy, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, —$N(R^4)(R^5)$, —$N(R^4)(C(=O)R^5)$, —$C(=O)N(R^4)(R^5)$, —$C(=O)$—$O$—$N(R^4)(R^5)$, —$C(=O)$—$R^4$, and —$C(=O)$—$OR^4$;

$R^4$ and $R^5$ are each independently selected from the group consisting of hydrogen and optionally substituted $(C_1-C_6)$alkyl;

$R^6$ and $R^7$ are each independently selected from the group consisting of hydrogen, optionally substituted $(C_1-C_6)$alkyl, —$(CH_2)_n$—$(C_3-C_8)$cycloalkyl, —$(CH_2)_n$-(4- to 10-membered) heterocycloalkyl, —$(CH_2)_n$—$(C_6-C_{10})$aryl, and —$(CH_2)_n$-(5- to 10-membered)heteroaryl, and where chemically permissible, the $(C_3-C_8)$cycloalkyl, (4- to 10-membered)heterocycloalkyl, $(C_6-C_{10})$aryl, and (5- to 10-membered)heteroaryl are optionally substituted with one to five $R^8$; or $R^6$ and $R^7$ taken together with the nitrogen to which they are attached form a (4- to 10-membered)heterocycloalkyl, and where chemically permissible, the (4- to 10-membered)-heterocycloalkyl is optionally substituted with one to five $R^9$;

when present, each $R^8$ is independently selected from the group consisting of halogen, oxo, cyano, hydroxy, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, —$N(R^4)(R^5)$, —$N(R^4)(C(=O)R^5)$, —$C(=O)N(R^4)(R^5)$, —$C(=O)$—$O$—$N(R^4)(R^5)$, —$C(=O)$—$R^4$, and —$C(=O)$—$OR^4$;

when present, each $R^9$ is independently selected from the group consisting of halogen, oxo, cyano, hydroxy, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, —$N(R^4)(R^5)$, —$N(R^4)(C(=O)R^5)$, —$C(=O)N(R^4)(R^5)$, —$C(=O)$—$O$—$N(R^4)(R^5)$, —$C(=O)$—$R^4$, and —$C(=O)$—$OR^4$;

b is represented by an integer selected from 0, 1, 2, or 3; m is represented by an integer selected from 0, 1, or 2; and n is represented by an integer selected from 0, 1, 2, 3 or 4.

Compounds of the invention include Examples 1-104 or a pharmaceutically acceptable salt thereof as described herein.

The compounds of Formula I are inhibitors of the PDE4B isoform.

The compounds of Formula I are useful for treating or preventing diseases and/or disorders of the central nervous system (CNS), pain, trauma, cardiologic, thrombotic, metabolic, autoimmune and inflammatory diseases or disorders, and disorders associated with enhanced endothelial activity/impaired endothelial barrier function.

The present invention is also directed to the use of the compounds described herein, or a pharmaceutically acceptable salt thereof, in the preparation of a medicament for the treatment or prevention of a condition amenable to modulation of the PDE4B gene family (i.e., PDE4B enzymes).

The present invention is also directed to pharmaceutically acceptable formulations containing an admixture of a compound(s) of the present invention and at least one excipient formulated into a pharmaceutical dosage form. Examples of such dosage forms include tablets, capsules, suppositories, gels, creams, ointments, lotions, solutions/suspensions for injection (e.g., depot), aerosols for inhalation and solutions/suspensions for oral ingestion.

DETAILED DESCRIPTION OF THE INVENTION

The headings within this document are being utilized only to expedite its review by the reader. They should not be construed as limiting the invention or claims in any manner.

Definitions and Exemplifications

As used throughout this application, including the claims, the following terms have the meanings defined below, unless specifically indicated otherwise. The plural and singular should be treated as interchangeable, other than the indication of number:

As used herein, the term "n-membered" where n is an integer typically describes the number of ring-forming atoms in a moiety where the number of ring-forming atoms is n. For example, pyridine is an example of a 6-membered heteroaryl ring and thiazole is an example of a 5-membered heteroaryl group.

At various places in the present specification, substituents of compounds of the invention are disclosed in groups or in ranges. It is specifically intended that the invention include each and every individual subcombination of the members of such groups and ranges. For example, the term "$(C_1-C_6)$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. For another example, the term "a (5- to 10-membered) heterocycloalkyl group" is specifically intended to include any 5-, 6-, 7-, 8-, 9-, and 10-membered heterocycloalkyl group.

The term "$(C_1-C_6)$alkyl", as used herein, refers to a saturated, branched- or straight-chain alkyl group containing from 1 to 6 carbon atoms, such as, but not limited to, methyl, ethyl, n-propyl, isopropyl, n-butyl, sec-butyl, isobutyl, tert-butyl, n-pentyl, isopentyl, neopentyl, and n-hexyl.

The term "optionally substituted $(C_1-C_6)$alkyl", as used herein, refers to a $(C_1-C_6)$alkyl as defined above, in which one or more hydrogen atoms are replaced by a substituent selected from the group consisting of halogen, oxo, cyano, hydroxy, —$SF_5$, nitro, —$N(R^4)(R^5)$, —$N(R^4)(C(=O)R^5)$, —$N(R^4)C(=O)$—$OR^5$, —$C(=O)$—$N(R^4)(R^5)$, —$C(=O)$—$O$—$N(R^4)(R^5)$, —$C(=O)$—$R^4$, —$C(=O)$—$OR^4$, and $(C_3-C_8)$cycloalkyl, in which $R^4$ and $R^5$ are each independently hydrogen or optionally substituted $(C_1-C_6)$ alkyl. For example, a $(C_1-C_6)$alkyl moiety can be substituted with one or more halogen atoms to form a "halo$(C_1-C_6)$ alkyl". Representative examples of a halo$(C_1-C_6)$alkyl include, but are not limited to, fluoromethyl, difluoromethyl, 2-fluoroethyl, trifluoromethyl, pentafluoroethyl, and 2-chloro-3-fluoropentyl.

The term "$(C_2-C_6)$alkenyl" refers to an aliphatic hydrocarbon having from 2 to 6 carbon atoms and having at least one carbon-carbon double bond, including straight chain or branched chain groups having at least one carbon-carbon double bond.

Representative examples include, but are not limited to, ethenyl, 1-propenyl, 2-propenyl (allyl), isopropenyl, 2-methyl-1-propenyl, 1-butenyl, 2-butenyl, and the like. When the compounds of the invention contain a $(C_2-C_6)$ alkenyl group, the compound may exist as the pure E (entgegen) form, the pure Z (zusammen) form, or any mixture thereof.

The term "optionally substituted $(C_2-C_6)$alkenyl" refers to a $(C_2-C_6)$alkenyl as defined above, in which one or more hydrogen atoms are replaced by a substituent selected from the group consisting of halogen, oxo, cyano, hydroxy, —$SF_5$, nitro, —$N(R^4)(R^5)$, —$N(R^4)(C(=O)R^5)$, —$N(R^4)C(=O)$—$OR^5$, —$C(=O)$—$N(R^4)(R^5)$, —$C(=O)$—O—N$(R^4)(R^5)$, —$C(=O)$—$R^4$, —$C(=O)$—$OR^4$, and $(C_3-C_8)$ cycloalkyl, in which $R^4$ and $R^5$ are each independently hydrogen or optionally substituted $(C_1-C_6)$alkyl.

The term "$(C_2-C_6)$alkynyl" refers to an aliphatic hydrocarbon having two to six carbon atoms and at least one carbon-carbon triple bond, including straight chains and branched chains having at least one carbon-carbon triple bond. Representative examples include, but are not limited to, ethynyl, propynyl, butynyl, pentynyl, and hexynyl.

The term "optionally substituted $(C_2-C_6)$alkynyl" refers to a $(C_2-C_6)$alkynyl as defined above, in which one or more hydrogen atoms are replaced by a substituent selected from the group consisting of halogen, oxo, cyano, hydroxy, —$SF_5$, —$N(R^4)(R^5)$, —$N(R^4)(C(=O)R^5)$, —$N(R^4)C(=O)$—$OR^5$, —$C(=O)$—$N(R^4)(R^5)$, —$C(=O)$—O—N$(R^4)(R^5)$, —$C(=O)$—$R^4$, —$C(=O)$—$OR^4$, and $(C_3-C_8)$ cycloalkyl, in which $R^4$ and $R^5$ are each independently hydrogen or optionally substituted $(C_1-C_6)$alkyl.

The term "$(C_1-C_6)$alkoxy" as used herein, refers to a $(C_1-C_6)$alkyl group, as defined above, attached to the parent molecular moiety through an oxygen atom. Representative examples of a $(C_1-C_6)$alkoxy include, but are not limited to, methoxy, ethoxy, propoxy, 2-propoxy, butoxy, tert-butoxy, pentyloxy, and hexyloxy.

The term "optionally substituted $(C_1-C_6)$alkoxy" as used herein, refers to a $(C_1-C_6)$alkoxy group, as defined above, in which one or more hydrogen atoms are replaced by a substituent selected from the group consisting of halogen, oxo, cyano, hydroxy, —$SF_5$, nitro, —$N(R^4)(R^5)$, —$N(R^4)(C(=O)R^5)$, —$N(R^4)C(=O)$—$OR^5$, —$C(=O)$—$N(R^4)(R^5)$, —$C(=O)$—O—N$(R^4)(R^5)$, —$C(=O)$—$R^4$, —$C(=O)$—$OR^4$, and $(C_3-C_8)$cycloalkyl, in which $R^4$ and $R^5$ are each independently hydrogen or optionally substituted $(C_1-C_6)$alkyl. For example, a $(C_1-C_6)$alkoxy can be substituted with one or more halogen atoms to form a "halo$(C_1-C_6)$alkoxy". Representative examples of a halo $(C_1-C_6)$alkoxy include, but are not limited to, fluoromethoxy, difluoromethoxy, 2-fluoroethoxy, trifluoromethoxy, and pentafluoroethoxy.

The term "$(C_1-C_6)$alkythio", as used herein, refers to a $(C_1-C_6)$alkyl group, as defined above, attached to the parent molecular moiety through a sulfur atom. Representative examples of a $(C_1-C_6)$alkylthio include, but are not limited to, methylthio, ethylthio, propylthio, and the like.

The term "optionally substituted $(C_1-C_6)$alkythio", as used herein, refers to a $(C_1-C_6)$alkylthio group, as defined above, in which one or more hydrogen atoms are replaced by a substituent selected from the group consisting of halogen, oxo, cyano, hydroxy, —$SF_5$, nitro, —$N(R^4)(R^5)$, —$N(R^4)$$(C(=O)R^5)$, —$N(R^4)C(=O)$—$OR^5$, —$C(=O)$—$N(R^4)(R^5)$, —$C(=O)$—O—$N(R^4)(R^5)$, —$C(=O)$—$R^4$, —$C(=O)$—$OR^4$, and $(C_3-C_8)$cycloalkyl, in which $R^4$ and $R^5$ are each independently hydrogen or optionally substituted $(C_1-C_6)$alkyl.

As used herein, the term "$(C_3-C_8)$cycloalkyl" refers to a carbocyclic substituent obtained by removing hydrogen from a saturated carbocyclic molecule wherein the cyclic framework has 3 to 8 carbons. A "$(C_3-C_6)$cycloalkyl" refers to a carbocyclic substituent obtained by removing hydrogen from a saturated carbocyclic molecule having from 3 to 6 carbon atoms. A "cycloalkyl" may be a monocyclic ring, examples of which include cyclopropyl, cyclobutyl, cyclopentyl, cyclohexyl, cycloheptyl, and cyclooctyl. Also included in the definition of cycloalkyl are unsaturated non-aromatic cycloalkyls such as, but not limited to, cyclohexenyl, cyclohexadienyl, cyclopentenyl, cycloheptenyl, and cyclooctenyl. Alternatively, a cycloalkyl may contain more than one ring such as a "$(C_4-C_8)$bicycloalkyl". The term "$(C_4-C_8)$bicycloalkyl" refers to a bicyclic ring system containing from 4 to 8 carbon atoms. The bicycloalkyl may be fused, such as bicyclo[1.1.0]butanyl, bicyclo[2.1.0]pentanyl, bicyclo[2.2.0]hexanyl, bicyclo[3.1.0]hexanyl, bicyclo[3.2.0]heptanyl, and bicyclo[3.3.0]-octanyl. The term "bicycloalkyl" also includes bridged bicycloalkyl systems such as, but not limited to, bicyclo[2.2.1]heptanyl and bicyclo[1.1.1]pentanyl.

The term "optionally substituted "$(C_3-C_8)$cycloalkyl" refers to a $(C_3-C_8)$cycloalkyl, as defined above, in which one or more hydrogen atoms are replaced by a substituent selected from the group consisting of halogen, oxo, cyano, hydroxy, —$SF_5$, nitro, —$N(R^4)(R^5)$, —$N(R^4)(C(=O)R^5)$, —$N(R^4)C(=O)$—$OR^5$, —$C(=O)$—$N(R^4)(R^5)$, —$C(=O)$—O—$N(R^4)(R^5)$, —$C(=O)$—$R^4$, —$C(=O)$—$OR^4$, and $(C_3-C_8)$cycloalkyl, in which $R^4$ and $R^5$ are each independently hydrogen or optionally substituted $(C_1-C_6)$ alkyl.

A "heterocycloalkyl," as used herein, refers to a cycloalkyl as defined above, wherein at least one of the ring carbon atoms is replaced with a heteroatom selected from nitrogen, oxygen or sulfur. The term "(4- to 6-membered) heterocycloalkyl" means the heterocycloalkyl substituent contains a total of 4 to 6 ring atoms, at least one of which is a heteroatom. The term "(4- to 8-membered)heterocycloalkyl" means the heterocycloalkyl substituent contains a total of 4 to 8 ring atoms, at least one of which is a heteroatom. A "(4- to 10-membered)heterocycloalkyl" means the heterocycloalkyl substituent contains a total of 4 to 10 ring atoms. A "(6-membered)heterocycloalkyl" means the heterocycloalkyl substituent contains a total of 6 ring atoms, at least one of which is a heteroatom. A "(5-membered)heterocycloalkyl" means the heterocycloalkyl substituent contains a total of 5 ring atoms at least one of which is a heteroatom. A heterocycloalkyl may be a single ring with up to 10 total members. Alternatively, a heterocycloalkyl as defined above may comprise 2 or 3 rings fused together, wherein at least one such ring contains a heteroatom as a ring atom (i.e., nitrogen, oxygen, or sulfur). The heterocycloalkyl substituent may be attached to the imidazopyridazine core of the compounds of the present invention via a nitrogen atom having the appropriate valence, or via any ring carbon atom. The heterocycloalkyl substituent may also be attached to the nitrogen of the amide moiety on the imidazopyridazine core. The heterocycloalkyl moiety may be optionally substituted with one or more substituents at a nitrogen atom having the appropriate valence, or at any available carbon atom.

Also included in the definition of "heterocycloalkyl" are heterocycloalkyls that are fused to a phenyl or naphthyl ring or to a heteroaryl ring such as, but not limited to, a pyridinyl ring or a pyrimidinyl ring.

Examples of heterocycloalkyl rings include, but are not limited to, azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, octahydrobenzofuranyl, octahydrobenzim idazolyl, octahydrobenzothiazolyl, imidazolidinyl, pyrrolidinyl, piperidinyl, piperazinyl, oxazolidinyl, thiazolidinyl, pyrazolidinyl, thiomorpholinyl, tetrahydropyranyl, tetrahydrothiazinyl, tetrahydrothiadiazinyl, tetrahydro-oxazolyl, morpholinyl, oxetanyl, tetrahydrodiazinyl, oxazinyl, oxathiazinyl, quinuclidinyl, chromanyl, isochromanyl, dihydrobenzodioxinyl, benzodioxolyl, benzoxazinyl, indolinyl, dihydrobenzofuranyl, tetrahydroquinolyl, isochromyl, dihydro-1H-isoindolyl, 2-azabicyclo[2.2.1]heptanonyl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), and the like.

The term "optionally substituted heterocycloalkyl" [e.g., optionally substituted (4- to 10-membered)heterocycloalkyl] refers to a heterocycloalkyl, as defined above, in which one or more hydrogen atoms, where chemically permissible, are replaced by a substituent selected from the group consisting of halogen, oxo, cyano, hydroxy, —$SF_5$, nitro, —$N(R^4)(R^5)$, —$N(R^4)(C(=O)R^5)$, —$N(R^4)C(=O)$—$OR^5$, —$C(=O)$—$N(R^4)(R^5)$, —$C(=O)$—$O$—$N(R^4)(R^5)$, —$C(=O)$—$R^4$, —$C(=O)$—$OR^4$, and $(C_3-C_8)$cycloalkyl, in which $R^4$ and $R^5$ are each independently hydrogen or optionally substituted $(C_1-C_6)$alkyl.

A "$(C_6-C_{10})$aryl" refers to an all-carbon monocyclic or fused-ring polycyclic aromatic group having a conjugated pi-electron system containing from 6 to 10 carbon atoms, such as phenyl or naphthyl.

The term "optionally substituted $(C_6-C_{10})$aryl" refers to a $(C_6-C_{10})$aryl, as defined above, in which one or more hydrogen atoms are replaced by a substituent selected from the group consisting of halogen, cyano, hydroxy, —$SF_5$, nitro, —$N(R^4)(R^5)$, —$N(R^4)(C(=O)R^5)$, —$N(R^4)C(=O)$—$OR^5$, —$C(=O)$—$N(R^4)(R^5)$, —$C(=O)$—$O$—$N(R^4)(R^5)$, —$C(=O)$—$R^4$, —$C(=O)$—$OR^4$, and $(C_3-C_8)$cycloalkyl, in which $R^4$ and $R^5$ are each independently hydrogen or optionally substituted $(C_1-C_6)$alkyl.

As used herein, the term "heteroaryl" refers to monocyclic or fused-ring polycyclic aromatic heterocyclic groups with one or more heteroatom ring members (ring-forming atoms) each independently selected from oxygen (O), sulfur (S) and nitrogen (N) in at least one ring. A "(5- to 14-membered) heteroaryl" ring refers to a heteroaryl ring having from 5 to 14 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 10-membered)heteroaryl" ring refers to a heteroaryl ring having from 5 to 10 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 10-membered)nitrogen-containing heteroaryl" ring refers to a heteroaryl ring having from 5 to 10 ring atoms in which at least one of the ring atoms is nitrogen, with the remaining ring atoms being independently selected from the group consisting of carbon and nitrogen. A "(5- to 6-membered)heteroaryl" refers to a heteroaryl ring having from 5 to 6 ring atoms in which at least one of the ring atoms is a heteroatom (i.e., oxygen, nitrogen, or sulfur), with the remaining ring atoms being independently selected from the group consisting of carbon, oxygen, nitrogen, and sulfur. A "(5- to 6-membered)nitrogen-containing heteroaryl" refers to a heteroaryl ring having from 5 to 6 ring atoms in which all of the heteroatoms in the ring are nitrogen. A "(6-membered)nitrogen-containing heteroaryl" refers to a heteroaryl ring having 6 ring atoms in which all of the heteroatoms in the ring are nitrogen. A "(5-membered) nitrogen-containing heteroaryl" refers to a heteroaryl ring having 5 ring atoms in which all of the heteroatoms in the ring are nitrogen. A heteroaryl may be a single ring or 2 or 3 fused rings. Examples of heteroaryls include, but are not limited to, 6-membered ring substituents such as pyridinyl, pyrazinyl, pyrimidinyl and pyridazinyl; 5-membered heteroaryls such as triazolyl, imidazolyl, furanyl, isoxazolyl, isothiazolyl, 1,2,3-, 1,2,4, 1,2,5-, or 1,3,4-oxadiazolyl, oxazolyl, thiophenyl, thiazolyl, isothiazolyl, and pyrazolyl; 6/5-membered fused ring substituents such as indolyl, indazolyl, benzofuranyl, benzimidazolyl, benzothienyl, benzoxadiazolyl, benzothiazolyl, isobenzothiofuranyl, benzothiofuranyl, benzisoxazolyl, benzoxazolyl, benzodioxolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl (e.g., 5,6,7,8-tetrahydro[1,2,4]triazolo[1,5-a]pyridin-2-yl), and anthranilyl; and 6/6-membered fused ring substituents such as quinolinyl, isoquinolinyl, cinnolinyl, quinazolinyl, oxochromanyl, and 1,4-benzoxazinyl.

It is to be understood that the heteroaryl may be optionally fused to a cycloalkyl group, or to a heterocycloalkyl group, as defined herein.

The heteroaryl substituent may be attached to the imidazopyridazine core of the compounds of the present invention via a nitrogen atom having the appropriate valence, or via any ring carbon atom or to the nitrogen of the amide moiety on the imidazopyridazine core. The heteroaryl moiety may be optionally substituted with one or more substituents at a nitrogen atom having the appropriate valence, or at any available carbon atom.

The terms "optionally substituted (5- to 14-membered) heteroaryl", "optionally substituted (5- to 6-membered)heteroaryl" and "optionally substituted (5- to 6-membered) nitrogen-containing heteroaryl" refer to a (5- to 14-membered)heteroaryl, a (5- to 6-membered)heteroaryl, and a (5- to 6-membered)nitrogen-containing heteroaryl, as defined above, in which one or more hydrogen atoms are replaced, where chemically permissible, by a substituent selected from the group consisting of halogen, oxo, cyano, hydroxy, —$SF_5$, nitro, —$N(R^4)(R^5)$, —$N(R^4)(C(=O)R^5)$, —$N(R^4)C(=O)$—$OR^5$, —$C(=O)$—$N(R^4)(R^5)$, —$C(=O)$—$O$—$N(R^4)(R^5)$, —$C(=O)$—$R^4$, —$C(=O)$—$OR^4$, and $(C_3-C_8)$cycloalkyl, in which $R^4$ and $R^5$ are each independently hydrogen or optionally substituted $(C_1-C_6)$alkyl. The substituent can be attached to the heteroaryl moiety at any available carbon atom or to a heteroatom when the heteroatom is nitrogen having the appropriate valence.

"halo" or "halogen", as used herein, refers to a chlorine, fluorine, bromine, or iodine atom.

"hydroxy" or "hydroxyl", as used herein, means an —OH group.

"cyano", as used herein, means a —CN group, which also may be depicted:

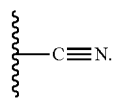

"nitro", as used herein, means an —NO$_2$ group.

"oxo", as used herein, means a =O moiety. When an oxo is substituted on a carbon atom, they together form a carbonyl moiety [—C(=O)—]. When an oxo is substituted on a sulfur atom, they together form a sulfoxide moiety [—S(=O)—]; when two oxo groups are substituted on a sulfur atom, they together form a sulfonyl moiety [—S(=O)$_2$—].

"Optionally substituted", as used herein, means that substitution is optional and therefore includes both unsubstituted and substituted atoms and moieties. A "substituted" atom or moiety indicates that any hydrogen on the designated atom or moiety can be replaced with a selection from the indicated substituent group (up to and including that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., —CH$_3$) is optionally substituted, then up to 3 hydrogen atoms on the carbon atom can be replaced with substituent groups.

As used herein, unless specified, the point of attachment of a substituent can be from any suitable position of the substituent. For example, pyridinyl (or pyridyl) can be 2-pyridinyl (or pyridin-2-yl), 3-pyridinyl (or pyridin-3-yl), or 4-pyridinyl (or pyridin-4-yl).

When a bond to a substituent is shown to cross a bond connecting two atoms in a ring, then such substituent may be bonded to any of the ring-forming atoms in that ring that are substitutable (i.e., bonded to one or more hydrogen atoms). For example, as shown in Formula I above, R$^3$ may be bonded to any ring-forming atom of the pyridazine ring that is substitutable.

"Therapeutically effective amount" refers to that amount of the compound being administered which will relieve to some extent one or more of the symptoms of the disorder being treated.

"Patient" refers to warm-blooded animals such as, for example, pigs, cows, chickens, horses, guinea pigs, mice, rats, gerbils, cats, rabbits, dogs, monkeys, chimpanzees, and humans.

"Treating" or "treat", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject.

"Pharmaceutically acceptable" indicates that the substance or composition must be compatible, chemically and/or toxicologically, with the other ingredients comprising a formulation, and/or the mammal being treated therewith.

"Isoform" means any of several different forms of the same protein.

"Isozyme" or "isoenzyme" means a closely related variant of an enzyme that differs in amino acid sequence but catalyzes the same chemical reaction.

"Isomer" means "stereoisomer" and "geometric isomer" as defined below.

"Stereoisomer" refers to compounds that possess one or more chiral centers, which may each exist in the R or S configuration. Stereoisomers include all diastereomeric, enantiomeric and epimeric forms as well as racemates and mixtures thereof.

"Geometric isomer" refers to compounds that may exist in cis, trans, anti, entgegen (E), and zusammen (Z) forms as well as mixtures thereof.

This specification uses the terms "substituent," "radical," and "group" interchangeably.

If substituents are described as being "independently selected" from a group, each instance of a substituent is selected independent of any other. Each substituent therefore may be identical to or different from the other substituent(s).

As used herein the term "Formula I" may be hereinafter referred to as a "compound(s) of the invention." Such terms are also defined to include all forms of the compound of the invention including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

Some of the compounds of the invention have asymmetric carbon atoms. The carbon-carbon bonds of the compounds of the invention may be depicted herein using a solid line (———), a solid wedge (◢◣), or a dotted wedge (·······). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that the stereoisomer shown is present. When present in racemic compounds, solid and dotted wedges are used to define relative stereochemistry, rather than absolute stereochemistry. Racemic compounds possessing such indicated relative stereochemistry are marked with (+/−). Unless stated otherwise, it is intended that the compounds of the invention can exist as stereoisomers, which include cis and trans isomers, optical isomers such as R and S enantiomers, diastereomers, geometric isomers, rotational isomers, conformational isomers, atropisomers, and mixtures thereof (such as racemates and diastereomeric pairs). The compounds of the invention may exhibit more than one type of isomerism. Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of the present invention with an acid whose anion, or a base whose cation, is generally considered suitable for mammalian consumption. Pharmaceutically acceptable salts are particularly useful as products of the methods of the present invention because of their greater aqueous solubility relative to the parent compound.

Suitable pharmaceutically acceptable acid addition salts of the compounds of the present invention when possible include those derived from inorganic acids, such as, but not limited to, hydrochloric, hydrobromic, hydrofluoric, boric, fluoroboric, phosphoric, meta-phosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include but are not limited to aliphatic, cycloaliphatic, aromatic, araliphatic, heterocyclic, carboxylic, and sulfonic classes of organic acids.

Specific examples of suitable organic acids include but are not limited to acetate, trifluoroacetate, formate, propionate, succinate, glycolate, gluconate, digluconate, lactate, malate, tartrate, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethansulfonate, sufanilate, cyclohexylamino-ethansulfonate, algenic acid, 3-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalene-sulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Certain compounds of the invention may exist as geometric isomers. The compounds of the invention may possess one or more asymmetric centers, thus existing as two, or more, stereoisomeric forms. The present invention includes all the individual stereoisomers and geometric isomers of the compounds of the invention and mixtures thereof. Individual enantiomers can be obtained by chiral separation or using the relevant enantiomer in the synthesis.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention. The compounds may also exist in one or more crystalline states, i.e., polymorphs, or they may exist as amorphous solids. All such forms are encompassed by the claims.

Also within the scope of the present invention are so-called "prodrugs" of the compound of the invention. Thus, certain derivatives of the compound of the invention that may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and W. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of the present invention with certain moieties known to those skilled in the art as "pro-moieties" as described, for example, in "Design of Prodrugs" by H. Bundgaard (Elsevier, 1985).

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The present invention also includes all pharmaceutically acceptable isotopically labeled compounds, which are identical to those recited herein, wherein one or more atoms are replaced by an atom having the same atomic number, but an atomic mass or mass number different from the atomic mass or mass number which predominates in nature. Examples of isotopes suitable for inclusion in the compounds of the present invention include, but are not limited to, isotopes of hydrogen, such as $^2$H, $^3$H; carbon, such as $^{11}$C, $^{13}$C, and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O, and $^{18}$O; phosphorus, such as $^{32}$P; and sulfur, such as $^{35}$S. Certain isotopically-labeled compounds of the present invention, for example, those incorporating a radioactive isotope, are useful in drug and/or substrate tissue distribution studies (e.g., assays). The radioactive isotopes tritium, i.e., $^3$H, and carbon-14, i.e., $^{14}$C, are particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements and, hence, may be preferred in some circumstances. Substitution with positron-emitting isotopes, such as $^{11}$C, $^{15}$F, $^{18}$F, $^{15}$O and $^{13}$N, can be useful in positron emission tomography (PET) studies for examining substrate receptor occupancy. Isotopically labeled compounds of the present invention can generally be prepared by conventional techniques known to those skilled in the art or by processes analogous to those described in the accompanying Schemes and/or in the Examples and Preparations using an appropriate isotopically labeled reagent in place of the non-labeled reagent previously employed. Pharmaceutically acceptable solvates in accordance with the invention include those wherein the solvent of crystallization may be isotopically substituted, e.g., $D_2O$, acetone-$d_6$, or DMSO-$d_6$. Compounds of the invention, which include compounds exemplified in Examples 1-104 described below, include isotopically labeled versions of these compounds, such as, but not limited to, the deuterated and tritiated isotopes and all other isotopes discussed above.

Compounds

The compounds of Formula I, as described above, contain an imidazo[1,2-b]pyridazine core wherein the core is substituted at the 3-position by an $R^1$ moiety that is optionally substituted with one to three $R^2$; optionally substituted at the 5-, 6- and/or 7-positions by an $R^3$ moiety; and the nitrogen of the amide moiety attached to the 2-position of the imidazo[1,2-b]pyridazine core is substituted with $R^6$ and $R^7$.

In one embodiment, in Formula I as described above, m is 0 and $R^1$ is a (4- to 10-membered)heterocycloalkyl optionally substituted with one to three $R^2$.

In certain embodiments, when $R^1$ is an optionally substituted (4- to 10-membered)heterocycloalkyl, the heterocycloalkyl is selected from the group consisting of azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, octahydrobenzofuranyl, octahydrobenzimidazolyl, octaohydrobenzothiazolyl, imidazolidinyl, pyrrolidinyl, piperidinyl, piperazinyl, oxazolidinyl, isothiazolidinyl, thiazolidinyl, pyrazolidinyl, thiomorpholinyl, tetrahydropyranyl, tetrahydrothiazinyl, tetrahydrothiadiazinyl, tetrahydrooxazolyl, morpholinyl, oxetanyl, tetrahydrodiazinyl, dihydrooxazinyl, oxathiazinyl, quinuclidinyl, chromanyl, isochromanyl, dihydrobenzodioxinyl, benzodioxolyl, benzoxazinyl, indolinyl, dihydrobenzofuranyl, tetrahydroquinolyl, isochromanyl, dihydro-1H-isoindolyl, 2-azabicyclo[2.2.1]heptanonyl, 3-azabicyclo[3.1.0]hexanyl, and 3-azabicyclo[4.1.0]heptanyl.

In certain other embodiments, when $R^1$ is an optionally substituted (4- to 10-membered)heterocycloalkyl, the heterocycloalkyl is selected from dihydrobenzofuranyl, benzodioxolyl, or dihydrobenzodioxinyl.

In another embodiment, in Formula I as described above, $R^1$ is a ($C_6$-$C_{10}$)aryl optionally substituted with one to three $R^2$.

In certain embodiments, when $R^1$ is an optionally substituted ($C_6$-$C_{10}$)aryl the aryl is selected from phenyl or naphthyl.

In certain other embodiments, when $R^1$ is an optionally substituted ($C_6$-$C_{10}$)aryl the aryl is phenyl.

In another embodiment, in Formula I as described above, $R^1$ is a (5- to 14-membered)heteroaryl optionally substituted with one to three $R^2$.

In certain embodiments, $R^1$ is an optionally substituted (5- to 10-membered)heteroaryl.

In certain other embodiments, when $R^1$ is an optionally substituted (5- to 10-membered)heteroaryl, the heteroaryl is selected from the group consisting of triazolyl, imidazolyl, furanyl, isoxazolyl, isothiazolyl, 1,2,3-, 1,2,4, 1,2,5-, or 1,3,4-oxadiazolyl, oxazolyl, thiophenyl, thiazolyl, isothiazolyl, pyrazolyl, pyridinyl, pyrazinyl, pyrimidinyl, pyridazinyl, indolyl, indazolyl, benzofuranyl, benzimidazolyl, benzothienyl, benzoxadiazolyl, benzothiazolyl, isobenzothiofuranyl, benzothiofuranyl, benzisoxazolyl, benzoxazolyl, benzodioxolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl, quinolinyl, isoquinolinyl, cinnolinyl, quinazolinyl, oxochromenyl, and 1,4-benzoxazinyl.

In certain other embodiments, $R^1$ is an optionally substituted (5- to 10-membered)nitrogen-containing heteroaryl. For example, when $R^1$ is an optionally substituted (5- to 10-membered)nitrogen-containing heteroaryl, the heteroaryl is selected from triazolyl, imidazolyl, pyrazolyl, pyridinyl, pyrazinyl, pyrimidinyl, pyridazinyl, indolyl, indazolyl, benzimidazolyl, purinyl, imidazopyridinyl, imidazopyrimidinyl, pyrrolopyridinyl, triazolopyrimidinyl, triazolopyridinyl, pyrazolopyridinyl, pyrazolopyrimidinyl, quinolinyl, cinnolinyl, quinazolinyl, isoquinolinyl, or quinoxalinyl.

In certain other embodiments, when $R^1$ is an optionally substituted (5- to 10-membered)nitrogen-containing heteroaryl, the heteroaryl is selected from triazolyl, imidazolyl, pyrazolyl, pyridinyl, pyrazinyl, pyrimidinyl, pyridazinyl, triazolopyridinyl, pyrazolopyridinyl, pyrazolopyrimidinyl, or quinoxalinyl.

In certain other embodiments, $R^1$ is an optionally substituted (6-membered)nitrogen-containing heteroaryl. For example, when $R^1$ is an optionally substituted (6-membered) nitrogen-containing heteroaryl, the heteroaryl is selected from pyridinyl, pyrazinyl, pyrimidinyl or pyridazinyl.

In certain embodiments, when $R^1$ is an optionally substituted (6-membered)nitrogen-containing heteroaryl, the heteroaryl is selected from pyrimidinyl or pyridinyl.

In certain other embodiments, $R^1$ is an optionally substituted (5-membered)nitrogen-containing heteroaryl. For example, when $R^1$ is an optionally substituted (5-membered) nitrogen-containing heteroaryl, the heteroaryl is selected from triazolyl, imidazolyl, or pyrazolyl.

In any of the preceding embodiments, where chemically permissible, when $R^1$ is substituted with one to three $R^2$, each $R^2$ is independently selected from the group consisting of halogen, oxo, cyano, hydroxy, optionally substituted ($C_1$-$C_6$)alkyl, and optionally substituted ($C_1$-$C_6$)alkoxy.

In certain embodiments, when $R^2$ is a halogen, the halogen is selected from fluoro and chloro.

In certain other embodiments, when $R^2$ is an optionally substituted $(C_1-C_6)$alkyl, the alkyl is selected from methyl, ethyl or propyl, and the methyl, ethyl and propyl are optionally substituted with one to three fluorine atoms. For example, an optionally substituted alkyl includes, but is not limited to, fluoromethyl, difluoromethyl, trifluoromethyl, fluoroethyl, difluoroethyl, trifluoroethyl, and the like.

In yet another embodiment, when $R^2$ is an optionally substituted $(C_1-C_6)$alkoxy, the alkoxy is selected from methoxy, ethoxy or propoxy and the methoxy, ethoxy and propoxy are optionally substituted with one to three fluorine atoms. For example, an optionally substituted alkoxy includes, but is not limited to, fluoromethoxy, difluoromethoxy, trifluoromethoxy, fluoroethoxy, difluoroethoxy, trifluoroethoxy, and the like.

It is to be understood that any of the above-mentioned subgenuses of $R^1$ can be combined together with any of the embodiments for $R^3$, $R^6$ and $R^7$ as described above and hereinafter. For example, in one embodiment, when $R^1$ is an optionally substituted $(C_6-C_{10})$aryl and the aryl is phenyl, b can be 0 ($R^3$ is absent); and one of $R^6$ and $R^7$ can be hydrogen and the other an optionally substituted $(C_3-C_8)$ cycloalkyl, such as cyclopropyl.

In another embodiment, in Formula I as described above, n is an integer selected from 0, 1, or 2; and $R^6$ and $R^7$ are each independently selected from the group consisting of hydrogen, optionally substituted $(C_1-C_6)$alkyl, —$(CH_2)$, —$(C_3-C_8)$cycloalkyl, —$(CH_2)_n$—$(C_6-C_{10})$aryl, and —$(CH_2)_n$-(5- to 6-membered)heteroaryl, and where chemically permissible, the $(C_3-C_8)$cycloalkyl, $(C_6-C_{10})$aryl, and (5- to 6-membered)heteroaryl are optionally substituted with one to three $R^8$; or $R^6$ and $R^7$ taken together with the nitrogen to which they are attached form a (4- to 6-membered)heterocycloalkyl, and where chemically permissible, the (4- to 6-membered)-heterocycloalkyl is optionally substituted with one to three $R^9$;

when present, each $R^8$ is independently selected from the group consisting of halogen, oxo, cyano, hydroxy, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, —$N(R^4)(R^5)$, —$N(R^4)(C=(O)R^5)$, —$C(=O)N(R^4)(R^5)$, —$C(=O)$—$O$—$N(R^4)(R^5)$, —$C(=O)$—$R^4$, and —$C(=O)$—$OR^4$; and when present, each $R^9$ is independently selected from the group consisting of halogen, oxo, cyano, hydroxy, —$SF_5$, nitro, optionally substituted $(C_1-C_6)$alkyl, optionally substituted $(C_2-C_6)$alkenyl, optionally substituted $(C_2-C_6)$alkynyl, optionally substituted $(C_1-C_6)$alkylthio, optionally substituted $(C_1-C_6)$alkoxy, —$N(R^4)(R^5)$, —$N(R^4)(C=(O)R^5)$, —$C(=O)N(R^4)(R^5)$, —$C(=O)$—$O$—$N(R^4)(R^5)$, —$C(=O)$—$R^4$, and —$C(=O)$—$OR^4$.

In certain embodiments, in Formula I as described above, one of $R^6$ and $R^7$ is hydrogen and the other is an optionally substituted $(C_1-C_6)$alkyl.

In certain embodiments, when one of $R^6$ and $R^7$ is an optionally substituted $(C_1-C_6)$alkyl, the alkyl is selected from the group consisting of methyl, ethyl, propyl, isopropyl, butyl, tert-butyl, pentyl and hexyl, wherein the methyl, ethyl, propyl, isopropyl, butyl, tert-butyl, pentyl and hexyl are optionally substituted with one or more fluorine atoms.

In certain other embodiments, when one of $R^6$ and $R^7$ is an optionally substituted $(C_1-C_6)$alkyl, the alkyl is selected from methyl, ethyl or propyl and the methyl, ethyl and propyl are optionally substituted with one to three fluorine atoms. For example, the optionally substituted $(C_1-C_6)$alkyl is selected from fluoromethyl, difluoromethyl, trifluoromethyl, fluoroethyl, difluoroethyl, or trifluoroethyl.

In another embodiment, in Formula I as described above; n is an integer selected from 0, 1, or 2; and one of $R^6$ and $R^7$ is hydrogen and the other is —$(CH_2)_n$—$(C_3-C_8)$cycloalkyl, wherein the cycloalkyl is optionally substituted with one to three $R^8$.

In certain embodiments, when one of $R^6$ and $R^7$ is an optionally substituted $(C_3-C_8)$cycloalkyl, the cycloalkyl is selected from cyclopropyl, cyclobutyl, cyclopentyl, cyclohexyl, cyclooctyl or bicyclo[1.1.1]pentyl.

In certain embodiments, when one of $R^6$ and $R^7$ is an optionally substituted $(C_3-C_8)$cycloalkyl, the cycloalkyl is selected from cyclopropyl or bicyclo[1.1.1]pentyl.

In certain embodiments, when one of $R^6$ and $R^7$ is an optionally substituted $(C_3-C_8)$cycloalkyl, the cycloalkyl is cyclopropyl.

In another embodiment, in Formula I as described above; n is selected from 0, 1, or 2; and one of $R^6$ and $R^7$ is hydrogen and the other is —$(CH_2)_n$—$(C_6-C_{10})$aryl, wherein the aryl is optionally substituted with one to three $R^8$.

In certain embodiments, when one of $R^6$ and $R^7$ is an optionally substituted $(C_6-C_{10})$aryl the $(C_6-C_{10})$aryl is selected from phenyl or naphthyl.

In certain embodiments, when one of $R^6$ and $R^7$ is an optionally substituted $(C_6-C_{10})$aryl the $(C_6-C_{10})$aryl is phenyl.

In another embodiment, in Formula I as described above; one of $R^6$ and $R^7$ is hydrogen and the other is —$(CH_2)_n$-(5- to 6-membered)heteroaryl, wherein the heteroaryl is optionally substituted with one to three $R^8$.

In certain embodiments, when one of $R^6$ and $R^7$ is an optionally substituted (5- to 6-membered)heteroaryl, the heteroaryl is selected from triazolyl, imidazolyl, furanyl, isoxazolyl, isothiazolyl, 1,2,3-, 1,2,4, 1,2,5-, or 1,3,4-oxadiazolyl, oxazolyl, thiophenyl, thiazolyl, isothiazolyl, pyrazolyl, pyridinyl, pyrazinyl, pyrimidinyl, or pyridazinyl.

In certain embodiments, when one of $R^6$ and $R^7$ is an optionally substituted (5- to 6-membered)heteroaryl, the heteroaryl is oxazolyl.

In certain embodiments, when one of $R^6$ and $R^7$ is an optionally substituted (5- to 6-membered)heteroaryl, the heteroaryl is a (5- to 6-membered)nitrogen-containing heteroaryl.

In certain embodiments, when one of $R^6$ and $R^7$ is an optionally substituted (5- to 6-membered)nitrogen-containing heteroaryl, the heteroaryl is selected from triazolyl, imidazolyl, pyrazolyl, pyridinyl, pyrazinyl, pyrimidinyl, or pyridazinyl.

In certain embodiments, when one of $R^6$ and $R^7$ is an optionally substituted (5- to 6-membered)nitrogen-containing heteroaryl, the heteroaryl is selected from triazolyl, pyrazolyl, or pyrimidinyl.

In any of the preceding embodiments, when one of $R^6$ and $R^7$ is a $(C_3-C_8)$cycloalkyl, $(C_6-C_{10})$aryl, or (5- to 6-membered)heteroaryl substituted with one to three $R^8$, each $R^8$ is independently selected from the group consisting of halogen, oxo, cyano, hydroxy, optionally substituted $(C_1-C_6)$ alkyl, and optionally substituted $(C_1-C_6)$alkoxy.

In certain embodiments, when $R^8$ is a halogen, the halogen is selected from fluoro and chloro.

In certain other embodiments, when $R^8$ is an optionally substituted $(C_1-C_6)$alkyl, the alkyl is selected from methyl, ethyl or propyl, and the methyl, ethyl and propyl are optionally substituted with one to three fluorine atoms. For example, an optionally substituted alkyl includes, but is not limited to, fluoromethyl, difluoromethyl, trifluoromethyl, fluoroethyl, difluoroethyl, trifluoroethyl, and the like.

In yet another embodiment, when $R^8$ is an optionally substituted $(C_1-C_6)$alkoxy, the alkoxy is selected from methoxy, ethoxy or propoxy and the methoxy, ethoxy and propoxy are optionally substituted with one to three fluorine atoms. For example, an optionally substituted alkoxy includes, but is not limited to, fluoromethoxy, difluoromethoxy, trifluoromethoxy, fluoroethoxy, difluoroethoxy, trifluoroethoxy, and the like.

In another embodiment, in Formula I as described above, $R^6$ and $R^7$ taken together with the nitrogen to which they are attached form a (4- to 6-membered)heterocycloalkyl optionally substituted with one to three $R^9$.

In certain embodiments, when $R^6$ and $R^7$ taken together with the nitrogen to which they are attached form a (4- to 6-membered)heterocycloalkyl, the heterocycloalkyl is selected from azetidinyl, tetrahydropyrazolyl, tetrahydrooxazinyl, tetrahydropyrimidinyl, imidazolidinyl, piperidinyl, piperazinyl, oxazolidinyl, or pyrrolidinyl.

In certain embodiments, when $R^6$ and $R^7$ taken together with the nitrogen to which they are attached form a (4- to 6-membered)heterocycloalkyl, the heterocycloalkyl is azetidinyl.

In any of the preceding embodiments, when $R^6$ and $R^7$ taken together with the nitrogen to which they are attached form a (4- to 6-membered)heterocycloalkyl substituted with one to three $R^9$, each $R^9$ is independently selected from the group consisting of halogen, oxo, cyano, hydroxy, optionally substituted $(C_1-C_6)$alkyl, and optionally substituted $(C_1-C_6)$ alkoxy.

In certain embodiments, when $R^9$ is a halogen, the halogen is selected from fluoro and chloro.

In certain other embodiments, when $R^9$ is an optionally substituted $(C_1-C_6)$alkyl, the alkyl is selected from methyl, ethyl or propyl, and the methyl, ethyl and propyl are optionally substituted with one to three fluorine atoms. For example, an optionally substituted alkyl includes, but is not limited to, fluoromethyl, difluoromethyl, trifluoromethyl, fluoroethyl, difluoroethyl, trifluoroethyl, and the like.

In yet another embodiment, when $R^9$ is an optionally substituted $(C_1-C_6)$alkoxy, the alkoxy is selected from methoxy, ethoxy or propoxy and the methoxy, ethoxy and propoxy are optionally substituted with one to three fluorine atoms. For example, an optionally substituted alkoxy includes, but is not limited to, fluoromethoxy, difluoromethoxy, trifluoromethoxy, fluoroethoxy, difluoroethoxy, trifluoroethoxy, and the like.

It is to be understood that any of the above-mentioned subgenuses of $R^6$ and $R^7$ can be combined together with any of the embodiments for $R^1$ and $R^3$ as described above and hereinafter. For example, in one embodiment, when one of $R^6$ and $R^7$ is hydrogen and the other is an optionally substituted $(C_3-C_8)$cycloalkyl, such as cyclopropyl, $R^1$ can be an optionally substituted $(C_6-C_{10})$aryl wherein the aryl is phenyl, and b can be 0 ($R^3$ is absent).

In another embodiment, in Formula I as described above, when present, each $R^3$ is independently selected from the group consisting of halogen, cyano, hydroxy, —$SF_5$, nitro, optionally substituted $(C_1-C_6)$alkyl, and optionally substituted $(C_1-C_6)$alkoxy.

In certain embodiments, when $R^3$ is halogen, the halogen is selected from fluoro or chloro.

In certain other embodiments, when $R^3$ is an optionally substituted $(C_1-C_6)$alkyl and/or an optionally substituted $(C_1-C_6)$alkoxy, the $(C_1-C_6)$alkyl and $(C_1-C_6)$alkoxy are as described above in any of the preceding embodiments.

It is to be understood that any of the above-mentioned subgenuses of $R^3$ can be combined together with any of the embodiments for $R^1$, $R^6$ and $R^7$ as described above.

In another embodiment, in Formula I as described above in any of the preceding embodiments, b is 0.

In another embodiment, selected compounds of the present invention may be useful for treating a PDE4B-mediated disorder, comprising administering to a mammal (preferably a human) in need thereof a therapeutically effective amount of a compound of the invention effective in inhibiting PDE4B activity; more preferably, administering an amount of a compound of the invention having improved binding affinity for PDE4B while at the same time possessing less inhibitory activity toward PDE4D.

In certain other embodiments, selected compounds of the present invention may exhibit a binding affinity for the PDE4B isoform.

In certain embodiments, the compounds of the present invention have an enhanced binding affinity for the PDE4B isoform over the PDE4D isoform such that the compounds display about a 2-fold to about a 325-fold binding affinity for the PDE4B isoform over the PDE4D isoform. In certain other embodiments, the compounds of the present invention display about a 5-fold to about a 50-fold binding affinity for the PDE4B isoform over the PDE4D isoform. In certain other embodiments, the compounds of the present invention display about a 51-fold to about a 100-fold binding affinity for the PDE4B isoform over the PDE4D isoform. In certain other embodiments, the compounds of the present invention display about a 101-fold to about a 200-fold binding affinity for the PDE4B isoform over the PDE4D isoform. In certain other embodiments, the compounds of the present invention display about a 201-fold to about a 250-fold binding affinity for the PDE4B isoform over the PDE4D isoform. In certain other embodiments, the compounds of the present invention display about a 251-fold to about a 300-fold binding affinity for the PDE4B isoform over the PDE4D isoform. In certain other embodiments, the compounds of the present invention display about a 301-fold to about a 325-fold binding affinity for the PDE4B isoform over the PDE4D isoform. In certain embodiments, the compounds of the present invention display at least about a 5-fold binding affinity for the PDE4B isoform over the PDE4D isoform. In certain embodiments, the compounds of the present invention display at least about a 10-fold binding affinity for the PDE4B isoform over the PDE4D isoform. In certain embodiments, the compounds of the present invention display at least about a 20-fold binding affinity for the PDE4B isoform over the PDE4D isoform. In certain other embodiments, the compounds of the present invention display at least about a 40-fold binding affinity for the PDE4B isoform over the PDE4D isoform. In certain other embodiments, the compounds of the present invention display at least about a 50-fold binding affinity for the PDE4B isoform over the PDE4D isoform. In certain other embodiments, the compounds of the present invention display at least about a 75-fold binding affinity for the PDE4B isoform over the PDE4D isoform. In certain other embodiments, the compounds of the present invention display at least about a 100-fold binding affinity for the PDE4B isoform over the PDE4D isoform. In certain other embodiments, the compounds of the present invention display at least about a 200-fold binding affinity for the PDE4B isoform over the PDE4D isoform. In certain other embodiments, the compounds of the present invention display at least about a 300-fold binding affinity for the PDE4B isoform over the PDE4D isoform. In certain other embodiments, the compounds of the present invention display up to about a 325-fold binding affinity for the PDE4B isoform over the PDE4D isoform. The binding affinities of the compounds of the present invention for the PDE4B and PDE4D isoforms are shown in Table 3 of the Experimental Section below.

In another embodiment, the present invention provides a pharmaceutical composition comprising a compound of the present invention, or a pharmaceutically acceptable salt thereof, in admixture with at least one pharmaceutically acceptable excipient.

In yet another embodiment, administration of the compounds of the present invention to a patient in need thereof may also lead to a decrease in gastrointestinal discomfort such as emesis, diarrhea, and nausea, which is currently believed to be associated with administration of compounds having binding affinity for other PDE4 isoforms, especially the PDE4D isoform, resulting in an increase in patient compliance as well as overall treatment outcome.

In another embodiment, the present invention provides a method of treating central nervous system (CNS), neuroinflammatory, metabolic, autoimmune and inflammatory diseases or disorders comprising administering to the mammal, particularly a human, in need of such treatment a therapeutically effect amount of a compound of the present invention, or a pharmaceutically acceptable salt thereof.

In another embodiment, the present invention provides the use of a compound of the present invention, or a pharmaceutically acceptable salt thereof, in the manufacture of a medicament for treating central nervous system (CNS), neuroinflammatory, autoimmune and inflammatory diseases or disorders.

Pharmacology

Phosphodiesterases (PDEs) of the PDE4 family are characterized by selective, high-affinity hydrolytic degradation of the second messenger cyclic nucleotide, adenosine 3',5'-cyclic monophosphate (cAMP). The PDE4A, PDE4B and PDE4D subtypes are known to be widely expressed throughout the brain, with regional and intracellular distribution for the PDE4A, PDE4B and PDE4D subtypes being distinct, whereas the PDE4C subtype is expressed at lower levels throughout the central nervous system (See: Siuciak, J. A. et al., *Antipsychotic profile of rolipram: efficacy in rats and reduced sensitivity in mice deficient in the phosphodiesterase-4B (PDE4B) enzyme*, Psychopharmacology (2007) 192:415-424). The location of the PDE4 subtypes makes them an interesting target for exploring new treatments for central nervous system diseases and disorders. For example, PDE4B has been identified as a genetic susceptibility factor for schizophrenia (See: Millar, J. K. et al., *Disrupted in schizophrenia 1 and phosphodiesterase 4B: towards an understanding of psychiatric illness*, J. Physiol. 584 (2007) pp. 401-405).

The PDE4 inhibitor rolipram has been shown to be useful in treating or reversing Aβ-induced memory deficits via the attenuation of neuronal inflammation and apoptosis-mediated cAMP/CREB signaling; thus PDE4 is a potential target for treatment of cognitive deficits associated with AD. (See: Wang, C. et al., *The phosphodiesterase-4 inhibitor rolipram reverses Aβ-induced cognitive impairment and neuroinflammatory and apoptotic responses in rats*, International Journal of Neuropsychopharmacology (2012), 15, 749-766).

PDE4 inhibitors may also possess antidepressant effects by normalizing the cAMP cascade (See: Fujita, M. et al., *Downregulation of Brain Phosphodiesterase Type IV Measured with $^{11}C$—(R)-Rolipram Positron Emission Tomography in Major Depressive Disorder*, Biological Psychiatry, 72, 2012, 548-554).

Furthermore, PDE4 inhibitors have been shown to possess therapeutic activity with implications for the treatment of multiple sclerosis (See: Sun, X. et al., *Rolipram promotes remyelination possibly via MEK-ERK signal pathway in cuprizone-induced demyelination mouse*, Experimental Neurology 2012; 237:304-311).

In view of the above, in certain embodiments, the compounds of the present invention have a wide range of therapeutic applications for the treatment of conditions or diseases of the central nervous system which include neurologic, neurodegenerative and/or psychiatric disorders. Neurologic, neurodegenerative and/or psychiatric disorders include but are not limited to, (1) mood [affective] disorders; (2) neurotic, stress-related and somatoform disorders including anxiety disorders; (3) disorders comprising the symptom of cognitive deficiency in a mammal, including a human; (4) disorders comprising attention deficits, executive function deficits (working memory deficits), dysfunction of impulse control, extrapyramidal symptoms, disorders that are based on a malfunction of basal ganglia; (5) behavioral and emotional disorders with onset usually occurring in childhood and adolescence; (6) disorders of psychological development; (7) systemic atrophies primarily affecting the central nervous system; (8) extrapyramidal and movement disorders; (9) behavioral syndromes associated with physiological disturbances and physical factors; (10) disorders of adult personality and behavior; (11) schizophrenia and other psychotic disorders; (12) mental and behavioral disorders due to psychoactive substance use; (13) sexual dysfunction comprising excessive sexual drive; (14) mental retardation; (15) factitious disorders, e.g., acute hallucinatory mania; (16) episodic and paroxysmal disorders, epilepsy; (17) narcolepsy; and (18) dementia.

Examples of mood [affective] disorders that can be treated according to the present invention include, but are not limited to, bipolar disorder I, hypomania (manic and mixed form), bipolar disorder II; depressive disorders such as single depressive episode or recurrent major depressive disorder, chronic depression, psychotic depression, minor depressive disorder, depressive disorder with postpartum onset, depressive disorders with psychotic symptoms; persistent mood [affective] disorders such as cyclothymia, dysthymia, euthymia; premenstrual syndrome (PMS) and premenstrual dysphoric disorder.

Examples of neurotic, stress-related and somatoform disorders that can be treated according to the present invention include, but are not limited to, anxiety disorders, social anxiety disorder, general anxiety disorder, panic disorder with or without agoraphobia, specific phobia, social phobia, chronic anxiety disorders; obsessive compulsive disorder; reaction to severe stress and adjustment disorders, such as post-traumatic stress disorder (PTSD), acute stress disorder; other neurotic disorders such as depersonalization-derealization syndrome.

The phrase "cognitive deficiency" as used here in "disorders comprising the symptom of cognitive deficiency" refers to a subnormal functioning or a suboptimal functioning in one or more cognitive aspects such as memory, intellect, learning and logic ability, or attention and executive function (working memory) in a particular individual comparative to other individuals within the same general age population.

Examples of "disorders comprising the symptom of cognitive deficiency" that can be treated according to the present invention include, but are not limited to, cognitive deficits primarily but not exclusively related to amnesia, psychosis (schizophrenia), Parkinson's disease, Alzheimer's disease, multi infarct dementia, senile dementia, Lewis body dementia, stroke, frontotemporal dementia, progressive supranuclear palsy, Huntington's disease, HIV disease (HIV-associated dementia), cerebral trauma and drug abuse; mild cognitive disorder ADHD, Asperger's syndrome, and age-associated memory impairment; cognitive decline or delerium post operative or in association with intensive care therapy.

Examples of disorders usually first diagnosed in infancy, childhood and adolescence that can be treated according to the present invention include, but are not limited to, hyperkinetic disorders including disturbance of activity and attention, attention deficit/hyperactivity disorder (ADHD), hyperkinetic conduct disorder; attention deficit disorder (ADD); conduct disorders, including but not limited to depressive conduct disorder; tic disorders including transient tic disorder, chronic motor or vocal tic disorder, combined vocal and multiple motor tic disorder (Gilles de la Tourette's syndrome), substance induced tic disorders; autistic disorders; Batten disease, excessive masturbation, nail-biting, nose-picking and thumb-sucking.

Examples of disorders of psychological development that can be treated according to the present invention include, but are not limited to pervasive developmental disorders, including but not limited to Asperger's syndrome and Rett syndrome, autistic disorders, childhood autism and overactive disorder associated with mental retardation and stereotyped movements, specific developmental disorder of motor function, specific developmental disorders of scholastic skills.

Examples of systemic atrophies primarily affecting the central nervous system that can be treated according to the present invention include, but are not limited to, multiple sclerosis systemic atrophies primarily affecting the basal ganglia including Huntington's disease, and amyotrophic lateral sclerosis.

Examples of extrapyramidal and movement disorders with malfunction and/or degeneration of basal ganglia that can be treated according to the present invention include, but are not limited to, Parkinson's disease; second Parkinsonism such as postencephalitic Parkinsonism; Parkinsonism comprised in other disorders; Niemann-Pick disease, Lewy body disease; degenerative diseases of the basal ganglia; other extrapyramidal and movement disorders including tremor, essential tremor and drug-induced tremor, myoclonus, chorea and drug-induced chorea, drug-induced tics and tics of organic origin, drug-induced acute dystonia, drug-induced tardive dyskinesia, muscular spasms and disorders associated with muscular spasticity or weakness including tremors; mental deficiency (including spasticity, Down syndrome and fragile X syndrome), L-dopa-induced dyskinesia; restless leg syndrome and Stiff-man syndrome.

Further examples of movement disorders with malfunction and/or degeneration of basal ganglia that can be treated according to the present invention include, but are not limited to, dystonia including but not limited to focal dystonia, multiple-focal or segmental dystonia, torsion dystonia, hemispheric, generalized and tardive dystonia (induced by psychopharmacological drugs). Focal dystonia include cervical dystonia (torticolli), blepharospasm (cramp of the eyelid), appendicular dystonia (cramp in the extremities, like the writer's cramp), or mandibular dystonia and spasmodic dysphonia (cramp of the vocal cord); neuroleptic-induced movement disorders including but not limited to neuroleptic malignant syndrome (NMS), neuroleptic-induced Parkinsonism, neuroleptic-induced early onset or acute dyskinesia, neuroleptic-induced acute dystonia, neuroleptic-induced acute akathisia, neuroleptic-induced tardive dyskinesia, neuroleptic-induced tremor.

Examples of behavioral syndromes associated with physiological disturbances and physical factors according to the present invention include, but are not limited to, nonorganic sleep disorders, including but not limited to nonorganic hypersomnia, nonorganic disorder of the sleep-wake schedule (circadian rhythm sleep disorder), insomnia, parasomnia and sleep deprivation; mental and behavioral disorders associated with the puerperium including postnatal and postpartum depression; eating disorders, including but not limited to anorexia nervosa, bulimia nervosa, binge eating disorder, hyperphagia, obesity, compulsive eating disorders and pagophagia.

Examples of disorders of adult personality and behavior that can be treated according to the present invention include, but are not limited to, personality disorders, including but not limited to emotionally unstable, borderline, obsessive-compulsive, anankastic, dependent and passive-aggressive personality disorder; habit and impulse disorders (impulse-control disorder) including intermittent explosive disorder, pathological gambling, pathological fire-setting (pyromania), pathological stealing (kleptomania), trichotillomania; Munchausen syndrome.

Examples of schizophrenia and other psychotic disorders that can be treated according to the present invention include, but are not limited to, continuous or episodic schizophrenia of different types (for instance paranoid, hebephrenic, catatonic, undifferentiated, residual, and schizophreniform disorders); schizotypal disorders (such as borderline, latent, prepsychotic, prodromal, pseudoneurotic pseudopsychopathic schizophrenia and schizotypal personality disorder); persistent delusional disorders; acute, transient and persistent psychotic disorders; induced delusional disorders; schizoaffective disorders of different type (for instance manic depressive or mixed type); puerperal psychosis and other and unspecified nonorganic psychosis.

Examples of mental and behavioral disorders due to psychoactive substance use that can be treated according to the present invention include, but are not limited to, mental and behavioral disorders due to use of alcohol, opioids, cannabinoids, sedatives or hypnotics, cocaine; mental and behavioral disorders due to the use of other stimulants including caffeine, mental and behavioral disorders due to drug dependence and abuse (e.g., narcotic dependence, alcoholism, amphetamine and methamphetamine dependence, opioid dependence, cocaine addiction, nicotine dependence, and drug withdrawal syndrome, and relapse prevention), use of hallucinogens, tobacco (nicotine), volatile solvents and mental and behavioral disorders due to multiple drug use and use of other psychoactive substances including the following subtype symptoms: harmful use, dependence syndrome, withdrawal state, and withdrawal state with delirium.

Examples of dementia that can be treated according to the present invention include, but are not limited to, vascular dementia, dementia due to Creutzfeld-Jacob disease, HIV, head trauma, Parkinson's, Huntington's, Pick's disease, dementia of the Alzheimer's type.

In certain embodiments, the present invention is directed to methods for the treatment of schizophrenia by administration of a therapeutically effective amount of a compound of the present invention to a patient in need thereof.

In certain other embodiments, the invention is further directed to a method for the treatment of cognitive impairment associated with schizophrenia by administration of a therapeutically effective amount of a compound of the present invention to a patient in need thereof.

In addition to the central nervous system disorders mentioned above, there is extensive literature in the art describing the effects of PDE inhibitors on various autoimmune and inflammatory cell responses, which in addition to cAMP increase, include inhibition of superoxide production, degranulation, chemotaxis and tumor necrosis factor (TNF) release in eosinophils, neutrophils and monocytes. Therefore, the compounds of the present invention may be useful for treating autoimmune and Inflammatory diseases. (See: Schett, G. et al., *Apremilast: A novel PDE*4 *Inhibitor in the Treatment of Autoimmune and Inflammatory Diseases*, Ther. Adv. Musculoskeletal Dis. 2010; 2(5):271-278). For example, the compounds of the present invention may be useful for treatment of oral ulcers associated with Behçet's disease. The compounds of the present invention may also be useful for the treatment of pain associated with arthritis (See: Hess, A. et al., *Blockade of TNF-α rapidly inhibits pain responses in the central nervous system*, PNAS, vol. 108, no. 9, 3731-3736 (2011) or for the treatment of psoriasis or psoriatic arthritis (See: Schafer, P., *Apremilast mechanism of action and application to psoriasis and psoriatic arthritis*, Biochem. Pharmacol. (2012), 15; 83(12): 1583-90). Accordingly, compounds of the present invention may also be useful for treatment of ankylosing spondylitis [see: Patan, E. et al., *Efficacy and safety of apremilast, an oral phosphodiesterase* 4 *inhibitor, in ankylosing spondylitis*, Ann. Rheum. Dis. (Sep. 14, 2102)]. Other conditions treatable by administration of the compounds of the present invention include, but are not limited to, acute and chronic airway diseases such as, but not limited to, asthma, chronic or acute bronchoconstriction, chronic bronchitis, bronchiectasis, small airways obstruction, emphysema, obstructive or inflammatory airways diseases, acute respiratory distress syndrome (ARDS), COPD, pneumoconiosis, seasonal allergic rhinitis or perennial allergic rhinitis or sinusitis, and acute lung injury (ALI).

In yet another embodiment, the compounds of the present invention may be useful for treating rheumatoid arthritis, gout, and fever, edema and pain associated with inflammation, eosinophil-related disorders, dermatitis or eczema, urticaria, conjunctivitis, uveitis, psoriasis, inflammatory bowel disease, sepsis, septic shock, liver injury, pulmonary hypertension, pulmonary edema, bone loss disease, and infection.

In yet another embodiment, the compounds of the present invention may be useful for treating cancer. For example, the compounds of the present invention may be useful for treatment of brain cancer (e.g., medulloblastoma) (See: Schmidt, A. L., *BDNF and PDE*4*, but not GRPR, Regulate Viability of Human Medulloblastoma Cells*, J. Mol. Neuroscience (2010) 40:303-310). The compounds of the present invention may also be useful for treating melanoma (See: Marquette, A. et al., *ERK and PDE*4 *cooperate to induce RAF isoform switching in melanoma*, Nature Structural & Molecular Biology, vol. 18, no. 5, 584-91, 2011). In certain embodiments, the compounds of the present invention may be useful for treating leukemia, e.g., chronic lymphocytic leukemia, (See: Kim, D. H. et al., *Type* 4 *Cyclic Adenosine Monophosphate Phosphodiesterase as a Therapeutic Target in Chronic Lymphocytic Leukemia*, Blood Journal of The American Society of Hematology, Oct. 1, 1998, vol. 92, no. 7 2484-2494). In other embodiments, the compounds may be useful for treating brain or ophthamological tumors.

In certain other embodiments, the compounds of the present invention may be useful for treating diabetes or diseases associated with diabetes (See: Vollert, S. et al., *The glucose-lowering effects of the PDE*4 *inhibitors roflumilast and roflumilast-N-oxide in db/db mice*, Diabetologia (2012) 55:2779-2788. Wouters, E. F. M. et al., *Effect of the Phosphodiesterase* 4 *Inhibitor Roflumilast on Glucose Metabolism in Patients with Treatment-Naïve, Newly Diagnosed Type* 2 *Diabetes Mellitus*, Journal of Clinical Endocrinology and Metabolism 2012, 97, 1720-1725). Other examples include, but are not limited to, diabetic macular degeneration, diabetic neuropathy, obesity, type 2 diabetes (non-insulin dependent diabetes), metabolic syndrome, glucose intolerance, urinary incontinence (e.g., bladder overactivity), diabetic macular edema, nephropathy and related health risks, symptoms or disorders. As such, the compounds can also be used to reduce body fat or body weight of an overweight or obese individual.

In certain other embodiments, the compounds of the present invention may be useful in the prevention and treatment of disorders associated with enhanced endothelial activity, impaired endothelial barrier function and/or enhanced neoangiogenesis, such as septic shock; angioedema, peripheral edema, communicating or non-communicating hydrocephalus, vascular edema, cerebral edema; reduced natriuria pathology; inflammatory diseases, including asthma, rhinitis, arthritis and rheumatoid diseases and autoimmune diseases; acute renal or liver failure, liver dysfunction; psoriasis, Irritable Bowel Disease (IBD), Crohn's disease, and benign/malignant neoplasia.

In certain other embodiments, the compounds of the present invention may be useful for treating diseases of the spinal cord and/or peripheral nervous system, including spinal cord injury, spinal cord edema, spinal cord tumors, vascular malformations or anomalies of the spinal cord, syringomyelia, and hydromyelia.

In certain other embodiments, the compounds described herein are further useful in the prevention and treatment of disorders associated with thrombosis, embolism, or ischemic disorders including, but not limited to, thrombosis-induced tissue infarction in coronary artery disease, in cerebrovascular disease (including cerebral arteriosclerosis, cerebral amyloid angiopathy, hereditary cerebral hemorrhage, and brain hypoxia-ischemia) and/or in peripheral vascular disease; stable and unstable angina, transient ischemic attacks, stroke, atherosclerosis, myocardial infarct, cerebral infarct, reperfusion injury (brain/cardiac), traumatic brain injury, subdural, epidural or subarachnoid hemorrhage, migraine, cluster and tension headaches, placental insufficiency, thrombosis after surgical procedures, such as bypass, angioplasty, stent placement, and heart valve replacement.

In certain other embodiments, the compounds described herein are further useful for treating pain conditions and disorders. Examples of such pain conditions and disorders include, but are not limited to, inflammatory pain, hyperalgesia, inflammatory hyperalgesia, migraine, cancer pain, osteoarthritis pain, post-surgical pain, non-inflammatory pain, neuropathic pain, sub-categories of neuropathic pain including peripheral neuropathic pain syndromes, chemotherapy-induced neuropathy, complex regional pain syndrome, HIV sensory neuropathy, neuropathy secondary to tumor infiltration, painful diabetic neuropathy, phantom limb pain, postherpetic neuralgia, postmastectomy pain, trigeminal neuralgia, central neuropathic pain syndromes, central post-stroke pain, multiple sclerosis pain, Parkinson disease pain, and spinal cord injury pain.

In certain other embodiments, the compounds described herein are further useful for treating wounds (or promoting wound healing), burns, scarring, and related conditions.

In certain other embodiments, the compounds described herein are further useful for treating neuronal damage disorders (including ocular damage, retinopathy including diabetic macular edema or macular degeneration of the eye, tinnitus, hearing impairment and loss, and brain edema).

In certain other embodiments, the compounds described herein are further useful for treating transplant rejection, allograft rejection, renal and liver failure, and restless leg syndrome.

Formulations

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be formulated such that administration topically to the skin or mucosa (i.e., dermally or transdermally) leads to systemic absorption of the compound. In another embodiment, the compounds of the invention can also be formulated such that administration intranasally or by inhalation leads to systemic absorption of the compound. In another embodiment, the compounds of the invention may be formulated such that administration rectally or vaginally leads to systemic absorption of the compound.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, the total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing 0.01, 0.05, 0.1, 0.5, 1.0, 2.5, 5.0, 10.0, 15.0, 25.0, 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compounds of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically (e.g., intranasal or ophthalmic).

Oral administration of a solid dose form may be, for example, presented in discrete units, such as hard or soft capsules, pills, cachets, lozenges, or tablets, each containing a predetermined amount of at least one compound of the present invention.

In another embodiment, the oral administration may be in a powder or granule form. In another embodiment, the oral dose form is sub-lingual, such as, for example, a lozenge. In such solid dosage forms, the compounds of the present invention are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (i.e., sterile injectable aqueous or oleaginous suspensions)

may be formulated according to the known art using suitable dispersing, wetting, and/or suspending agents, and include depot formulations.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound that enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, J. Pharm. Sci., 88 (10), 955-958 (1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone; as a mixture, for example, in a dry blend with lactose; or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be administered simultaneously (either in the same dosage form or in separate dosage forms) or sequentially. An exemplary therapeutic agent may be, for example, a metabotropic glutamate receptor agonist.

The administration of two or more compounds "in combination" means that the two compounds are administered closely enough in time that the presence of one alters the biological effects of the other. The two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a PDE4 inhibitor compound of the present invention and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of the present invention or a pharmaceutically acceptable salt of the compound; (b) a second pharmaceutically active agent; and (c) a pharmaceutically acceptable carrier, vehicle or diluent.

Various pharmaceutically active agents may be selected for use in conjunction with the compounds of the present invention, depending on the disease, disorder, or condition to be treated. Pharmaceutically active agents that may be used in combination with the compositions of the present invention include, without limitation:

(i) acetylcholinesterase inhibitors, such as donepezil hydrochloride (ARICEPT, MEMAC), physostigmine salicylate (ANTILIRIUM), physostigmine sulfate (ESERINE), metrifonate, neostigmine, ganstigmine, pyridostigmine (MESTINON), ambenonium (MYTELASE), demarcarium, Debio 9902 (also known as ZT-1; Debiopharm), rivastigmine (EXELON), ladostigil, NP-0361, galantamine hydrobromide (RAZADYNE, RIMINYL, NIVALIN), tacrine (COGNEX), tolserine, velnacrine maleate, memoquin, huperzine A (HUP-A; NeuroHitech), phenserine, edrophonium (ENLON, TENSILON), and INM-176;

(ii) amyloid-β (or fragments thereof), such as $A\beta_{1-15}$ conjugated to pan HLA DR-binding epitope (PADRE), ACC-001 (Elan/Wyeth), ACI-01, ACI-24, AN-1792, Affitope AD-01, CAD106, and V-950;

(iii) antibodies to amyloid-β (or fragments thereof), such as ponezumab, solanezumab, bapineuzumab (also known as AAB-001), AAB-002 (Wyeth/Elan), ACI-01-Ab7, BAN-2401, intravenous Ig (GAMMAGARD), LY2062430 (humanized m266; Lilly), R1450 (Roche), ACU-5A5, huCO91, and those disclosed in International Patent Publication Nos WO004/032868, WO005/025616, WO006/036291, WO006/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(iv) amyloid-lowering or -inhibiting agents (including those that reduce amyloid production, accumulation and fibrillization) such as dimebon, davunetide, eprodisate, leuprolide, SK-PC-B70M, celecoxib, lovastatin, anapsos, oxiracetam, pramiracetam, varenicline, nicergoline, colostrinin, bisnorcymserine (also known as BNC), NIC5-15 (Humanetics), E-2012 (Eisai), pioglitazone, clioquinol (also known as PBT1), PBT2 (Prana Biotechnology), flurbiprofen (ANSAID, FROBEN) and its R-enantiomer tarenflurbil (FLURIZAN), nitroflurbiprofen, fenoprofen (FENOPRON, NALFON), ibuprofen (ADVIL, MOTRIN, NUROFEN), ibuprofen lysinate, meclofenamic acid, meclofenamate sodium (MECLOMEN), indomethacin (INDOCIN), diclofenac sodium (VOLTAREN), diclofenac potassium, sulindac (CLINORIL), sulindac sulfide, diflunisal (DOLOBID), naproxen (NAPROSYN), naproxen sodium (ANAPROX, ALEVE), ARC031 (Archer Pharmaceuticals), CAD-106 (Cytos), LY450139 (Lilly), insulin-degrading enzyme (also known as insulysin), the gingko biloba extract EGb-761 (ROKAN, TEBONIN), tramiprosate (CEREBRIL, ALZHEMED), eprodisate (FIBRILLEX, KIACTA), compound W [3,5-bis(4-nitrophenoxy)benzoic acid], NGX-96992, neprilysin (also known as neutral endopeptidase (NEP)), scyllo-inositol (also known as scyllitol), atorvastatin (LIPITOR), simvastatin (ZOCOR), KLVFF-(EEX)3, SKF-74652, ibutamoren mesylate, BACE inhibitors such as ASP-1702, SCH-745966, JNJ-715754, AMG-0683, AZ-12304146, BMS-782450, GSK-188909, NB-533, E2609 and TTP-854; gamma secretase modulators such as ELND-007; and RAGE (receptor for advanced glycation end-products) inhibitors, such as TTP488 (Transtech) and TTP4000 (Transtech), and those disclosed in U.S. Pat. No. 7,285,293, including PTI-777;

(v) alpha-adrenergic receptor agonists, such as guanfacine (INTUNIV, TENEX), clonidine (CATAPRES), metaraminol (ARAMINE), methyldopa (ALDOMET, DOPAMET, NOVOMEDOPA), tizanidine (ZANAFLEX), phenylephrine (also known as neosynephrine), methoxamine, cirazoline, guanfacine (INTUNIV), lofexidine, xylazine, modafinil (PROVIGIL), adrafinil, and armodafinil (NUVIGIL);

(vi) beta-adrenergic receptor blocking agents (beta blockers), such as carteolol, esmolol (BREVIBLOC), labetalol (NORMODYNE, TRANDATE), oxprenolol (LARACOR, TRASACOR), pindolol (VISKEN), propanolol (INDERAL), sotalol (BETAPACE, SOTALEX, SOTACOR), timolol (BLOCADREN, TIMOPTIC), acebutolol (SECTRAL, PRENT), nadolol (CORGARD), metoprolol tartrate (LOPRESSOR), metoprolol succinate (TOPROL-XL), atenolol (TENORMIN), butoxamine, and SR 59230A (Sanofi);

(vii) anticholinergics, such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE), tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL);

(viii) anticonvulsants, such as carbamazepine (TEGRETOL, CARBATROL), oxcarbazepine (TRILEPTAL), phenytoin sodium (PHENYTEK), fosphenytoin (CEREBYX, PRODILANTIN), divalproex sodium (DEPAKOTE), gabapentin (NEURONTIN), pregabalin (LYRICA), topirimate (TOPAMAX), valproic acid (DEPAKENE), valproate sodium (DEPACON), 1-benzyl-5-bromouracil, progabide, beclamide, zonisamide (TRERIEF, EXCEGRAN), CP-465022, retigabine, talampanel, and primidone (MYSOLINE);

(ix) antipsychotics, such as lurasidone (LATUDA, also known as SM-13496; Dainippon Sumitomo), aripiprazole (ABILIFY), chlorpromazine (THORAZINE), haloperidol (HALDOL), iloperidone (FANAPTA), flupentixol decanoate (DEPIXOL, FLUANXOL), reserpine (SERPLAN), pimozide (ORAP), fluphenazine decanoate, fluphenazine hydrochloride, prochlorperazine (COMPRO), asenapine (SAPHRIS), loxapine (LOXITANE), molindone (MOBAN), perphenazine, thioridazine, thiothixine, trifluoperazine (STELAZINE), ramelteon, clozapine (CLOZARIL), norclozapine (ACP-104), risperidone (RISPERDAL), paliperidone (INVEGA), melperone, olanzapine (ZYPREXA), quetiapine (SEROQUEL), talnetant, amisulpride, ziprasidone (GEODON), blonanserin (LONASEN), and ACP-103 (Acadia Pharmaceuticals);

(x) calcium channel blockers such as lomerizine, ziconotide, nilvadipine (ESCOR, NIVADIL), diperdipine, amlodipine (NORVASC, ISTIN, AMLODIN), felodipine (PLENDIL), nicardipine (CARDENE), nifedipine (ADALAT, PROCARDIA), MEM 1003 and its parent compound nimodipine (NIMOTOP), nisoldipine (SULAR), nitrendipine, lacidipine (LACIPIL, MOTENS), lercanidipine (ZANIDIP), lifarizine, diltiazem (CARDIZEM), verapamil (CALAN, VERELAN), AR-R 18565 (AstraZeneca), and enecadin;

(xi) catechol O-methyltransferase (COMT) inhibitors, such as nitecapone, tolcapone (TASMAR), entacapone (COMTAN), and tropolone;

(xii) central nervous system stimulants, such as atomoxetine, reboxetine, yohimbine, caffeine, phenmetrazine, phendimetrazine, pemoline, fencamfamine (GLUCOENERGAN, REACTIVAN), fenethylline (CAPTAGON), pipradol (MERETRAN), deanol (also known as dimethylaminoethanol), methylphenidate (DAYTRANA), methylphenidate hydrochloride (RITALIN), dexmethylphenidate (FOCALIN), amphetamine (alone or in combination with other CNS stimulants, e.g., ADDERALL (amphetamine aspartate, amphetamine sulfate, dextroamphetamine saccharate, and dextroamphetamine sulfate)), dextroamphetamine sulfate (DEXEDRINE, DEXTROSTAT), methamphetamine (DESOXYN), lisdexamfetamine (VYVANSE), and benzphetamine (DIDREX);

(xiii) corticosteroids, such as prednisone (STERAPRED, DELTASONE), prednisolone (PRELONE), predisolone acetate (OMNIPRED, PRED MILD, PRED FORTE), prednisolone sodium phosphate (ORAPRED ODT), methylprednisolone (MEDROL); methylprednisolone acetate (DEPO-MEDROL), and methylprednisolone sodium succinate (A-METHAPRED, SOLU-MEDROL);

(xiv) dopamine receptor agonists, such as apomorphine (APOKYN), bromocriptine (PARLODEL), cabergoline (DOSTINEX), dihydrexidine, dihydroergocryptine, fenoldopam (CORLOPAM), lisuride (DOPERGIN), terguride spergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), cariprazine, pardoprunox and sarizotan;

(xv) dopamine receptor antagonists, such as chlorpromazine, fluphenazine, haloperidol, loxapine, risperidone, thioridazine, thiothixene, trifluoperazine, tetrabenazine (NITOMAN, XENAZINE), 7-hydroxyamoxapine, droperidol (INAPSINE, DRIDOL, DROPLETAN), domperidone (MOTILIUM), L-741742, L-745870, raclopride, SB-277011A, SCH-23390, ecopipam, SKF-83566, and metoclopramide (REGLAN);

(xvi) dopamine reuptake inhibitors such as bupropion, safinamide, nomifensine maleate (MERITAL), vanoxerine (also known as GBR-12909) and its decanoate ester DBL-583, and amineptine;

(xvii) gamma-amino-butyric acid (GABA) receptor agonists, such as baclofen (LIORESAL, KEMSTRO), siclofen, pentobarbital (NEMBUTAL), progabide (GABRENE), and clomethiazole;

(xviii) histamine 3 (H3) antagonists such as ciproxifan, tiprolisant, S-38093, irdabisant, pitolisant, GSK-239512, GSK-207040, JNJ-5207852, JNJ-17216498, HPP-404, SAR-110894, trans-N-ethyl-3-fluoro-3-[3-fluoro-4-(pyrrolidin-1-ylmethyl)phenyl]-cyclobutanecarboxamide (PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xix) immunomodulators such as glatiramer acetate (also known as copolymer-1; COPAXONE), MBP-8298 (synthetic myelin basic protein peptide), dimethyl fumarate, fingolimod (also known as FTY720), roquinimex (LINOMIDE), laquinimod (also known as ABR-215062 and SAIK-MS), ABT-874 (human anti-IL-12 antibody; Abbott), rituximab (RITUXAN), alemtuzumab (CAMPATH), daclizumab (ZENAPAX), and natalizumab (TYSABRI);

(xx) immunosuppressants such as methotrexate (TREXALL, RHEUMATREX), mitoxantrone (NOVANTRONE), mycophenolate mofetil (CELLCEPT), mycophenolate sodium (MYFORTIC), azathioprine (AZASAN, IMURAN), mercaptopurine (PURI-NETHOL), cyclophosphamide (NEOSAR, CYTOXAN), chlorambucil (LEUKERAN), cladribine (LEUSTATIN, MYLINAX), alpha-fetoprotein, etanercept (ENBREL), and 4-(benzyloxy)-5-[(5-undecyl-2H-pyrrol-2-ylidene)methyl]-1H, 1'H-2,2'-bipyrrole (also known as PNU-156804);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA), benserazide (MADOPAR), α-methyldopa, monofluromethyldopa, difluoromethyldopa, brocresine, or m-hydroxybenzylhydrazine);

(xxiii) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), LY-233536 and LY-235959 (both Lilly), methadone, (DOLOPHINE), neramexane, perzinfotel, phencyclidine, tianeptine (STABLON), dizocilpine (also known as MK-801), EAB-318 (Wyeth), ibogaine, voacangine, tiletamine, riluzole (RILUTEK), aptiganel (CERESOTAT), gavestinel, and remacimide;

(xxiv) monoamine oxidase (MAO) inhibitors, such as selegiline (EMSAM), selegiline hydrochloride (1-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xxv) muscarinic receptor (particularly M1 subtype) agonists, such as cevimeline, levetiracetam, bethanechol chloride (DUVOID, URECHOLINE), itameline, pilocarpine (SALAGEN), NGX267, arecoline, L-687306 (Merck), L-689660 (Merck), furtrethonium iodide (FURAMON, FURANOL), furtrethonium benzensulfonate, furtrethonium p-toluenesulfonate, McN-A-343, oxotremorine, sabcomeline, AC-90222 (Acadia Pharmaceuticals), and carbachol (CARBASTAT, MIOSTAT, CARBOPTIC);

(xxvi) neuroprotective drugs such as bosutinib, condoliase, airmoclomol, lamotrigine, perampanel, aniracetam, minaprime, riluzole, N-hydroxy-1,2,4,9-tetrahydro-3H-carbazol-3-imine, desmoteplase, anatibant, astaxanthin, neuropeptide NAP (e.g., AL-108 and AL-208; both Allon Therapeutics), neurostrol, perampanel, ispronicline, bis(4-β-D-glucopyranosyloxybenzyl)-2-β-D-glucopyranosyl-2-isobutyltartrate (also known as dactylorhin B or DHB), formobactin, xaliproden (XAPRILA), lactacystin, dimeboline hydrochloride (DIMEBON), disufenton (CEROVIVE), arundic acid (ONO-2506, PROGLIA, CEREACT), citicoline (also known as cytidine 5'-diphosphocholine), edaravone (RADICUT), AEOL-10113 and AEOL-10150 (both Aeolus Pharmaceuticals), AGY-94806 (also known as SA-450 and Msc-1), granulocyte-colony stimulating factor (also known as AX-200), BAY-38-7271 (also known as KN-387271; Bayer AG), ancrod (VIPRINEX, ARWIN), DP-b99 (D-Pharm Ltd), HF-0220 (17-β-hydroxyepiandrosterone; Newron Pharmaceuticals), HF-0420 (also known as oligotropin), pyridoxal 5'-phosphate (also known as MC-1), microplasmin, S-18986, piclozotan, NP031112, tacrolimus, L-seryl-L-methionyl-L-alanyl-L-lysyl-L-glutamyl-glycyl-L-valine, AC-184897 (Acadia Pharmaceuticals), ADNF-14 (National Institutes of Health), stilbazulenyl nitrone, SUN-N8075 (Daiichi Suntory Biomedical Research), and zonampanel;

(xxvii) nicotinic receptor agonists, such as epibatidine, bupropion, CP-601927, varenicline, ABT-089 (Abbott), ABT-594, AZD-0328 (AstraZeneca), EVP-6124, R3487 (also known as MEM3454; Roche/Memory Pharmaceuticals), R4996 (also known as MEM63908; Roche/Memory Pharmaceuticals), TC-4959 and TC-5619 (both Targacept), and RJR-2403;

(xxviii) norepinephrine (noradrenaline) reuptake inhibitors, such as atomoxetine (STRATTERA), doxepin (APONAL, ADAPIN, SINEQUAN), nortriptyline (AVENTYL, PAMELOR, NORTRILEN), amoxapine (ASENDIN, DEMOLOX, MOXIDIL), reboxetine (EDRONAX, VESTRA), viloxazine (VIVALAN), maprotiline (DEPRILEPT, LUDIOMIL, PSYMION), bupropion (WELLBUTRIN), and radaxafine;

(xxix) phosphodiesterase (PDE) inhibitors, including but not limited to, (a) PDE1 inhibitors (e.g., vinpocetine (CAVINTON, CERACTIN, INTELECTOL) and those disclosed in U.S. Pat. No. 6,235,742, (b) PDE2 inhibitors (e.g., erythro-9-(2-hydroxy-3-nonyl)adenine (EHNA), BAY 60-7550, and those described in U.S. Pat. No. 6,174,884), (c) PDE3 inhibitors (e.g., anagrelide, cilostazol, milrinone, olprinone, parogrelil, and pimobendan), (d) PDE4 inhibitors (e.g., apremilast, ibudilastroflumilast, rolipram, Ro 20-1724, ibudilast (KETAS), piclamilast (also known as RP73401), CDP840, cilomilast (ARIFLO), roflumilast, tofimilast, oglemilast (also known as GRC 3886), tetomilast (also known as OPC-6535), lirimifast, theophylline (UNIPHYL, THEOLAIR), arofylline (also known as LAS-31025), doxofylline, RPR-122818, or mesembrine), and (e) PDE5 inhibitors (e.g., sildenafil (VIAGRA, REVATIO), tadalafil (CIALIS), vardenafil (LEVITRA, VIVANZA), udenafil, avanafil, dipyridamole (PERSANTINE), E-4010, E-4021, E-8010, zaprinast, iodenafil, mirodenafil, DA-8159, and those disclosed in International Patent Applications WO2002/020521, WO2005/049616, WO2006/120552, WO2006/126081, WO2006/126082, WO2006/126083, and WO2007/122466), (f) PDE7 inhibitors; (g) PDE8 inhibitors; (h) PDE9 inhibitors (e.g., BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), (i) PDE10 inhibitors such as 2-({4-[1-methyl-4-(pyridin-4-yl)-1H-pyrazol-3-yl]phenoxy}methyl)quinolin-3(4H)-one and SCH-1518291; and (j) PDE11 inhibitors;

(xxx) quinolines, such as quinine (including its hydrochloride, dihydrochloride, sulfate, bisulfate and gluconate salts), chloroquine, sontoquine, hydroxychloroquine (PLAQUENIL), mefloquine (LARIAM), and amodiaquine (CAMOQUIN, FLAVOQUINE);

(xxxi) β-secretase inhibitors, such as ASP-1702, SCH-745966, JNJ-715754, AMG-0683, AZ-12304146, BMS-782450, GSK-188909, NB-533, LY-2886721, E-2609, HPP-854, (+)-phenserine tartrate (POSIPHEN), LSN-2434074 (also known as LY-2434074), KMI-574, SCH-745966, AcrER (N²-acetyl-D-arginyl-L-arginine), loxistatin (also known as E64d), and CA074Me;

(xxxii) γ-secretase inhibitors and modulators, such as BMS-708163 (Avagacest), WO20060430064 (Merck), DSP8658 (Dainippon), ITI-009, L-685458 (Merck), ELAN-G, E LAN-Z, 4-chloro-N-[(2S)-3-ethyl-1-hydroxypentan-2-yl]benzenesulfonamide;

(xxxiii) serotonin (5-hydroxytryptamine) 1A ($5-HT_{1A}$) receptor antagonists, such as spiperone, levo-pindolol, BMY 7378, NAD-299, S-(−)-UH-301, NAN 190, lecozotan;

(xxxiv) serotonin (5-hydroxytryptamine) 2C ($5-HT_{2c}$) receptor agonists, such as vabicaserin and zicronapine;

(xxxv) serotonin (5-hydroxytryptamine) 4 ($5-HT_4$) receptor agonists, such as PRX-03140 (Epix);

(xxxvi) serotonin (5-hydroxytryptamine) 6 ($5-HT_6$) receptor antagonists, such as A-964324, AVI-101, AVN-211, mianserin (TORVOL, BOLVIDON, NORVAL), methiothepin (also known as metitepine), ritanserin, ALX-1161, ALX-1175, MS-245, LY-483518 (also known as SGS518; Lilly), MS-245, Ro 04-6790, Ro 43-68544, Ro 63-0563, Ro 65-7199, Ro 65-7674, SB-399885, SB-214111, SB-258510, SB-271046, SB-357134, SB-699929, SB-271046, SB-742457 (GlaxoSmithKline), Lu AE58054 (Lundbeck A/S), and PRX-07034 (Epix);

(xxxvii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine, neuralstem and tesofensine;

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline, idebenone, PYM50028 (COGANE; Phytopharm), and AIT-082 (NEOTROFIN);

(xxxix) Glycine transporter-1 inhibitors such as paliflutine, ORG-25935, JNJ-17305600, and ORG-26041;

(xl) AMPA-type glutamate receptor modulators such as perampanel, mibampator, selurampanel, GSK-729327, N-{(3S,4S)-4-[4-(5-cyanothiophen-2-yl)phenoxy]tetrahydrofuran-3-yl}propane-2-sulfonamide, and the like.

(xli) Janus kinase inhibitors (JAK) such as, but not limited to, tofacitinib, ruxolitinib, baricitinib, CYT387, GLPG0634, lestaurtinib, pacritinib, and TG101348.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

The compounds of the invention, or their pharmaceutically acceptable salts, may be prepared by a variety of methods that are analogously known in the art. The reaction Scheme described below, together with synthetic methods known in the art of organic chemistry, or modifications and derivatizations that are familiar to those of ordinary skill in the art, illustrate a method for preparing the compounds. Others, including modifications thereof, will be readily apparent to one skilled in the art.

The starting materials used herein are commercially available or may be prepared by routine methods known in the art (such as those methods disclosed in standard reference books such as the COMPENDIUM OF ORGANIC SYNTHETIC METHODS, Vol. I-XII (published by Wiley-Interscience)). Preferred methods include, but are not limited to, those described below.

During any of the following synthetic sequences, it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M.

Wuts, Protective Groups in Organic Chemistry, John Wiley & Sons, 1999; and T. W. Greene and P. G. M. Wuts, Protective Groups in Organic Chemistry, John Wiley & Sons, 2006, which are hereby incorporated by reference.

Compounds of the present invention, or the pharmaceutically acceptable salts of said compounds or tautomers and radioisotopes, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in some cases, the compounds in Scheme 1 will be generated as a mixture of diastereomers and/or enantiomers; these may be separated at various stages of the synthetic Scheme using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the Scheme, methods and examples are used for convenience of representation and/or to reflect the order in which they are introduced in the Scheme, and are not intended to necessarily correspond to the symbols, superscripts or subscripts in the appended claims. The Schemes are representative of methods useful in synthesizing the compounds of the present invention. They are not to constrain the scope of the invention in any way.

Scheme 1 refers to the general synthetic preparation of compounds represented by Formula I. The preparation of compounds represented by Formula A, where R=lower alkyl, have been described previously. A few examples: *Journal of Heterocyclic Chemistry* 1968, 5(1), 35-39; *Il Farmaco—Ed. Sci.* 1977, 36(6), 430-437; *Journal of Heterocyclic Chemistry* 2002, 39, 737-742. The direct installation of the $R^1$ substituent to give the compound of Formula B can be accomplished by C—H insertion/direct arylation reactions. These transformations can be carried out by treatment with an appropriate aryl halide, a metal source (palladium(II) acetate, tetrakis(triphenylphosphine)palladium(0), tris(dibenzylideneacetone)dipalladium(0), copper iodide), a ligand (triphenylphosphine, bis(adamant-1-yl)(butyl)phosphine, 1,10-phenanthroline) and a base (potassium carbonate, cesium carbonate, potassium tert-butoxide) in an appropriate solvent usually heated to temperatures above 50° C. (*RSC Advances* 2012, 2(14), 5972-5975; *Organic Letters* 2012, 14(7), 1688-1691; PCT Int. Appl. 2011075643). During this step the $(R^3)_b$ and $R^1$ moieties should be represented by the same moiety as is desired in the final product. For instance, in the compound of Example 1, b is 0, and $R^1$ is a 4-chlorophenyl moiety. The intermediate of Formula B can then be converted to compounds of Formula I through treatment of the ester with the appropriate amine using heat and a Lewis acid, such as magnesium methoxide or calcium chloride, in an appropriate solvent (see *Tetrahedron Letters* 2010, 51, 3879-3882). During this step, the $R^6$ and $R^7$ moieties should be represented by the same moiety as is desired in the final product. For instance, in Example 4, $R^6$ is cyclopropyl and $R^7$ is hydrogen. Alternatively, the conversion of ester of Formula B to the amide of Formula I can be effected through a two-step process in which the ester is first hydrolyzed to the acid, via acidic or basic treatment in water and a co-solvent; the acid is subsequently converted to the amide by treatment with the appropriate amine in the presence of an amide coupling/dehydrating reagent such as 2,4,6-tripropyl-1,3,5,2,4,6-trioxatriphosphinane 2,4,6-trioxide (T3P), O-(7-azabenzotriazol-1-yl)-N,N,N',N'-tetramethyluronium hexafluorophosphate (HATU), 1,3-dicyclohexylcarbodiimide (DCC), etc., at temperatures ranging from −20° C. to 100° C. to afford compounds of Formula I. During either of these steps the $R^1$ moiety should be represented by the same moiety as is desired in the final product. For instance, in Example 1, $R^1$ should be represented by a 4-chlorophenyl moiety.

Alternately, halogenation of the compound of Formula A by treatment with an electrophilic halogen reagent such as N-iodosuccinimide (NIS), N-bromosuccinimide (NBS), iodine monochloride (ICl), iodine ($I_2$), bromine ($Br_2$), etc., in an inert solvent, optionally acid-catalyzed, from room temperature to 100° C., results in the compound of Formula C wherein X is represented by bromine or iodine. The compound of Formula C can be converted into a compound of Formula I in two ways. The first method employs a substitution of the halogenated imidazopyridazine of Formula C via a Suzuki-Miyaura reaction (*Chemical Society Reviews* 2014, 43, 412-443; *Accounts of Chemical Research* 2013, 46, 2626-2634): treatment with an appropriate alkyl, aryl, or heteroaryl boronate in the presence of base, a transition metal catalyst [potentially palladium(II) acetate or tris(dibenzylideneacetone)dipalladium(0)], and a metal-chelating ligand (generally phosphine-based), in an appropriate solvent installs the appropriate $R^1$ moiety and affords Formula B. The compound of Formula B is then converted to the compound of Formula I as described previously. In a second approach, the intermediate of Formula C may be converted to amide D by treatment of the ester with the appropriate amine in the presence of heat and a Lewis acid, such as magnesium methoxide or calcium chloride. Alternatively, transformation of the intermediate of Formula C to the compound of Formula D may be carried out in a two-step process in which the ester is hydrolyzed to an acid by treatment with basic or acidic water in a suitable co-solvent. The resulting acid is then converted to the compound of Formula D by treatment with the appropriate amine in the presence of an amide coupling/dehydrating reagent such as 2,4,6-tripropyl-1,3,5,2,4,6-trioxatriphosphinane 2,4,6-trioxide (T3P), O-(7-azabenzotriazol-1-yl)-N,N,N',N'-tetramethyluronium hexafluorophosphate (HATU), 1,3-dicyclohexylcarbodiimide (DCC), etc., at temperatures ranging from −20° C. to 100° C. The intermediate of Formula D can then be transformed into the compound of Formula I through a Suzuki-Miyaura reaction (*Chemical Society Reviews* 2014, 43, 412-443; *Accounts of Chemical Research* 2013, 46, 2626-2634): treatment with an appropriate alkyl, aryl, or heteroaryl boronate in the presence of base, a transition metal catalyst [potentially palladium(II) acetate or tris (dibenzylideneacetone)dipalladium(0)], and a metal-chelating ligand (generally phosphine-based), in an appropriate solvent, installs the requisite $R^1$ moiety.

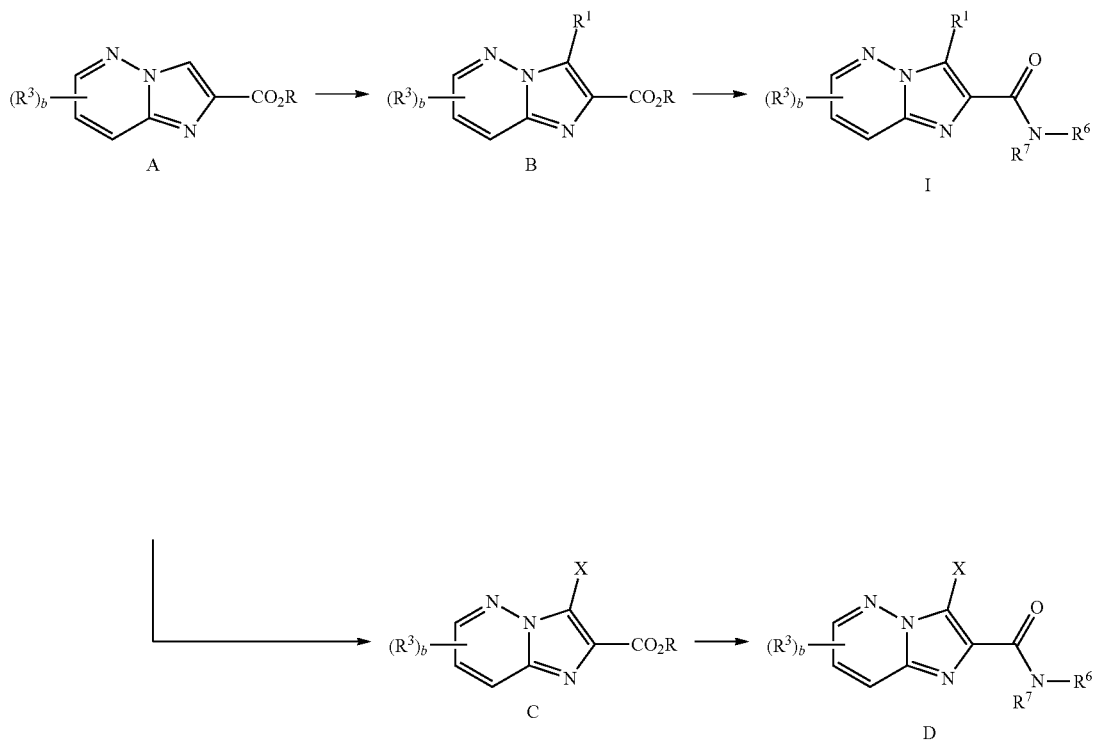

Scheme 1

EXPERIMENTAL PROCEDURES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

Example 1

Azetidin-1-yl[3-(4-chlorophenyl)imidazo[1,2-b]pyridazin-2-yl]methanone (1)

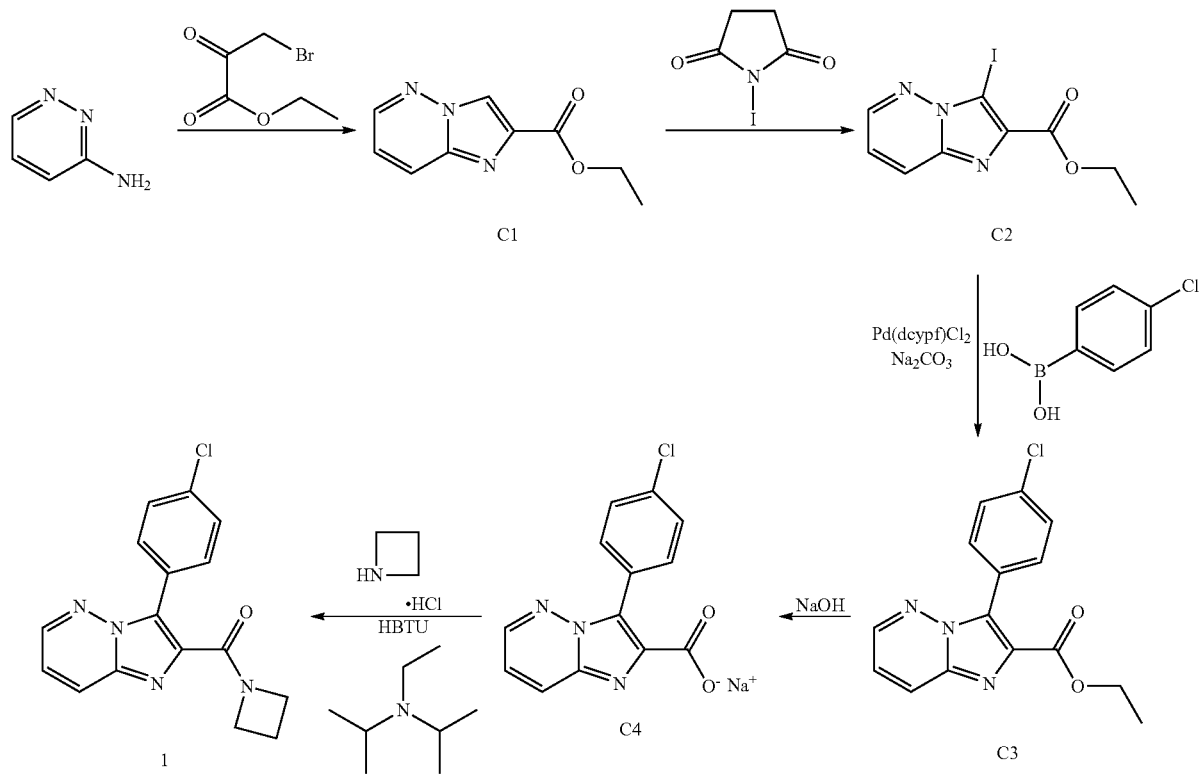

Step 1. Synthesis of ethyl imidazo[1,2-b]pyridazine-2-carboxylate (C1)

A mixture of pyridazin-3-amine (20 g, 210 mmol) and ethyl 3-bromo-2-oxopropanoate (82 g, 420 mmol) in ethanol (300 mL) was heated at reflux for 16 hours. After removal of solvent via distillation, the residue was taken up in 2 M hydrochloric acid (100 mL) and washed with ethyl acetate. The aqueous layer was basified to a pH of approximately 8 via addition of aqueous sodium bicarbonate solution and then extracted with chloroform; this organic layer was dried over sodium sulfate, filtered, and concentrated in vacuo. Silica gel chromatography (Eluent: 20% ethyl acetate in petroleum ether) afforded the product as a brown solid. Yield: 8.0 g, 42 mmol, 20%. LCMS m/z 192.0 [M+H]$^+$. $^1$H NMR (400 MHz, CDCl$_3$) δ 8.53 (s, 1H), 8.39 (dd, J=4.4, 1.6 Hz, 1H), 8.01-8.04 (m, 1H), 7.12 (dd, J=9.3, 4.4 Hz, 1H), 4.48 (q, J=7.1 Hz, 2H), 1.45 (t, J=7.1 Hz, 3H).

Step 2. Synthesis of ethyl 3-iodoimidazo[1,2-b]pyridazine-2-carboxylate (C2)

N-Iodosuccinimide (24.6 g, 109 mmol) was added to a solution of C1 (19 g, 99 mmol) in acetonitrile (250 mL), and the reaction mixture was stirred at room temperature for 24 hours. Additional N-iodosuccinimide (1 equivalent after every 24 hours) was introduced and stirring continued for a further 48 hours (72 hours overall), until complete consumption of starting material was indicated via thin layer chromatographic analysis. After removal of solvent in vacuo, the residue was taken up in dichloromethane and washed with 1 M hydrochloric acid and with water. The organic layer was dried over sodium sulfate, filtered, and concentrated under reduced pressure; silica gel chromatography (Eluent: 20% ethyl acetate in petroleum ether) provided the product as an off-white solid. Yield: 14.5 g, 45.7 mmol, 46%. LCMS m/z 318.0 [M+H]$^+$. $^1$H NMR (300 MHz, DMSO-d$_6$) δ 8.74 (dd, J=4.3, 1.3 Hz, 1H), 8.18 (dd, J=9.2, 1.4 Hz, 1H), 7.41 (dd, J=9.3, 4.4 Hz, 1H), 4.35 (q, J=7.0 Hz, 2H), 1.36 (t, J=7.1 Hz, 3H).

Step 3. Synthesis of ethyl 3-(4-chlorophenyl)imidazo[1,2-b]pyridazine-2-carboxylate (C3)

Aqueous sodium carbonate solution (3 M, 8.4 mL, 25 mmol) was added to a mixture of C2 (2.00 g, 6.31 mmol), (4-chlorophenyl)boronic acid (1.48 g, 9.46 mmol), and [1,1'-bis(dicyclohexylphosphino)ferrocene]dichloropalladium(II) (382 mg, 0.505 mmol) in 1,4-dioxane (32 mL). The reaction mixture was heated at 90° C. overnight, whereupon it was partitioned between ethyl acetate (150 mL) and water (50 mL). The aqueous layer was extracted with ethyl acetate (3×150 mL), and the combined organic layers were dried over magnesium sulfate, filtered, and concentrated in vacuo. Purification via silica gel chromatography (Gradient: 0% to 100% ethyl acetate in heptane) afforded the product. Yield: 1.25 g, 4.14 mmol, 66%. LCMS m/z 302.0, 304.0 [M+H]$^+$. $^1$H NMR (400 MHz, CDCl$_3$) δ 8.39 (dd, J=4.3, 1.5 Hz, 1H), 8.09 (dd, J=9.3, 1.5 Hz, 1H), 7.65 (br d, J=8.5 Hz, 2H), 7.50 (br d, J=8.5 Hz, 2H), 7.17 (dd, J=9.3, 4.3 Hz, 1H), 4.42 (q, J=7.1 Hz, 2H), 1.38 (t, J=7.1 Hz, 3H).

Step 4. Synthesis of 3-(4-chlorophenyl)imidazo[1,2-b]pyridazine-2-carboxylic Acid, Sodium Salt (C4)

A solution of C3 (1.75 g, 5.80 mmol) in methanol (25 mL) and tetrahydrofuran (25 mL) was added to an aqueous solution of sodium hydroxide (2 M, 25 mL), and the reaction mixture was stirred at room temperature for 4 hours. The resulting solid was collected via filtration and washed with cold water (2×25 mL) to provide the product as a solid. Yield: 1.50 g, 5.07 mmol, 87%. LCMS m/z 274.0, 276.0 [M+H]+.

Step 5. Synthesis of azetidin-1-yl[3-(4-chlorophenyl)imidazo[1,2-b]pyridazin-2-yl]methanone (1)

Compound C4 (1.40 g, 4.74 mmol) was combined with O-(benzotriazol-1-yl)-N,N,N',N'-tetramethyluronium hexafluorophosphate (HBTU, 2.92 g, 7.70 mmol) and N,N-diisopropylethylamine (3.56 mL, 20.4 mmol) in N,N-dimethylformamide (75 mL). After 2 minutes, azetidine hydrochloride (957 mg, 10.2 mmol) was added, and the reaction mixture was stirred at 50° C. overnight. After removal of solvent in vacuo, the residue was subjected to chromatography on silica gel (Gradient: 0% to 100% ethyl acetate in heptane) followed by trituration with ethyl acetate (30 mL) at 50° C.; this mixture was cooled to 0° C. and filtered. The collected solid was washed with diethyl ether (50 mL) and with cold ethyl acetate (15 mL). Subsequent recrystallization from ethyl acetate provided the product as an off-white solid. Yield: 980 mg, 3.13 mmol, 66%. LCMS m/z 313.2, 315.2 [M+H]+. 1H NMR (400 MHz, CDCl3) δ 8.41 (dd, J=4.4, 1.6 Hz, 1H), 8.10 (br d, J=9.2 Hz, 1H), 7.75 (br d, J=8.6 Hz, 2H), 7.48 (br d, J=8.6 Hz, 2H), 7.19 (dd, J=9.2, 4.3 Hz, 1H), 4.46-4.57 (m, 2H), 4.17-4.28 (m, 2H), 2.28-2.39 (m, 2H).

Example 2

3-(4-Chlorophenyl)-N-cyclopropylimidazo[1,2-b]pyridazine-2-carboxamide (2)

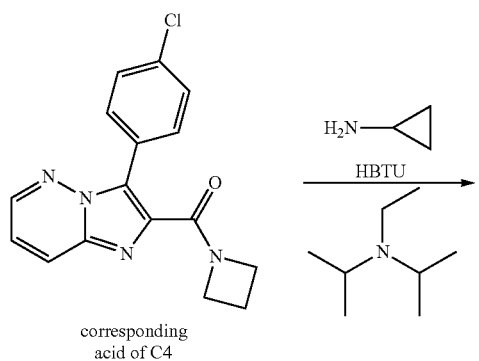

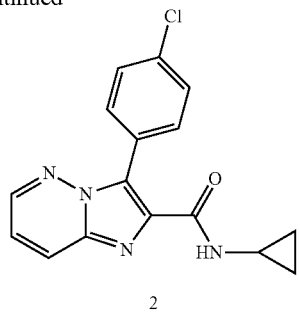

O-Benzotriazol-1-yl-N,N,N',N'-tetramethyluronium hexafluorophosphate (97%, 3.21 g, 8.21 mmol) was added to a mixture of the carboxylic acid of C4 (prepared in the same manner as C4, but in this case acidified with hydrochloric acid, to afford the carboxylic acid rather than the sodium salt) (1.50 g, 5.48 mmol) and N,N-diisopropylethylamine (2.86 mL, 16.4 mmol) in tetrahydrofuran (100 mL), and the reaction mixture was stirred at room temperature for 2 minutes. Cyclopropylamine (0.77 mL, 11 mmol) was introduced, and stirring was continued at room temperature overnight. The reaction mixture was concentrated in vacuo and the residue was subjected to silica gel chromatography (Gradient: 0% to 100% ethyl acetate in heptane). The resulting solid was triturated with a 10:1 mixture of diethyl ether and dichloromethane, and subsequently purified once more via chromatography on silica gel (Gradient: 0% to 100% ethyl acetate in heptane) to afford the product as a solid. Yield: 1.39 g, 4.44 mmol, 81%. LCMS m/z 313.3, 315.2 [M+H]+. 1H NMR (400 MHz, CD3OD) δ 8.46 (dd, J=4.3, 1.6 Hz, 1H), 8.06 (dd, J=9.3, 1.7 Hz, 1H), 7.71 (br d, J=8.7 Hz, 2H), 7.48 (br d, J=8.6 Hz, 2H), 7.31 (dd, J=9.3, 4.4 Hz, 1H), 2.79-2.86 (m, 1H), 0.78-0.84 (m, 2H), 0.62-0.68 (m, 2H).

Example 3

Azetidin-1-yl[3-(3,5-difluoro-4-methoxyphenyl)imidazo[1,2-b]pyridazin-2-yl]methanone

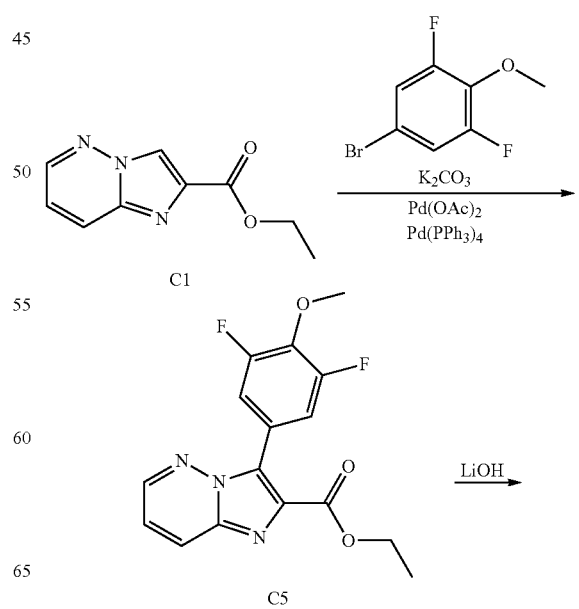

-continued

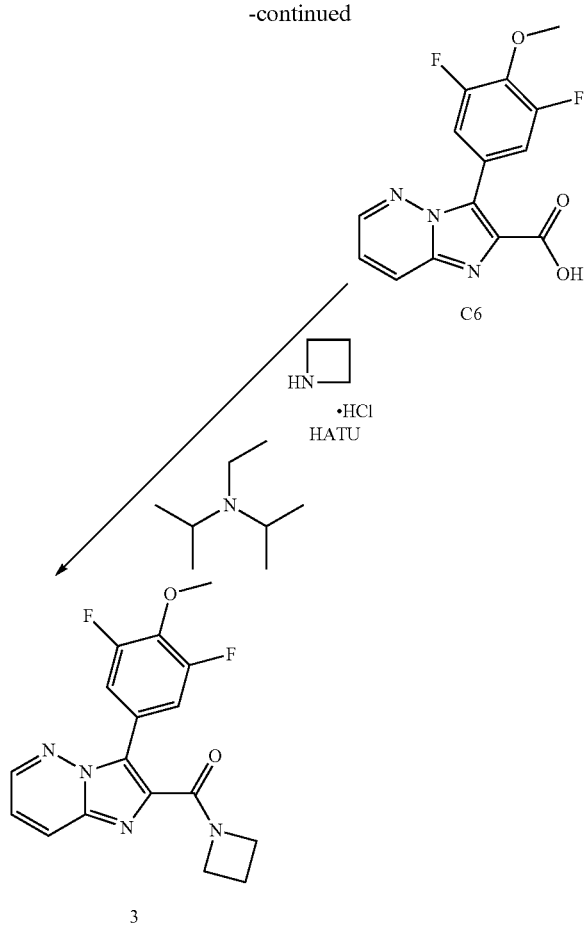

Step 1. Synthesis of ethyl 3-(3,5-difluoro-4-methoxyphenyl)imidazo[1,2-b]pyridazine-2-carboxylate (C5)

A mixture of C1 (500 mg, 2.6 mmol), 5-bromo-1,3-difluoro-2-methoxybenzene (864 mg, 3.87 mmol), and potassium carbonate (866 mg, 6.27 mmol) in N,N-dimethylformamide (10 mL) was degassed with nitrogen several times. Palladium(II) acetate (50 mg, 0.22 mmol) and tetrakis(triphenylphosphine)palladium(0) (30 mg, 26 µmol) were added, and the reaction mixture was stirred at 110° C. overnight. After addition of water (50 mL), the mixture was extracted with ethyl acetate (3×30 mL); the combined organic layers were concentrated in vacuo and purified by chromatography on silica gel to provide the product as a yellow solid. Yield: 500 mg, 1.5 mmol, 58%. LCMS m/z 334.0 [M+H]$^+$.

Step 2. Synthesis of 3-(3,5-difluoro-4-methoxyphenyl)imidazo[1,2-b]pyridazine-2-carboxylic Acid (C6)

To a solution of C5 (500 mg, 1.5 mmol) in ethanol (30 mL) was added a solution of lithium hydroxide (2 equivalents) in water (10 mL), and the reaction mixture was stirred at room temperature for 4 hours, whereupon it was concentrated in vacuo. The residue was diluted with water and acidified to a pH of 4 with hydrochloric acid. After extraction of the mixture with dichloromethane (3×30 mL), the combined organic layers were concentrated under reduced pressure to afford the product as a yellow solid, which was used in the next step without additional purification. Yield: 500 mg, quantitative. LCMS m/z 305.9 [M+H]$^+$.

Step 3. Synthesis of azetidin-1-yl[3-(3,5-difluoro-4-methoxyphenyl)imidazo[1,2-b]pyridazin-2-yl]methanone (3)

A mixture of C6 (100 mg, 0.328 mmol), azetidine hydrochloride (45 mg, 0.48 mmol), O-(7-azabenzotriazol-1-yl)-N,N,N',N'-tetramethyluronium hexafluorophosphate (HATU, 186 mg, 0.489 mmol), N,N-diisopropylethylamine (126 mg, 0.975 mmol) and N,N-dimethylformamide (10 mL) was stirred at room temperature overnight. The reaction mixture was then diluted with water and extracted with ethyl acetate (3×10 mL). The combined organic layers were concentrated in vacuo and purified by reversed phase HPLC (Column: Phenomenex Synergi C18, 4 µm; Mobile phase A: 0.225% formic acid in water; Mobile phase B: acetonitrile; Gradient: 33% to 53% B) to provide the product as a yellow solid. Yield: 35.7 mg, 0.104 mmol, 32%. LCMS m/z 344.9 [M+H]$^+$. $^1$H NMR (400 MHz, DMSO-d$_6$) δ 8.63 (dd, J=4.4, 1.6 Hz, 1H), 8.24 (dd, J=9.3, 1.6 Hz, 1H), 7.56 (br d, J=9.9 Hz, 2H), 7.39 (dd, J=9.4, 4.4 Hz, 1H), 4.46-4.53 (m, 2H), 4.01-4.07 (m, 2H), 4.01 (br s, 3H), 2.22-2.32 (m, 2H).

Example 4

N-Cyclopropyl-3-(2-methoxypyrimidin-5-yl)imidazo[1,2-b]pyridazine-2-carboxamide (4)

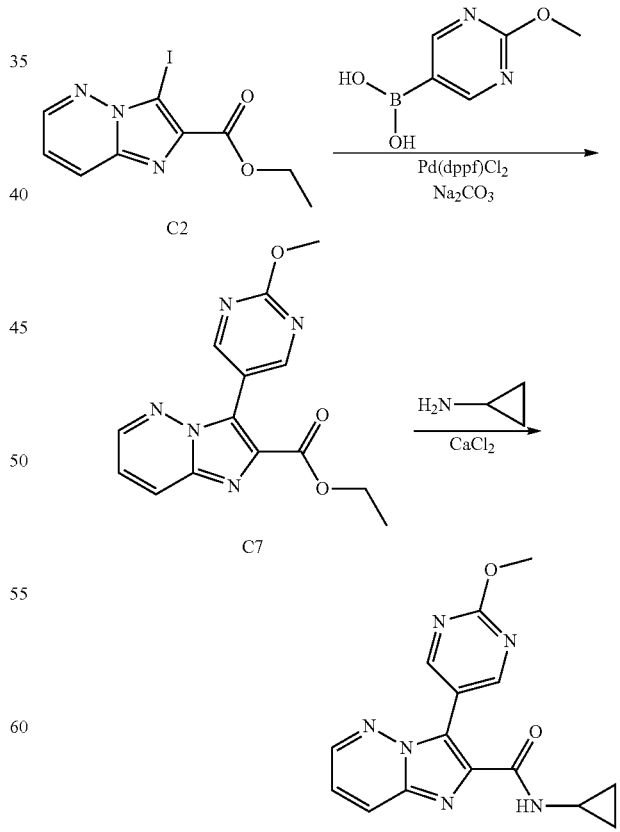

Step 1. Synthesis of ethyl 3-(2-methoxypyrimidin-5-yl)imidazo[1,2-b]pyridazine-2-carboxylate (C7)

A mixture of C2 (1.8 g, 5.7 mmol), (2-methoxypyrimidin-5-yl)boronic acid (1.3 g, 8.4 mmol), sodium carbonate (1.8 g, 17 mmol) and 1,4-dioxane (30 mL) was degassed several times with nitrogen. [1,1'-Bis(diphenylphosphino)ferrocene]dichloropalladium(II) (30 mg, 40 µmol) was added, and the reaction mixture was stirred at 110° C. overnight. It was then diluted with water and extracted with ethyl acetate (4×100 mL); the combined organic layers were washed with saturated aqueous sodium chloride solution, dried over sodium sulfate, filtered, and concentrated under reduced pressure. Purification via chromatography on silica gel provided the product as a yellow solid. Yield: 800 mg, 2.7 mmol, 47%. LCMS m/z 299.7 [M+H]+.

Step 2. Synthesis of N-cyclopropyl-3-(2-methoxypyrimidin-5-yl)imidazo[1,2-b]pyridazine-2-carboxamide (4)

Cyclopropylamine (5 mL, 70 mmol) was added to a mixture of C7 (800 mg, 2.7 mmol) and calcium chloride (200 mg, 1.8 mmol) in methanol (200 mL). The reaction mixture was stirred at 50° C. for 5 hours, whereupon it was diluted with water and extracted with ethyl acetate (2×100 mL). The combined organic layers were washed with saturated aqueous sodium chloride solution, dried over sodium sulfate, filtered, and concentrated in vacuo. Purification via reversed phase HPLC (Column: Agella Venusil ASB C18, 5 µm; Mobile phase A: 0.225% formic acid in water; Mobile phase B: acetonitrile; Gradient: 29% to 49% B) afforded the product as a white solid. Yield: 430.3 mg, 1.39 mmol, 51%. LCMS m/z 311.0 [M+H]+. 1H NMR (400 MHz, CDCl3) δ 9.01 (s, 2H), 8.40 (dd, J=4.4, 1.6 Hz, 1H), 7.97 (dd, J=9.2, 1.7 Hz, 1H), 7.60 (br s, 1H), 7.20 (dd, J=9.3, 4.3 Hz, 1H), 4.10 (s, 3H), 2.88-2.95 (m, 1H), 0.84-0.91 (m, 2H), 0.66-0.72 (m, 2H).

Example 5

3-(6-Cyanopyridin-3-yl)-N-cyclopropylimidazo[1,2-b]pyridazine-2-carboxamide (5)

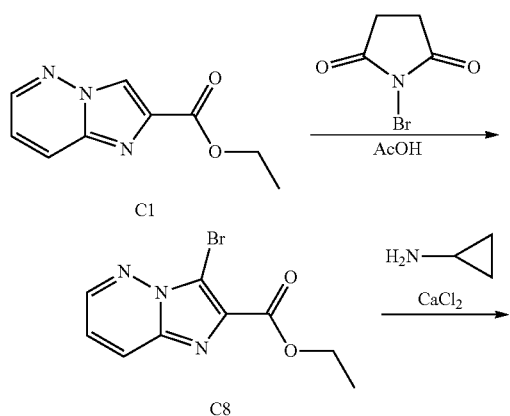

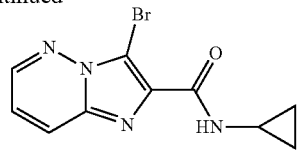

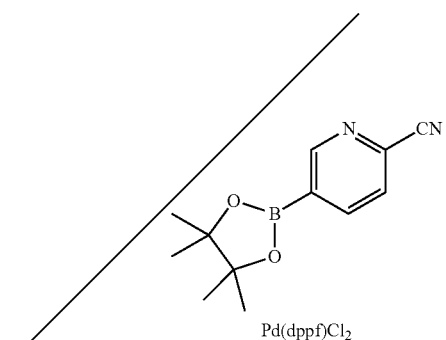

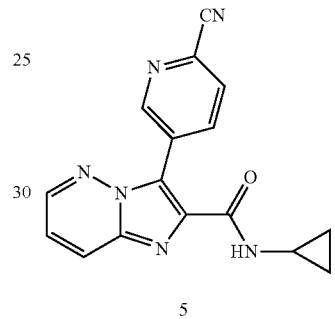

Step 1. Synthesis of ethyl 3-bromoimidazo[1,2-b]pyridazine-2-carboxylate (C8)

N-Bromosuccinimide (25.6 g, 144 mmol) was added to a 0° C. solution of C1 (25.0 g, 131 mmol) in dichloromethane (250 mL). The reaction mixture was allowed to gradually warm to room temperature and stir overnight, whereupon the reaction was quenched with 10% aqueous sodium bisulfite solution. The resulting mixture was diluted with additional dichloromethane and washed with saturated aqueous sodium bicarbonate solution and with water. The organic layer was dried over magnesium sulfate, filtered, and concentrated in vacuo. Trituration with tert-butyl methyl ether afforded the product as a pinkish-mauve solid (25.4 g). Concentration of the filtrate under reduced pressure was followed by trituration with tert-butyl methyl ether and hexanes to give a second batch of product (6.46 g). Combined yield: 31.9 g, 118 mmol, 90%. LCMS m/z 270.0, 272.0 [M+H]+. 1H NMR (400 MHz, CDCl3) δ 8.55 (dd, J=4.4, 1.6 Hz, 1H), 8.05 (dd, J=9.3, 1.6 Hz, 1H), 7.22 (dd, J=9.3, 4.4 Hz, 1H), 4.53 (q, J=7.1 Hz, 2H), 1.49 (t, J=7.1 Hz, 3H).

Step 2. Synthesis of 3-bromo-N-cyclopropylimidazo[1,2-b]pyridazine-2-carboxamide (C9)

A mixture of C8 (27.0 g, 100 mmol), cyclopropylamine (25.0 mL, 349 mmol), and calcium chloride (12.2 g, 110 mmol) in methanol (250 mL) was heated at 50° C. for 3 days, whereupon it was cooled to room temperature and concentrated in vacuo. The residue was partitioned between dichloromethane and water, and the organic layer was concentrated under reduced pressure. Trituration of the residue with diethyl ether and water afforded the product as a pink solid. Yield: 24.4 g, 86.8 mmol, 87%. LCMS m/z 281.0, 283.0 [M+H]$^+$. $^1$H NMR (400 MHz, CDCl$_3$) δ 8.52 (dd, J=4.4, 1.6 Hz, 1H), 7.90 (dd, J=9.3, 1.6 Hz, 1H), 7.46 (br s, 1H), 7.20 (dd, J=9.2, 4.4 Hz, 1H), 2.91-2.98 (m, 1H), 0.86-0.92 (m, 2H), 0.67-0.72 (m, 2H).

Step 3. Synthesis of 3-(6-cyanopyridin-3-yl)-N-cyclopropylimidazo[1,2-b]pyridazine-2-carboxamide (5)

To a degassed solution of C9 (300 mg, 1.07 mmol) in 2-methyltetrahydrofuran (7 mL) and water (2 mL) was added potassium phosphate (80%, 849 mg, 3.20 mmol). The mixture was heated to 80° C., and then treated with [1,1'-bis(diphenylphosphino)ferrocene]dichloropalladium(II), dichloromethane complex (97%, 53.9 mg, 64.0 μmol). After 2 minutes, 5-(4,4,5,5-tetramethyl-1,3,2-dioxaborolan-2-yl)pyridine-2-carbonitrile (319 mg, 1.39 mmol) was added, and the reaction mixture was maintained at 80° C. overnight. It was then allowed to cool to room temperature and was filtered through diatomaceous earth; the filter pad was rinsed with ethyl acetate, and the combined filtrates were washed with water. After the organic layer had been concentrated in vacuo, the residue was purified via silica gel chromatography (Gradient: 50% to 100% ethyl acetate in heptane) to afford a white solid (196 mg). Recrystallization from methanol afforded the product as colorless needles. Yield: 135 mg, 0.444 mmol, 41%. LCMS m/z 305.1 [M+H]$^+$. $^1$H NMR (400 MHz, CDCl$_3$) δ 9.18 (d, J=1.5 Hz, 1H), 8.41-8.46 (m, 2H), 8.01 (dd, J=9.2, 1.4 Hz, 1H), 7.82 (d, J=8.0 Hz, 1H), 7.66 (br s, 1H), 7.26 (dd, J=9.2, 4.4 Hz, 1H), 2.86-2.94 (m, 1H), 0.85-0.92 (m, 2H), 0.66-0.72 (m, 2H).

Example 6

N-Cyclopropyl-3-([1,2,4]triazolo[1,5-a]pyridin-6-yl)imidazo[1,2-b]pyridazine-2-carboxamide (6)

Compound C9 (1.90 g, 6.76 mmol) was combined with 6-(4,4,5,5-tetramethyl-1,3,2-dioxaborolan-2-yl)[1,2,4]triazolo[1,5-a]pyridine (1.82 g, 7.43 mmol), [1,1'-bis(dicyclohexylphosphino)ferrocene]dichloropalladium(II) (51.4 mg, 68.0 μmol), and 1,4-dioxane (34 mL). Aqueous sodium carbonate solution (3 M, 9.0 mL, 27 mmol) was added, and the reaction mixture was purged with nitrogen for 15 minutes, then heated at 100° C. for 20 hours. The reaction mixture was cooled to room temperature and the supernatant was immediately filtered through a pad of diatomaceous earth, rinsing with 10% methanol in ethyl acetate. Remaining solids were partitioned between half-saturated aqueous sodium chloride solution (25 mL) and 10% methanol in ethyl acetate by stirring for 5 minutes; this mixture was also filtered through diatomaceous earth. The combined filtrates were diluted with saturated aqueous sodium chloride solution (25 mL) and additional 10% methanol in ethyl acetate. The aqueous layer was extracted three times with 10% methanol in ethyl acetate, and the combined organic layers were washed with saturated aqueous sodium chloride solution, dried over sodium sulfate, filtered, and concentrated in vacuo. The residue was adsorbed onto diatomaceous earth (4-fold the weight of the crude product) using dichloromethane and methanol, and subjected to chromatography on silica gel (Gradient: 0% to 20% methanol in ethyl acetate). The resulting material (1.83 g) was mixed with methanol (20 mL) and heated to 72° C. for 20 minutes; after cooling, the mixture was filtered and washed with methanol to afford the product as an off-white solid. This material was found to be crystalline via powder X-ray diffraction. Yield: 1.66 g, 5.20 mmol, 77%. LCMS m/z 320.2 [M+H]$^+$. $^1$H NMR (400 MHz, DMSO-d$_6$) δ 9.35 (dd, J=1.4, 1.3 Hz, 1H), 8.64 (dd, J=4.4, 1.6 Hz, 1H), 8.61 (br d, J=5 Hz, 1H), 8.60 (s, 1H), 8.24 (dd, J=9.3, 1.6 Hz, 1H), 7.93-7.99 (m, 2H), 7.44 (dd, J=9.3, 4.4 Hz, 1H), 2.82-2.90 (m, 1H), 0.64-0.70 (m, 4H).

Example 7

3-(4-Chloro-3-fluorophenyl)-N-(1-methyl-1H-pyrazol-4-yl)imidazo[1,2-b]pyridazine-2-carboxamide (7)

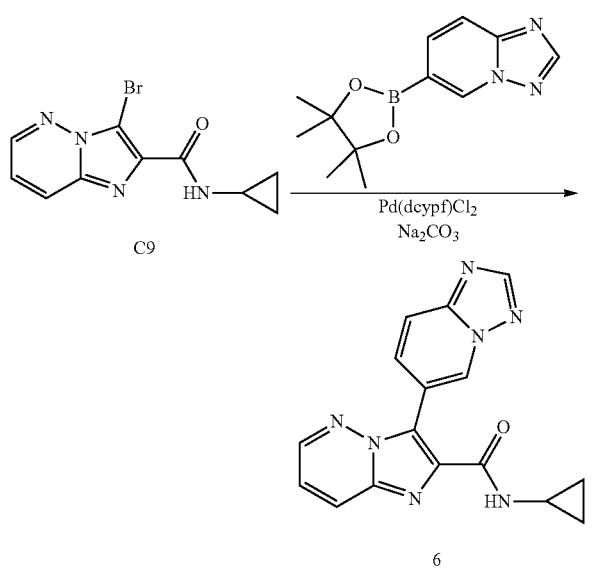

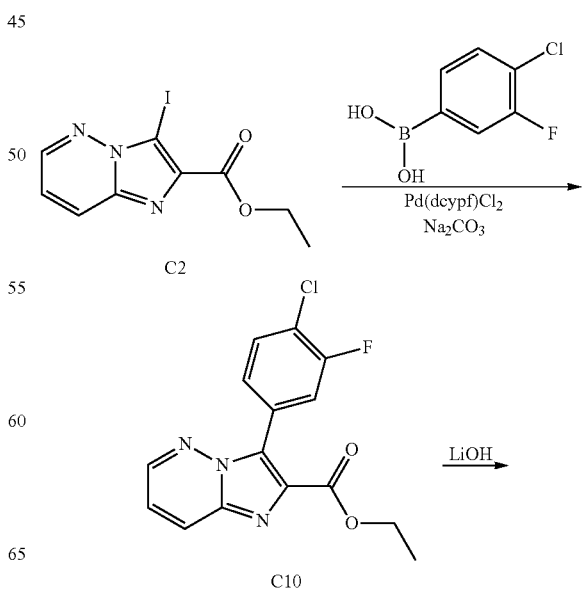

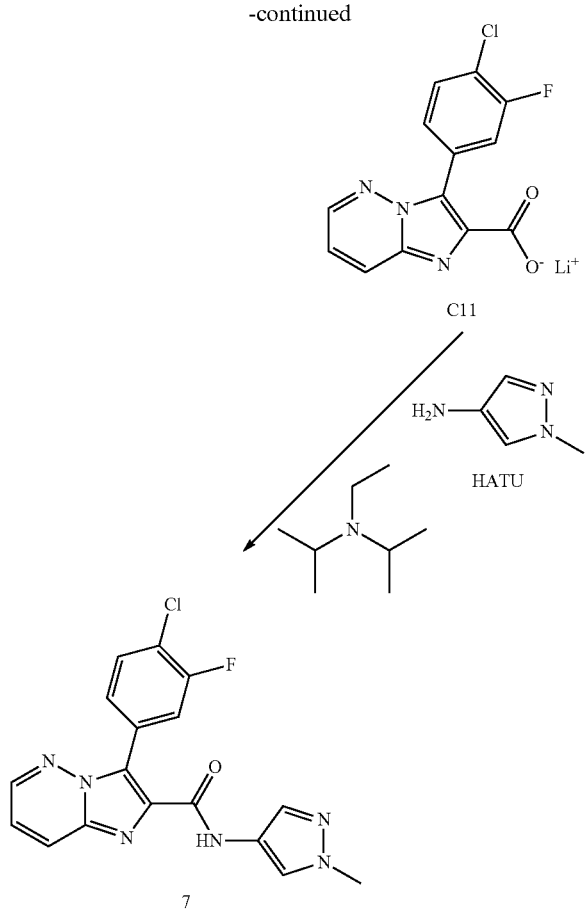

Step 1. Synthesis of ethyl 3-(4-chloro-3-fluorophenyl)imidazo[1,2-b]pyridazine-2-carboxylate (C10)

Aqueous sodium carbonate solution (3 M, 8.8 mL, 26 mmol) was added to a mixture of C2 (2.10 g, 6.62 mmol), (4-chloro-3-fluorophenyl)boronic acid (1.73 g, 9.92 mmol), and [1,1'-bis(dicyclohexylphosphino)ferrocene]dichloropalladium(II) (401 mg, 0.530 mmol) in 1,4-dioxane (34 mL), and the reaction mixture was heated at 85° C. overnight. It was then diluted with water (75 mL) and extracted with ethyl acetate (4×250 mL). The combined organic layers were dried over magnesium sulfate, filtered, and concentrated in vacuo; purification via chromatography on silica gel (Gradient: 5% to 100% ethyl acetate in heptane) afforded the product. Yield: 1.50 g, 4.69 mmol, 71%. LCMS m/z 320.0, 322.0 [M+H]$^+$. $^1$H NMR (400 MHz, CDCl$_3$) δ 8.43 (br d, J=4.3 Hz, 1H), 8.11 (br d, J=9.3 Hz, 1H), 7.52-7.58 (m, 2H), 7.46-7.50 (m, 1H), 7.22 (dd, J=9.3, 4.4 Hz, 1H), 4.44 (q, J=7.1 Hz, 2H), 1.39 (t, J=7.1 Hz, 3H).

Step 2. Synthesis of 3-(4-chloro-3-fluorophenyl)imidazo[1,2-b]pyridazine-2-carboxylic Acid, Lithium Salt (C11)

A mixture of C10 (700 mg, 2.2 mmol) and lithium hydroxide monohydrate (200 mg, 4.8 mmol) in methanol (100 mL) and water (30 mL) was stirred at room temperature for 16 hours. The reaction mixture was concentrated to remove methanol, and the residue was washed with ethyl acetate. Collection of the resulting solid via filtration afforded the product as a yellow solid. Yield: 700 mg, quantitative. $^1$H NMR (400 MHz, DMSO-d$_6$) δ 8.56 (br d, J=4 Hz, 1H), 8.13 (br d, J=9 Hz, 1H), 7.97 (d, J=11 Hz, 1H), 7.79 (d, J=8 Hz, 1H), 7.65 (dd, J=8.5, 8 Hz, 1H), 7.32 (dd, J=9.3, 4.3 Hz, 1H).

Step 3. Synthesis of 3-(4-chloro-3-fluorophenyl)-N-(1-methyl-1H-pyrazol-4-yl)imidazo[1,2-b]pyridazine-2-carboxamide (7)

A mixture of C11 (200 mg, 0.67 mmol) and O-(7-azabenzotriazol-1-yl)-N,N,N',N'-tetramethyluronium hexafluorophosphate (500 mg, 1.3 mmol) in N,N-dimethylformamide (5 mL) and N,N-diisopropylethylamine (2 mL) was stirred at room temperature for 20 minutes. 1-Methyl-1H-pyrazol-4-amine (200 mg, 2.1 mmol) was added, and the reaction mixture was stirred at 35° C. for 2 hours, whereupon it was diluted with water and filtered. The collected solid was washed with ethyl acetate and methanol to provide the product as a pink solid. Yield: 130 mg, 0.351 mmol, 52%. LCMS m/z 393.0 [M+Na$^+$]. $^1$H NMR (400 MHz, DMSO-d$_6$) δ 10.76 (s, 1H), 8.64 (br d, J=4.4 Hz, 1H), 8.26 (br d, J=9.4 Hz, 1H), 8.04 (s, 1H), 7.82 (br d, J=10.7 Hz, 1H), 7.73 (dd, J=8.3, 8.0 Hz, 1H), 7.66 (s, 1H), 7.61 (br d, J=8.4 Hz, 1H), 7.44 (dd, J=9.3, 4.3 Hz, 1H), 3.79 (s, 3H).

Example 8

Azetidin-1-yl[3-(pyrazolo[1,5-a]pyridin-6-yl)imidazo[,2-b]pyridazin-2-yl]methanone (8)

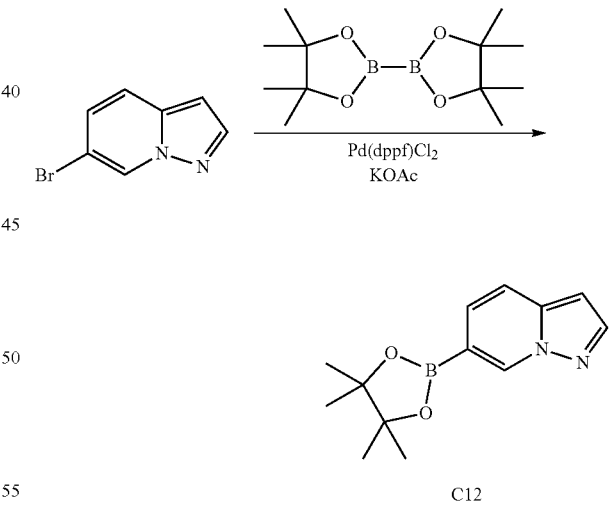

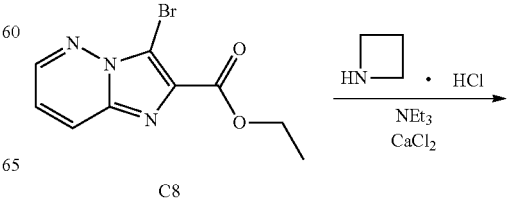

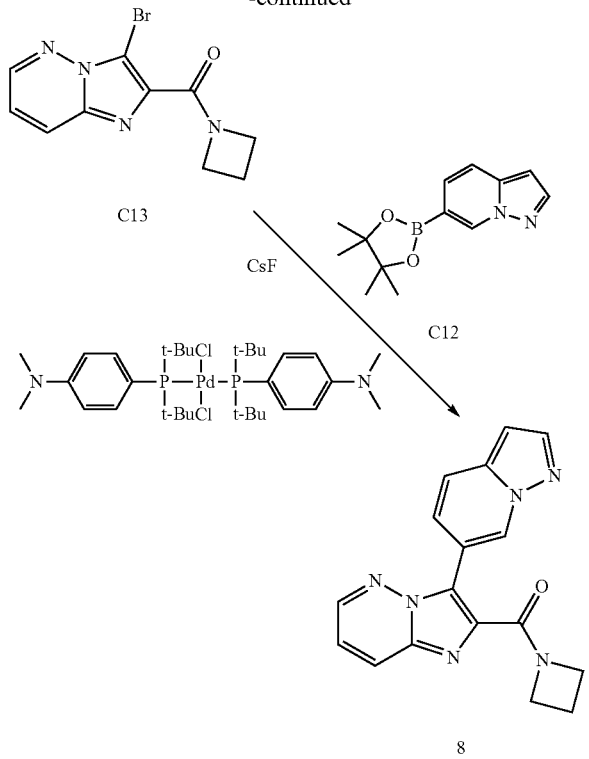

Step 1. Synthesis of 6-(4,4,5,5-tetramethyl-1,3,2-dioxaborolan-2-yl)pyrazolo[1,5-a]pyridine (C12)

A mixture of 6-bromopyrazolo[1,5-a]pyridine (1.5 g, 7.6 mmol), 4,4,4',4',5,5,5',5'-octamethyl-2,2'-bi-1,3,2-dioxaborolane (2.03 g, 7.99 mmol), [1,1'-bis(diphenylphosphino)ferrocene]dichloropalladium(II) (0.27 g, 0.37 mmol), and potassium acetate (2.2 g, 22 mmol) in 1,4-dioxane (25 mL) was degassed for 10 minutes, and then heated at 100° C. overnight. After removal of solvent in vacuo, the residue was diluted with dichloromethane, mixed with diatomaceous earth (~5 g), and concentrated under reduced pressure. Silica gel chromatography (Gradient: 0% to 50% ethyl acetate in heptane) afforded the product as a green liquid. Yield: 1.35 g, 5.53 mmol, 73%. GCMS m/z 244 [M+]. $^1$H NMR (400 MHz, CDCl$_3$) δ 8.86-8.87 (m, 1H), 7.99 (d, J=2.2 Hz, 1H), 7.50 (dd, J=8.8, 1.1 Hz, 1H), 7.37 (dd, J=8.8, 1.1 Hz, 1H), 6.49 (dd, J=2.2, 0.9 Hz, 1H), 1.37 (s, 12H).

Step 2. Synthesis of azetidin-1-yl(3-bromoimidazo[1,2-b]pyridazin-2-yl)methanone (C13)

A mixture of azetidine hydrochloride (1.73 g, 18.5 mmol) and triethylamine (2.57 mL, 18.5 mmol) in anhydrous methanol (18 mL) was stirred at room temperature for 10 minutes. Compound C8 (500 mg, 1.85 mmol) and calcium chloride (206 mg, 1.86 mmol) were added, the reaction vessel was tightly capped, and the reaction mixture was heated at 50° C. overnight. After removal of solvent in vacuo, the residue was partitioned between water (25 mL) and dichloromethane (100 mL). The organic layer was dried over magnesium sulfate, filtered, and concentrated under reduced pressure; chromatography on silica gel (Eluent: ethyl acetate) afforded the product as a light yellow solid. Yield: 357 mg, 1.27 mmol, 69%. LCMS m/z 281.0, 283.0 [M+H]+. $^1$H NMR (400 MHz, CDCl$_3$) δ 8.45 (dd, J=4.4, 1.6 Hz, 1H), 7.87 (dd, J=9.2, 1.6 Hz, 1H), 7.12 (dd, J=9.2, 4.4 Hz, 1H), 4.59-4.65 (m, 2H), 4.17-4.24 (m, 2H), 2.27-2.37 (m, 2H).

Step 3. Synthesis of azetidin-1-yl[3-(pyrazolo[1,5-a]pyridin-6-yl)imidazo[1,2-b]pyridazin-2-yl]methanone (8)

A flask containing a solution of C13 (1.06 g, 3.77 mmol) in toluene (60 mL) was evacuated under high vacuum and then filled with nitrogen. Repeating the evacuation/nitrogen fill after each addition, C12 (2.84 g, 11.6 mmol) was added, followed by a solution of cesium fluoride (2.87 g, 18.9 mmol) in water (18 mL), and a solution of bis[di-tert-butyl(4-dimethylaminophenyl)phosphine]dichloropalladium(II) (335 mg, 0.473 mmol) in 1,2-dichloroethane (9 mL). The reaction mixture was heated at 100° C. for 23 hours, whereupon it was cooled to room temperature, concentrated in vacuo, and subjected to chromatography on silica gel (Eluents: ethyl acetate, then 5% methanol in dichloromethane). This material was combined with the product from a similar reaction carried out on C13 (200 mg, 0.71 mmol) and purified via supercritical fluid chromatography (Column: Princeton Methanesulfonamide, 5 μm; Mobile phase: 4:1 carbon dioxide/methanol). The resulting material was recrystallized from ethanol to afford the product as a white solid. This material was found to be crystalline via powder X-ray diffraction. Yield: 540 mg, 1.7 mmol, 38%. LCMS m/z 319.1 [M+H]+. $^1$H NMR (400 MHz, CDCl$_3$) δ 9.07 (br s, 1H), 8.40 (dd, J=4.3, 1.6 Hz, 1H), 8.01 (d, J=2.2 Hz, 1H), 8.01 (dd, J=9.3, 1.7 Hz, 1H), 7.63 (d, half of AB quartet, J=9.3 Hz, 1H), 7.54 (dd, half of ABX pattern, J=9.2, 1.4 Hz, 1H), 7.16 (dd, J=9.3, 4.4 Hz, 1H), 6.56 (d, J=2.2 Hz, 1H), 4.59-4.65 (m, 2H), 4.20-4.27 (m, 2H), 2.31-2.40 (m, 2H).

Example 9

3-(4-Chloro-2,5-difluorophenyl)-N-cyclopropylimidazo[1,2-b]pyridazine-2-carboxamide (9)

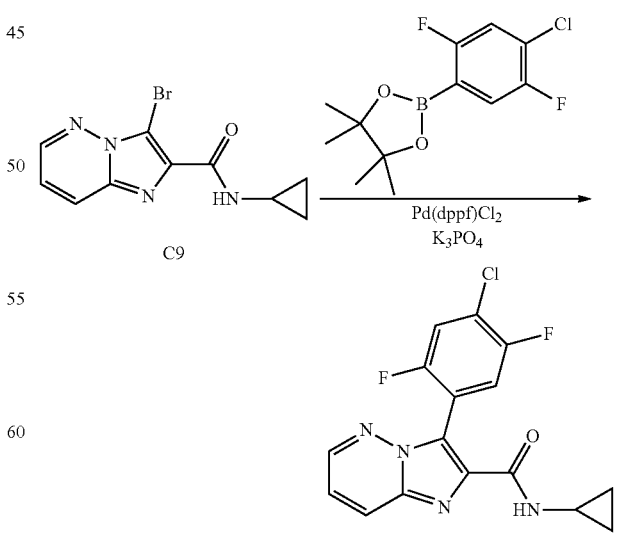

Potassium phosphate (80%, 1.42 g, 5.35 mmol) was added to a degassed solution of C9 (500 mg, 1.78 mmol) in 2-methyltetrahydrofuran (20 mL) and water (5 mL), and the mixture was heated to 80° C. [1,1'-Bis(diphenylphosphino)ferrocene]dichloropalladium (I), dichloromethane complex (97%, 90.1 mg, 0.107 mmol) was introduced, and after 2 minutes, 2-(4-chloro-2,5-difluorophenyl)-4,4,5,5-tetramethyl-1,3,2-dioxaborolane (635 mg, 2.31 mmol) was added. The reaction mixture was maintained at 80° C. overnight, whereupon it was cooled to room temperature and filtered through diatomaceous earth. The filter pad was rinsed with ethyl acetate, and the combined filtrates were washed with water; the organic layer was concentrated in vacuo and purified via silica gel chromatography (Gradient: 50% to 100% ethyl acetate in heptane). Recrystallization from methanol afforded the product as an off-white solid. Yield: 217 mg, 0.622 mmol, 35%. LCMS m/z 349.1, 351.1 [M+H]$^+$. $^1$H NMR (400 MHz, CDCl$_3$) δ 8.40 (dd, J=4.4, 1.7 Hz, 1H), 7.98 (dd, J=9.3, 1.6 Hz, 1H), 7.53 (br s, 1H), 7.50 (dd, J=8.9, 5.9 Hz, 1H), 7.31 (dd, J=8.6, 6.1 Hz, 1H), 7.21 (dd, J=9.3, 4.4 Hz, 1H), 2.86-2.93 (m, 1H), 0.84-0.89 (m, 2H), 0.66-0.71 (m, 2H).

Using the methodology described above for Examples 1-9, Examples 10-25 were synthesized. See Table 1 for specific methods employed, as well as characterization data for these Examples.

TABLE 1

| Example Number | Method of Synthesis: Example Number; Source of Non-commercial Starting Materials | Structure | $^1$H NMR (400 MHz, CDCl$_3$) δ (ppm); Mass spectrum, observed ion m/z [M + H]$^+$ or HPLC retention time; Mass spectrum m/z [M + H]$^+$ (unless otherwise indicated) |
|---|---|---|---|
| 10 | Example 1; C11 | 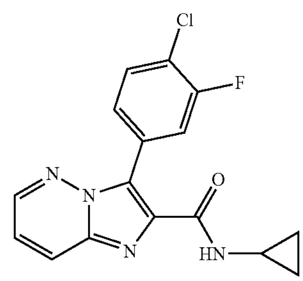 [SMILES: O=C(NC1CC1)c1nc2cccnn2c1-c1ccc(Cl)c(F)c1] | $^1$H NMR (400 MHz, CD$_3$OD) δ 8.48 (dd, J = 4.3, 1.4 Hz, 1H), 8.07 (dd, J = 9.3, 1.4 Hz, 1H), 7.64-7.69 (m, 1H), 7.53-7.59 (m, 2H), 7.33 (dd, J = 9.3, 4.4 Hz, 1H), 2.79-2.87 (m, 1H), 0.78-0.85 (m, 2H), 0.63-0.69 (m, 2H); 331.1, 333.1 |
| 11 | Example 4$^1$; C8 | 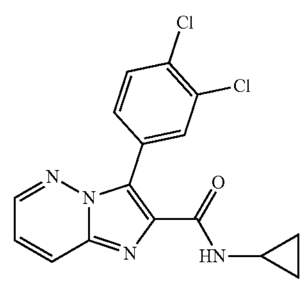 [SMILES: O=C(NC1CC1)c1nc2cccnn2c1-c1ccc(Cl)c(Cl)c1] | 8.40 (dd, J = 4.4, 1.6 Hz, 1H), 7.96 (dd, J = 9.3, 1.6 Hz, 1H), 7.93 (d, J = 1.9 Hz, 1H), 7.70 (dd, half of ABX pattern, J = 8.3, 2.1 Hz, 1H), 7.60 (br s, 1H), 7.58 (d, half of AB quartet, J = 8.4 Hz, 1H), 7.19 (dd, J = 9.3, 4.4 Hz, 1H), 2.86-2.94 (m, 1H), 0.83-0.90 (m, 2H), 0.64-0.71 (m, 2H); 346.9 |
| 12 | Example 5; C9 | 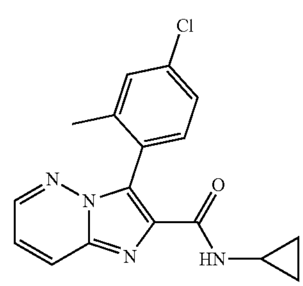 | $^1$H NMR (400 MHz, DMSO-d$_6$) δ 8.54 (dd, J = 4.4, 1.6 Hz, 1H), 8.48 (br d, J = 4.9 Hz, 1H), 8.19 (dd, J = 9.3, 1.6 Hz, 1H), 7.45-7.47 (m, 1H), 7.37 (dd, J = 9.3, 4.4 Hz, 1H), 7.33-7.35 (m, 2H), 2.76-2.84 (m, 1H), 1.99-2.00 (m, 3H), 0.62-0.65 (m, 4H); 327.1, 329.1 |
| 13 | Example 7; C11 | 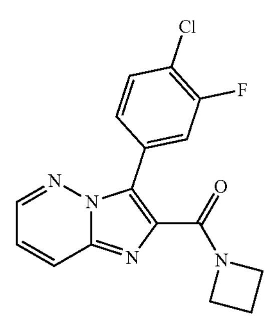 [SMILES: O=C(c1nc2cccnn2c1-c1ccc(Cl)c(F)c1)N1CCC1] | $^1$H NMR (400 MHz, DMSO-d$_6$) δ 8.62 (dd, J = 4.3, 1.5 Hz, 1H), 8.25 (dd, J = 9.3, 1.5 Hz, 1H), 7.81 (dd, J = 10.8, 1.9 Hz, 1H), 7.71 (dd, J = 8.3, 8.0 Hz, 1H), 7.59 (br dd, J = 8.3, 1.4 Hz, 1H), 7.39 (dd, J = 9.3, 4.4 Hz, 1H), 4.47-4.53 (m, 2H), 4.00-4.07 (m, 2H), 2.21-2.32 (m, 2H); 330.8 |

TABLE 1-continued

| Example Number | Method of Synthesis: Example Number; Source of Non-commercial Starting Materials | Structure | $^1$H NMR (400 MHz, CDCl$_3$) δ (ppm); Mass spectrum, observed ion m/z [M + H]$^+$ or HPLC retention time; Mass spectrum m/z [M + H]$^+$ (unless otherwise indicated) |
|---|---|---|---|
| 14 | Example 4[2]; C1 | 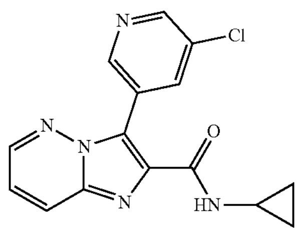 [SMILES: O=C(NC1CC1)c1nc2cccnn2c1-c1cncc(Cl)c1] | $^1$H NMR (400 MHz, DMSO-d$_6$) δ 8.85 (d, J = 1.6 Hz, 1H), 8.70 (d, J = 2.4 Hz, 1H), 8.64 (dd, J = 4.4, 1.5 Hz, 1H), 8.62 (br d, J = 4.6 Hz, 1H), 8.30 (dd, J = 2.1, 2.0 Hz, 1H), 8.23 (dd, J = 9.3, 1.5 Hz, 1H), 7.44 (dd, J = 9.3, 4.4 Hz, 1H), 2.81-2.90 (m, 1H), 0.63-0.70 (m, 4H); 313.9 |
| 15 | Example 3; C1 | 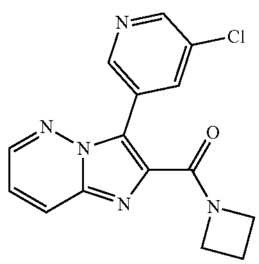 [SMILES: O=C(c1nc2cccnn2c1-c1cncc(Cl)c1)N1CCC1] | $^1$H NMR (400 MHz, DMSO-d$_6$) δ 8.83 (d, J = 1.9 Hz, 1H), 8.68 (d, J = 2.4 Hz, 1H), 8.64 (dd, J = 4.4, 1.5 Hz, 1H), 8.30 (dd, J = 2.4, 1.9 Hz, 1H), 8.28 (dd, J = 9.3, 1.5 Hz, 1H), 7.42 (dd, J = 9.3, 4.4 Hz, 1H), 4.57-4.62 (m, 2H), 4.02-4.08 (m, 2H), 2.24-2.33 (m, 2H); 313.9 |
| 16 | C1[3] | 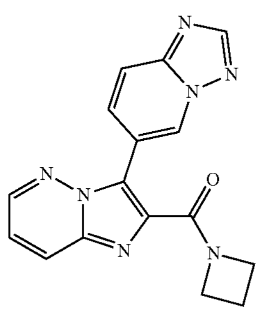 [SMILES: O=C(c1nc2cccnn2c1-c1ccc2ncnn2c1)N1CCC1] | 9.22 (br s, 1H), 8.40-8.44 (m, 2H), 7.98-8.07 (m, 2H), 7.86 (br d, J = 9 Hz, 1H), 7.21 (dd, J = 9.4, 4.3 Hz, 1H), 4.68-4.75 (m, 2H), 4.21-4.28 (m, 2H), 2.34-2.44 (m, 2H); 319.8 |
| 17 | Example 4[4]; C1 | 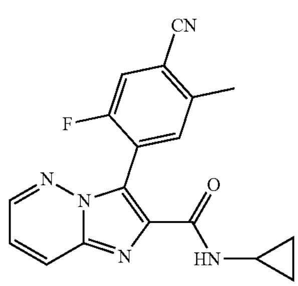 | 2.55 minutes[5]; 336.2 |
| 18 | Example 4[4]; C1 | 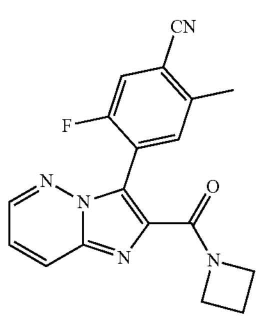 [SMILES: Cc1cc(-c2c(C(=O)N3CCC3)nc3cccnn23)c(F)cc1C#N] | 2.46 minutes[5]; 336.2 |

TABLE 1-continued

| Example Number | Method of Synthesis: Example Number; Source of Non-commercial Starting Materials | Structure | ¹H NMR (400 MHz, CDCl₃) δ (ppm); Mass spectrum, observed ion m/z [M + H]⁺ or HPLC retention time; Mass spectrum m/z [M + H]⁺ (unless otherwise indicated) |
|---|---|---|---|
| 19 | Example 2⁶; C1 | 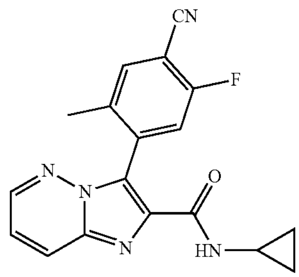 [SMILES: Cc1cc(C#N)c(F)cc1-c1c(C(=O)NC2CC2)nc2cccnn12] | 2.52 minutes⁵; 336.1 |
| 20 | Example 8⁷; C13 | 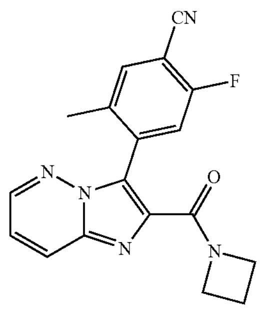 [SMILES: Cc1cc(C#N)c(F)cc1-c1c(C(=O)N2CCC2)nc2cccnn12] | ¹H NMR (400 MHz, CD₃OD) δ 8.48 (dd, J = 4.3, 1.4 Hz, 1H), 8.14 (dd, J = 9.3, 1.4 Hz, 1H), 7.74 (d, J = 6.5 Hz, 1H), 7.39 (d, J = 9.7 Hz, 1H), 7.35 (dd, J = 9.3, 4.5 Hz, 1H), 4.73-4.80 (m, 2H), 4.12-4.20 (m, 2H), 2.36-2.45 (m, 2H), 2.08 (s, 3H); 335.9 |
| 21 | Example 7; C11 | 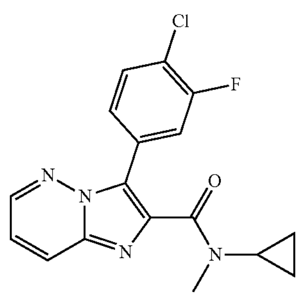 [SMILES: CN(C(=O)c1nc2cccnn2c1-c1ccc(Cl)c(F)c1)C1CC1] | ¹H NMR (400 MHz, DMSO-d₆), characteristic peaks: δ 8.68 (br d, J = 4.4 Hz, 1H), 8.27 (br d, J = 9 Hz, 1H), 7.87 (br d, J = 11 Hz, 1H), 7.76 (dd, J = 8.3, 8.2 Hz, 1H), 7.57 (br d, J = 9 Hz, 1H), 7.42 (dd, J = 9.3, 4.4 Hz, 1H), 2.99 and 2.80 (2 br s, total 3H), [0.31-0.42, 0.63-0.70 and 0.75-0.83 (3 m, total 4H)]⁸; 345.1 |
| 22 | Example 8; C9, C12 | 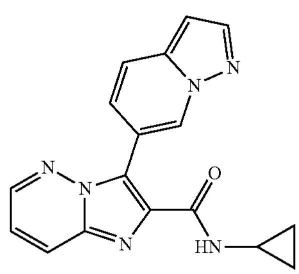 [SMILES: O=C(NC1CC1)c1nc2cccnn2c1-c1ccc2ccnn2c1] | ¹H NMR (400 MHz, CD₃OD) δ 9.01 (br s, 1H), 8.53 (dd, J = 4.2, 1.6 Hz, 1H), 8.12 (dd, J = 9.3, 1.6 Hz, 1H), 8.04 (d, J = 2.4 Hz, 1H), 7.74 (br d, J = 9.0 Hz, 1H), 7.54 (dd, J = 9.2, 1.4 Hz, 1H), 7.36 (dd, J = 9.2, 4.4 Hz, 1H), 6.67-6.70 (m, 1H), 2.81-2.88 (m, 1H), 0.79-0.86 (m, 2H), 0.65-0.71 (m, 2H); 341.0 [M + Na⁺] |
| 23 | Example 6¹; C13 | 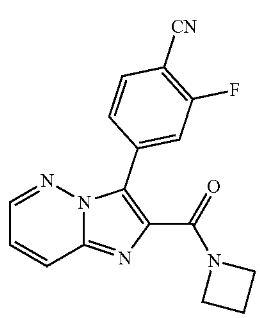 [SMILES: N#Cc1ccc(-c2c(C(=O)N3CCC3)nc3cccnn23)cc1F] | 8.42 (dd, J = 4.3, 1.6 Hz, 1H), 8.03 (dd, J = 9.3, 1.6 Hz, 1H), 7.78-7.84 (m, 2H), 7.72 (dd, J = 8.4, 6.3 Hz, 1H), 7.21 (dd, J = 9.2, 4.3 Hz, 1H), 4.60-4.66 (m, 2H), 4.21-4.27 (m, 2H), 2.33-2.42 (m, 2H); 322.2 |

TABLE 1-continued

| Example Number | Method of Synthesis: Example Number; Source of Non-commercial Starting Materials | Structure | $^1$H NMR (400 MHz, CDCl$_3$) δ (ppm); Mass spectrum, observed ion m/z [M + H]$^+$ or HPLC retention time; Mass spectrum m/z [M + H]$^+$ (unless otherwise indicated) |
|---|---|---|---|
| 24 | Example 5; C13 | 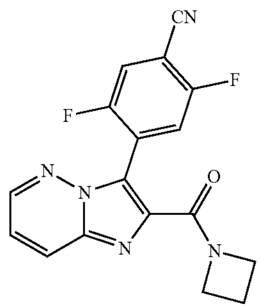 [SMILES: N#Cc1cc(F)c(-c2c(C(=O)N3CCC3)nc3cccnn23)cc1F] | 8.41 (dd, J = 4.3, 1.6 Hz, 1H), 8.04 (dd, J = 9.3, 1.6 Hz, 1H), 7.64 (dd, J = 8.8, 5.3 Hz, 1H), 7.45 (dd, J = 8.2, 5.0 Hz, 1H), 7.22 (dd, J = 9.3, 4.4 Hz, 1H), 4.73-4.80 (m, 2H), 4.20-4.26 (m, 2H), 2.36-2.45 (m, 2H); 339.9 |
| 25 | Example 5[9]; C8 | 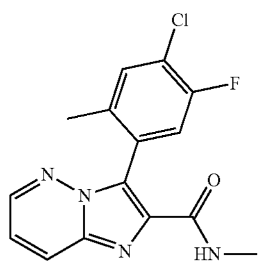 | 2.64 minutes[10]; 319 |

1. In this case, the catalyst used for the Suzuki reaction was dichlorobis(tricyclohexylphosphine)palladium(II).
2. The requisite ethyl 3-(5-chloropyridin-3-yl)imidazo[1,2-b]pyridazine-2-carboxylate was synthesized from C1 and 3-bromo-5-chloropyridine, using the method described for conversion of C1 to C5 in Example 3.
3. Compound C1 was converted to azetidin-1-yl(imidazo[1,2-b]pyridazin-2-yl)methanone using the method described for transformation of C8 to C13 in Example 8. Further elaboration to Example 16 was effected using the chemistry described for conversion of C1 to C5 in Example 3.
4. Reaction of C1 with 4-bromo-5-fluoro-2-methylbenzonitrile at elevated temperature, in the presence of allylpalladium chloride dimer and tetrabutylammonium acetate, afforded the requisite ethyl 3-(4-cyano-2-fluoro-5-methylphenyl)imidazo[1,2-b]pyridazine-2-carboxylate.
5. Conditions for analytical HPLC. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.
6. 3-(4-Cyano-5-fluoro-2-methylphenyl)imidazo[1,2-b]pyridazine-2-carboxylic acid was prepared from C1 and 4-bromo-2-fluoro-5-methylbenzonitrile using the chemistry described in footnote 4, followed by ester hydrolysis with lithium hydroxide.
7. The requisite aryl boronate derivative was prepared from the corresponding aryl bromide via reaction with 4,4,4',4',5,5,5',5'-octamethyl-2,2'-bi-1,3,2-dioxaborolane in the presence of [1,1'-bis(diphenylphosphino)ferrocene]dichloropalladium(II) and potassium acetate.
8. A $^1$H NMR spectrum obtained at elevated temperature (80° C.) provided the following data: $^1$H NMR (400 MHz, DMSO-d$_6$), characteristic peaks: δ 8.66 (br d, J=4 Hz, 1H), 8.23 (br d, J=9 Hz, 1H), 7.85 (br d, J=11 Hz, 1H), 7.73 (dd, J=8, 8 Hz, 1H), 7.62 (br d, J=8 Hz, 1H), 7.40 (dd, J=9, 4 Hz, 1H), 2.88-3.02 (br s, 3H), 0.28-0.61 (br s, 4H).
9. In this case, the catalyst used for the Suzuki reaction was [1,1'-bis(di-tert-butylphosphino)ferrocene]dichloropalladium (II).
10. Conditions for analytical HPLC. Column: Waters XBridge C18, 2.1×50 mm, 5 μm; Mobile phase A: 0.0375% trifluoroacetic acid in water; Mobile phase B: 0.01875% trifluoroacetic acid in acetonitrile; Gradient: 1% to 5% B over 0.6 minutes; 5% to 100% B over 3.4 minutes; Flow rate: 0.8 mL/minute.

TABLE 2

Examples 26-104 were prepared using methods analogous to those employed for Examples 1-25, or via methodology known to those skilled in the art.
Structure and mass spectrometry data for Examples 26-104.

| Example Number | Structure | Mass spectrum, observed ion m/z [M + H]$^+$, unless otherwise indicated |
|---|---|---|
| 26 | 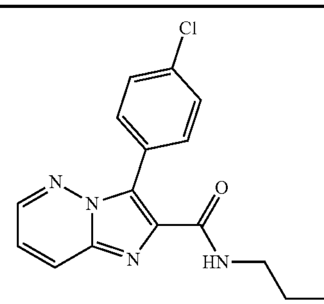 | 314.9 |

TABLE 2-continued
Examples 26-104 were prepared using methods analogous to those employed for Examples 1-25, or via methodology known to those skilled in the art.
Structure and mass spectrometry data for Examples 26-104.
| Example Number | Structure | Mass spectrum, observed ion m/z [M + H]+, unless otherwise indicated |
|---|---|---|
| 27 | 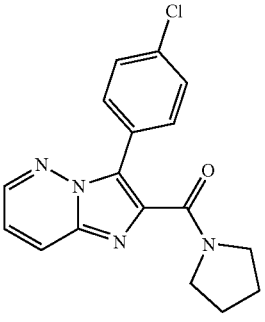 [SMILES: O=C(c1nc2cccnn2c1-c1ccc(Cl)cc1)N1CCCC1] | 326.9 |
| 28 | 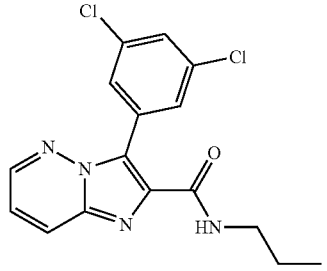 [SMILES: CCCNC(=O)c1nc2cccnn2c1-c1cc(Cl)cc(Cl)c1] | 348.8 |
| 29 | 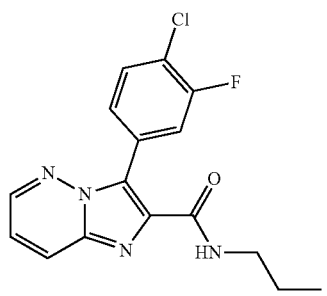 [SMILES: CCCNC(=O)c1nc2cccnn2c1-c1ccc(Cl)c(F)c1] | 354.9 [M + Na+] |
| 30 | 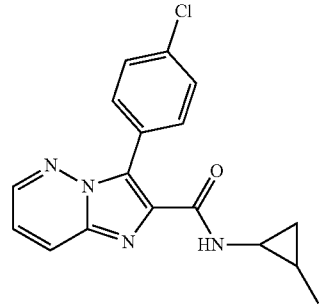 [SMILES: CC1CC1NC(=O)c1nc2cccnn2c1-c1ccc(Cl)cc1] | 326.9 |
| 31 | 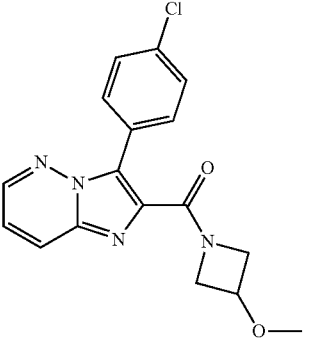 [SMILES: COC1CN(C(=O)c2nc3cccnn3c2-c2ccc(Cl)cc2)C1] | 343.1, 345.1 |
| 32 | 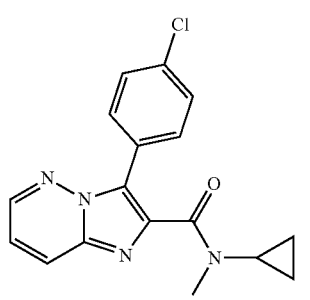 [SMILES: CN(C(=O)c1nc2cccnn2c1-c1ccc(Cl)cc1)C1CC1] | 326.9 |
| 33 | 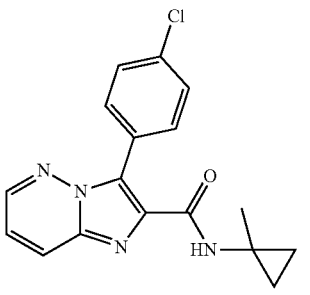 [SMILES: CC1(NC(=O)c2nc3cccnn3c2-c2ccc(Cl)cc2)CC1] | 327.0 |
| 34 | 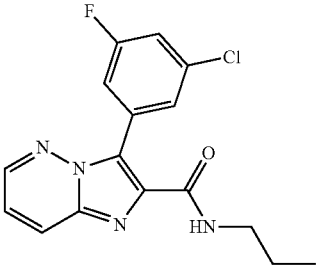 [SMILES: CCCNC(=O)c1nc2cccnn2c1-c1cc(F)cc(Cl)c1] | 333.0 |

TABLE 2-continued

Examples 26-104 were prepared using methods analogous to those employed for Examples 1-25, or via methodology known to those skilled in the art.
Structure and mass spectrometry data for Examples 26-104.

| Example Number | Structure | Mass spectrum, observed ion m/z [M + H]+, unless otherwise indicated |
|---|---|---|
| 35 | 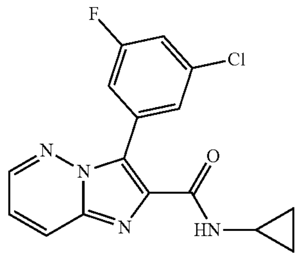 [SMILES: O=C(NC1CC1)c1nc2cccnn2c1-c1cc(F)cc(Cl)c1] | 330.9 |
| 36 | 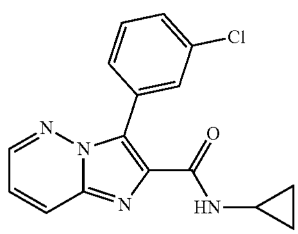 [SMILES: O=C(NC1CC1)c1nc2cccnn2c1-c1cccc(Cl)c1] | 312.9 |
| 37 | 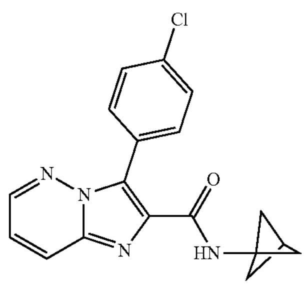 [SMILES: O=C(NC12CC(C1)C2)c1nc2cccnn2c1-c1ccc(Cl)cc1] | 339.1 |
| 38 | 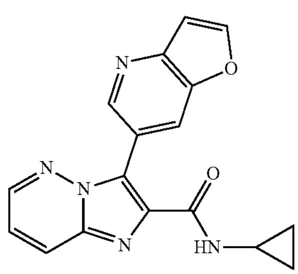 [SMILES: O=C(NC1CC1)c1nc2cccnn2c1-c1cnc2ccoc2c1] | 320.1 |
| 39 | 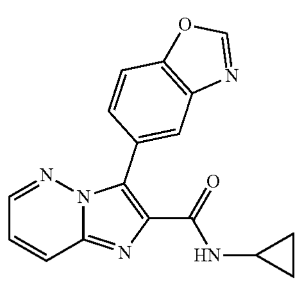 [SMILES: O=C(NC1CC1)c1nc2cccnn2c1-c1ccc2ocnc2c1] | 320.1 |
| 40 | 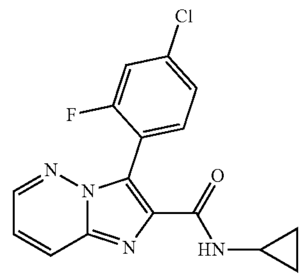 | 331.0, 333.1 |
| 41 | 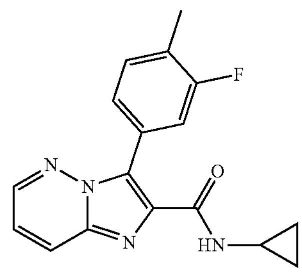 [SMILES: Cc1ccc(-c2c(C(=O)NC3CC3)nc3cccnn23)cc1F] | 311.1 |
| 42 | 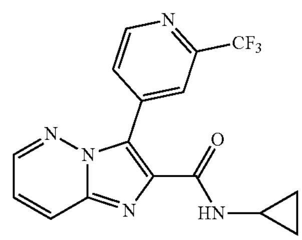 [SMILES: O=C(NC1CC1)c1nc2cccnn2c1-c1ccnc(C(F)(F)F)c1] | 347.9 |
| 43 | 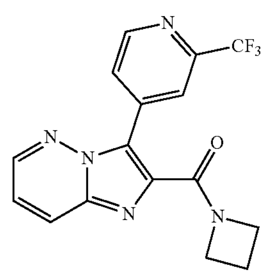 [SMILES: O=C(c1nc2cccnn2c1-c1ccnc(C(F)(F)F)c1)N1CCC1] | 347.9 |
| 44 | 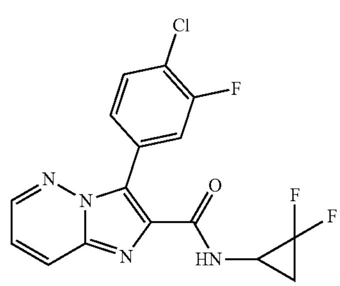 [SMILES: O=C(NC1CC1(F)F)c1nc2cccnn2c1-c1ccc(Cl)c(F)c1] | 367.0 |

TABLE 2-continued

Examples 26-104 were prepared using methods analogous to those employed for Examples 1-25, or via methodology known to those skilled in the art.
Structure and mass spectrometry data for Examples 26-104.

| Example Number | Structure | Mass spectrum, observed ion m/z [M + H]+, unless otherwise indicated |
|---|---|---|
| 45 | 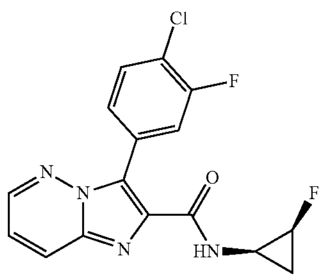 [SMILES: O=C(N[C@@H]1C[C@@H]1F)c1nc2cccnn2c1-c1ccc(Cl)c(F)c1] | 349.1 |
| 46 | 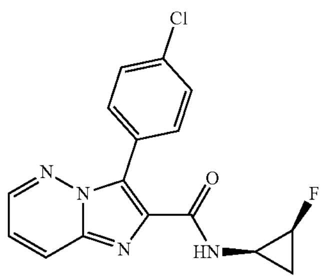 [SMILES: O=C(N[C@@H]1C[C@@H]1F)c1nc2cccnn2c1-c1ccc(Cl)cc1] | 353.0 [M + Na+] |
| 47 | 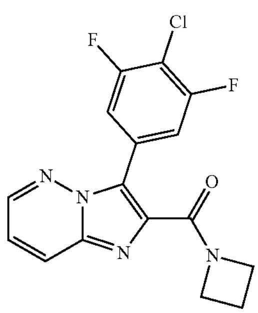 [SMILES: O=C(c1nc2cccnn2c1-c1cc(F)c(Cl)c(F)c1)N1CCC1] | 348.9 |
| 48 | 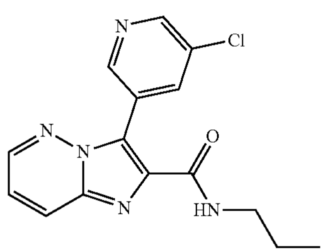 [SMILES: CCCNC(=O)c1nc2cccnn2c1-c1cncc(Cl)c1] | 315.9 |
| 49 | 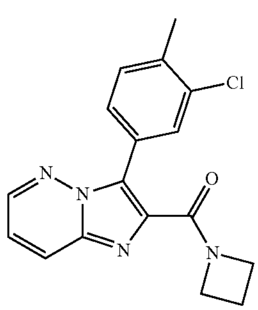 [SMILES: Cc1ccc(-c2c(C(=O)N3CCC3)nc3cccnn23)cc1Cl] | 327.1, 329.1 |
| 50 | 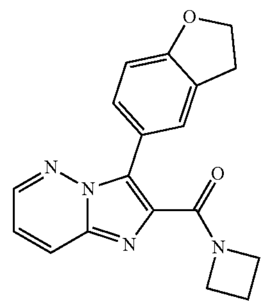 [SMILES: O=C(c1nc2cccnn2c1-c1ccc2c(c1)CCO2)N1CCC1] | 321.1 |
| 51 | 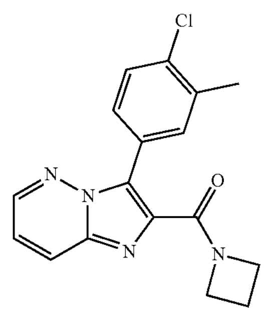 | 327.1, 329.0 |
| 52 | 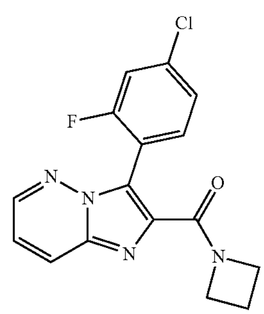 [SMILES: O=C(c1nc2cccnn2c1-c1ccc(Cl)cc1F)N1CCC1] | 330.9 |
| 53 | 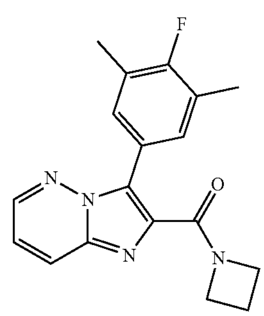 [SMILES: Cc1cc(-c2c(C(=O)N3CCC3)nc3cccnn23)cc(C)c1F] | 325.1 |

TABLE 2-continued

Examples 26-104 were prepared using methods analogous to those employed for Examples 1-25, or via methodology known to those skilled in the art.
Structure and mass spectrometry data for Examples 26-104.

| Example Number | Structure | Mass spectrum, observed ion m/z [M + H]+, unless otherwise indicated |
|---|---|---|
| 54 | 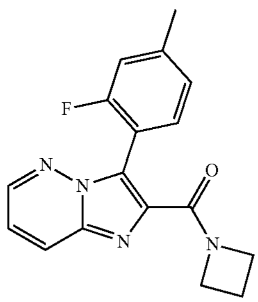 [SMILES: Cc1ccc(-c2c(C(=O)N3CCC3)nc3cccnn23)c(F)c1] | 310.9 |
| 55 | 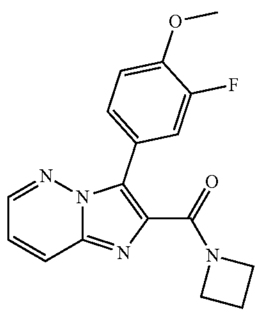 [SMILES: COc1ccc(-c2c(C(=O)N3CCC3)nc3cccnn23)cc1F] | 326.9 |
| 56 | 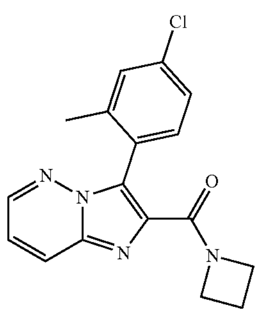 [SMILES: Cc1cc(Cl)ccc1-c1c(C(=O)N2CCC2)nc2cccnn12] | 327.2 |
| 57 | ·HCOOH | 393 |
| 58 | ·CF3COOH | 354 |
| 59 | ·CF3COOH | 354 |
| 60 | 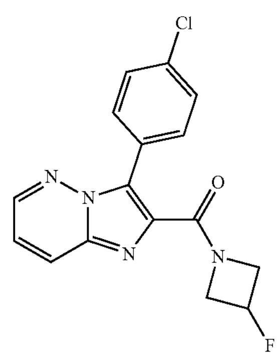 [SMILES: O=C(c1nc2cccnn2c1-c1ccc(Cl)cc1)N1CC(F)C1] | 331.1, 333.1 |
| 61 | 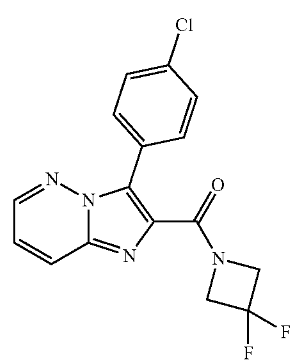 [SMILES: O=C(c1nc2cccnn2c1-c1ccc(Cl)cc1)N1CC(F)(F)C1] | 349.0, 351.0 |

TABLE 2-continued

Examples 26-104 were prepared using methods analogous to those employed for Examples 1-25, or via methodology known to those skilled in the art.
Structure and mass spectrometry data for Examples 26-104.

| Example Number | Structure | Mass spectrum, observed ion m/z [M + H]+, unless otherwise indicated |
|---|---|---|
| 62 | (quinoxalinyl-imidazo[1,2-b]pyridazine-azetidinyl ketone) ·HCOOH | 331 |
| 63 | (fluoro-acetylphenyl-imidazo[1,2-b]pyridazine-azetidinyl ketone) ·HCOOH | 339 |
| 64 | (methyl-chlorophenyl-imidazo[1,2-b]pyridazine-azetidinyl ketone) | 327 |
| 65 | (2,4-dichlorophenyl-imidazo[1,2-b]pyridazine-azetidinyl ketone) | 347 |
| 66 | (chloro-dimethylphenyl-imidazo[1,2-b]pyridazine-azetidinyl ketone) ·HCOOH | 341 |
| 67 | (2,3-dihydrobenzo[b][1,4]dioxinyl-imidazo[1,2-b]pyridazine-azetidinyl ketone) ·HCOOH | 337 |
| 68 | (4-chloro-2-fluorophenyl-imidazo[1,2-b]pyridazine-N-(2-fluorocyclopropyl)carboxamide) | 348.9 |
| 69 | (5-chloropyridin-3-yl-imidazo[1,2-b]pyridazine-N-(2-fluorocyclopropyl)carboxamide) | 331.9 |

TABLE 2-continued

Examples 26-104 were prepared using methods analogous to those employed for Examples 1-25, or via methodology known to those skilled in the art.
Structure and mass spectrometry data for Examples 26-104.

| Example Number | Structure | Mass spectrum, observed ion m/z [M + H]+, unless otherwise indicated |
|---|---|---|
| 70 | 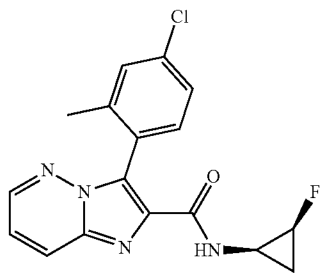 [SMILES: Cc1cc(Cl)ccc1-c1c(C(=O)N[C@@H]2C[C@@H]2F)nc2cccnn12] | 344.8 |
| 71 | 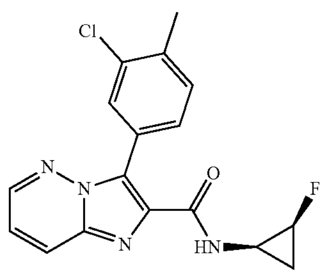 [SMILES: Cc1ccc(-c2c(C(=O)N[C@@H]3C[C@@H]3F)nc3cccnn23)cc1Cl] | 344.8 |
| 72 | 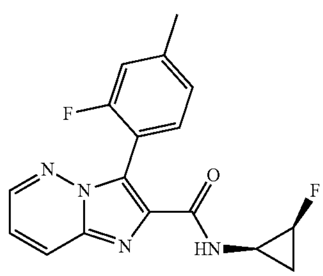 [SMILES: Cc1ccc(-c2c(C(=O)N[C@@H]3C[C@@H]3F)nc3cccnn23)c(F)c1] | 328.9 |
| 73 | 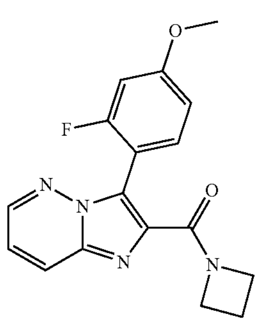 [SMILES: COc1ccc(-c2c(C(=O)N3CCC3)nc3cccnn23)c(F)c1] | 326.9 |
| 74 | | 319.8 |
| 75 | | 346.1 |
| 76 | | 346.0 |
| 77 | | 320.1 |

TABLE 2-continued

Examples 26-104 were prepared using methods analogous to those employed for Examples 1-25, or via methodology known to those skilled in the art.
Structure and mass spectrometry data for Examples 26-104.

| Example Number | Structure | Mass spectrum, observed ion m/z [M + H]+, unless otherwise indicated |
|---|---|---|
| 78 | (structure) | 320.1 |
| 79 | (structure) | 343.9 [M + Na+] |
| 80 | (structure) | 318.2 |
| 81 | (structure) | 319.0 |
| 82 | (structure) | 357.1 |
| 83 | (structure) | 346.9 |
| 84 | (structure) | 312.9 |
| 85 | (structure) | 300.8 |
| 86 | (structure) | 359.1 |

TABLE 2-continued

Examples 26-104 were prepared using methods analogous to those employed for Examples 1-25, or via methodology known to those skilled in the art.
Structure and mass spectrometry data for Examples 26-104.

| Example Number | Structure | Mass spectrum, observed ion m/z [M + H]+, unless otherwise indicated |
|---|---|---|
| 87 | 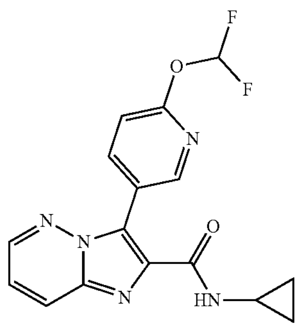 [SMILES: O=C(NC1CC1)c1nc2cccnn2c1-c1ccc(OC(F)F)nc1] | 346.1 |
| 88 | 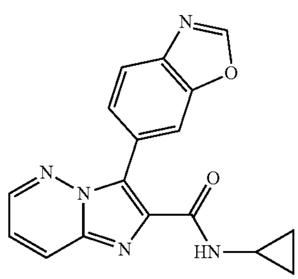 [SMILES: O=C(NC1CC1)c1nc2cccnn2c1-c1ccc2ncoc2c1] | 320.1 |
| 89 | 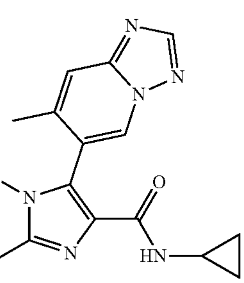 | 333.9 |
| 90 | 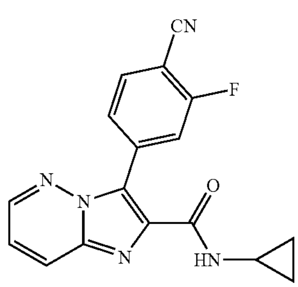 [SMILES: N#Cc1ccc(-c2c(C(=O)NC3CC3)nc3cccnn23)cc1F] | 322.2 |
| 91 | 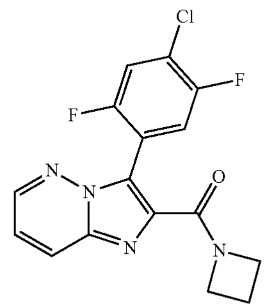 | 349.2 |
| 92 | 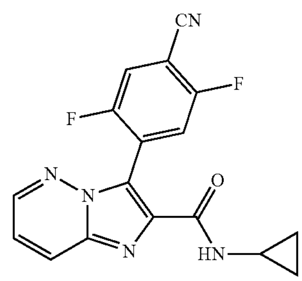 [SMILES: N#Cc1cc(F)c(-c2c(C(=O)NC3CC3)nc3cccnn23)cc1F] | 340.1 |
| 93 | 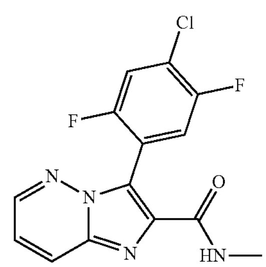 [SMILES: CNC(=O)c1nc2cccnn2c1-c1cc(F)c(Cl)cc1F] | 323 |
| 94 | 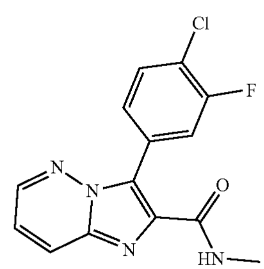 [SMILES: CNC(=O)c1nc2cccnn2c1-c1ccc(Cl)c(F)c1] | 305 |
| 95 | 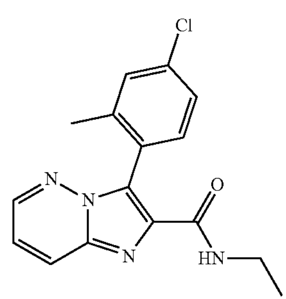 [SMILES: CCNC(=O)c1nc2cccnn2c1-c1ccc(Cl)cc1C] | 315 |

TABLE 2-continued
Examples 26-104 were prepared using methods analogous to those employed for Examples 1-25, or via methodology known to those skilled in the art.
Structure and mass spectrometry data for Examples 26-104.
| Example Number | Structure | Mass spectrum, observed ion m/z [M + H]+, unless otherwise indicated |
|---|---|---|
| 96 | 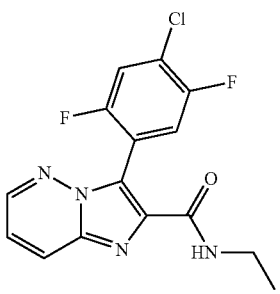 [SMILES: CCNC(=O)c1nc2cccnn2c1-c1cc(F)c(Cl)cc1F] | 337 |
| 97 | 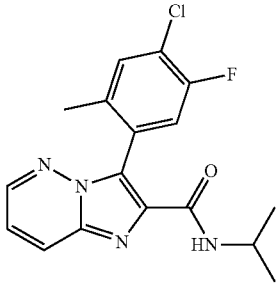 [SMILES: Cc1cc(Cl)c(F)cc1-c1c(C(=O)NC(C)C)nc2cccnn12] | 347 |
| 98 | 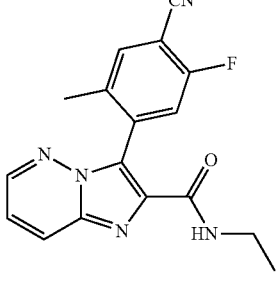 | 324 |
| 99 | 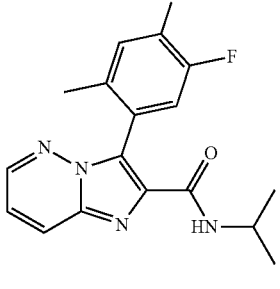 | 338.1 |
| 100 | 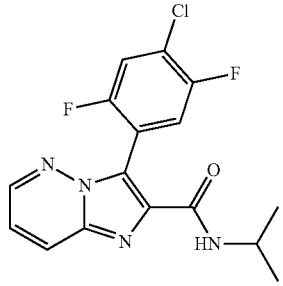 [SMILES: CC(C)NC(=O)c1nc2cccnn2c1-c1cc(F)c(Cl)cc1F] | 351 |
| 101 | 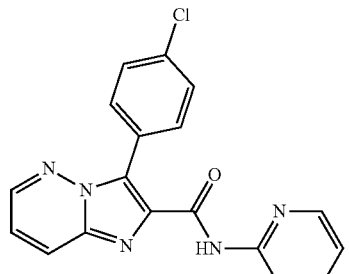 | 350.9 |
| 102 | 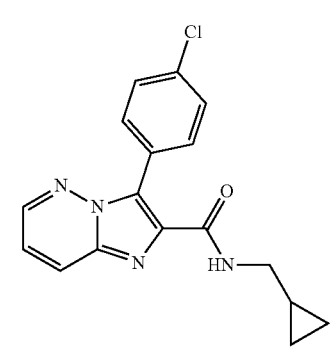 [SMILES: O=C(NCC1CC1)c1nc2cccnn2c1-c1ccc(Cl)cc1] | 348.9 [M + Na+] |
| 103 | 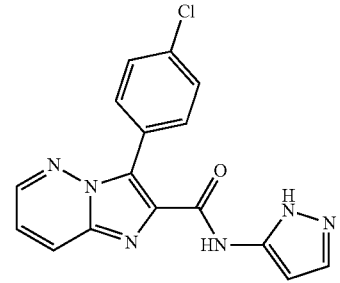 [SMILES: O=C(Nc1ccn[nH]1)c1nc2cccnn2c1-c1ccc(Cl)cc1] | 339.0 |

TABLE 2-continued

Examples 26-104 were prepared using methods analogous to those employed for Examples 1-25, or via methodology known to those skilled in the art.
Structure and mass spectrometry data for Examples 26-104.

| Example Number | Structure | Mass spectrum, observed ion m/z [M + H]+, unless otherwise indicated |
| --- | --- | --- |
| 104 | (structure) | 348.9 |

The PDE4A, PDE4B, PDE4C and PDE4D binding affinity for the compounds of the present invention was determined utilizing the following biological assay(s):

Biological Assays

Human PDE4A3 coding sequence (amino acids 2 to 825 from the sequence with accession number NP_001104779) was cloned into the baculovirus expression vector pFastBac (Invitrogen) engineered to include an N-terminal His6 affinity tag and a c-terminal FLAG affinity tag to aid in purification. The recombinant Bacmid was isolated and used to transfect insect cells to generate a viral stock. To generate cell paste for purification, insect cells were infected with the virus stock and cells were harvested 72 hours after infection. Insect cell paste was lysed and after centrifugation, the supernatant was batch bound to Ni-NTA agarose (GE Healthcare) and eluted with 250 mM imidazole. This eluate was diluted with FLAG buffer (50 mM Tris HCL pH 7.5, 100 mM NaCl, 5% Glycerol, 1 mM TCEP with protease inhibitors) and batch bound to ant-FLAG M2 agarose (Sigma) overnight at 4° C. The agarose was packed into a column, washed with buffer and eluted with buffer containing elute using 250 ug/ml Flag-peptide. Fractions were analyzed using SDS-PAGE Coomassie blue staining and pooled based on purity. Pooled fractions were chromatographed on a S200 120 ml column (GE Healthcare) in 50 mM Tris HCL pH 7.5, 150 mM NaCl, 10% Glycerol, 2 mM TCEP with protease inhibitors. PDE4A3 fractions were analyzed by SDS-PAGE Coomassie blue staining, pooled based on purity, dialyzed against 50 mM Tris HCL pH 7.5, 100 mM NaCl, 20% Glycerol, 2 mM TCEP, frozen and stored at −80° C.

Human PDE4B1 coding sequence (amino acids 122 to 736 from the sequence with accession number Q07343) with the mutations resulting in the amino acid substitutions S134E, S654A, S659A, and S661A was cloned into the baculovirus expression vector pFastBac (Invitrogen) engineered to include a N-terminal His6 affinity tag to aid in purification followed by a thrombin cleavage site. The recombinant Bacmid was isolated and used to transfect insect cells to generate a viral stock. To generate cell paste for purification, insect cells were infected with the virus stock and cells were harvested 72 hours after infection as described in Seeger, T. F. et al., Brain Research 985 (2003) 113-126. Insect cell paste was lysed and after centrifugation, the supernatant was chromatographed on Ni-NTA agarose (Qiagen) as described in Seeger, T. F. et al., Brain Research 985 (2003) 113-126. Ni-NTA agarose eluting fractions containing PDE4 were pooled, diluted with Q buffer A (20 mM Tris HCl pH 8, 5% glycerol, 1 mM TCEP) to reduce NaCl to ∼100 mM and loaded on a Source 15Q (GE Healthcare) column. After washing with Q buffer A/10% buffer B to baseline, PDE4D was eluted with a gradient from 10% to 60% of Buffer B (20 mM Tris HCl pH 8, 1 M NaCl, 5% glycerol, 1 mM TCEP). PDE4D fractions were analyzed by SDS-PAGE Coomassie blue staining, pooled based on purity, frozen and stored at −80° C.

Human PDE4C1 coding sequence (amino acids 2 to 712 from the sequence with accession number NP_000914.2) was cloned into the baculovirus expression vector pFastBac (Invitrogen) engineered to include an N-terminal His6 affinity tag and a c-terminal FLAG affinity tag to aid in purification. The recombinant Bacmid was isolated and used to transfect insect cells to generate a viral stock. To generate cell paste for purification, insect cells were infected with the virus stock and cells were harvested 72 hours after infection. Insect cell paste was lysed and after centrifugation, the supernatant was batch bound to Ni-NTA agarose (GE Healthcare) and eluted with 250 mM imidazole. This eluate was diluted with FLAG buffer (50 mM Tris HCL pH 7.5, 100 mM NaCl, 5% Glycerol, 1 mM TCEP with protease inhibitors) and batch bound to ant-FLAG M2 agarose (Sigma) overnight at 4° C. The agarose was packed into a column, washed with buffer and eluted with buffer containing elute using 250 ug/ml Flag-peptide. Fractions were analyzed using SDS-PAGE Coomassie blue staining and pooled based on purity. Pooled fractions were chromatographed on a S200 120 ml column (GE Healthcare) in 50 mM Tris HCL pH 7.5, 150 mM NaCl, 10% Glycerol, 2 mM TCEP with protease inhibitors. PDE4C1 fractions were analyzed by SDS-PAGE Coomassie blue staining, pooled based on purity, dialyzed against 50 mM Tris HCL pH 7.5, 100 mM NaCl, 20% Glycerol, 2 mM TCEP, frozen and stored at −80° C.

A portion of the human PDE4D3 coding sequence (amino acids 50 to 672 from the sequence with accession number Q08499-2) was cloned into the baculovirus expression vector pFastBac (Invitrogen) engineered to include a C-terminal His6 affinity tag to aid in purification as described in Seeger, T. F. et al., Brain Research 985 (2003) 113-126. The recombinant Bacmid was isolated and used to transfect insect cells to generate a viral stock. To generate cell paste for purification, insect cells were infected and cells were harvested 72 hours after infection. Insect cell paste was lysed and after centrifugation, the supernatant was chromatographed on Ni-NTA agarose (Qiagen) as described in Seeger, T. F. et al., Brain Research 985 (2003) 113-126. Ni-NTA agarose eluting fractions containing PDE4 were pooled, diluted with Q Buffer A (50 mM Tris HCl pH 8, 4% glycerol, 100 mM NaCl, 1 mM TCEP, Protease inhibitors EDTA-free (Roche)) to reduce NaCl to ∼200 mM, and loaded on a Q Sepharose (GE Healthcare) column. After washing with Q buffer A to baseline, PDE4D was eluted with a gradient from 10% to 60% of Buffer B (50 mM Tris HCl pH 8, 1 M NaCl, 4% glycerol, 1 mM TCEP). PDE4D fractions were analyzed by SDS-PAGE Coomassie blue staining, pooled based on purity, frozen and stored at −80° C.

The PDE4A3, PDE4B1, PDE4C1 and PDE4D3 assays use the Scintillation Proximity Assay (SPA) technology to measure the inhibition of human recombinant PDE4A1, PDE4B3, PDE4C1, and PDE4D3 enzyme activity by compounds in vitro. The PDE4A1, PDE4B3, PDE4C1, and PDE4D3 assays are run in parallel using identical parameters, except for the concentration of enzyme (80 pM PDE4A3, 40 pM PDE4B3, 40 pM PDE4C1 and 10 pM PDE4D). The assays are performed in a 384-well format with 50 uL assay buffer (50 mM TRIS pH7.5; 1.3 mM MgCl2; 0.01% Brij) containing enough PDE4A3, PDE4B1, PDE4C1, and PDE4D to convert ~20% of substrate (1 pM cAMP consisting of 20 nM 3H-cAMP+980 uM cold cAMP) and a range of inhibitors. Reactions are incubated for 30 min at 25° C. The addition of 20 uL of 8 mg/ml yttrium silicate SPA beads (Perkin Elmer) stops the reaction. The plates are sealed (TopSeal, Perkin Elmer) and the beads are allowed to settle for 8 hrs, after which they are read on the Trilux Microbeta overnight.

TABLE 3

Biological data for Examples 1-104.

| Example Number | Human PDE4A FL; $IC_{50}$ (nM)[b] | Human PDE4B FL; $IC_{50}$ (nM)[b] | Human PDE4C FL; $IC_{50}$ (nM)[b] | Human PDE4D FL; $IC_{50}$ (nM)[b] | IUPAC Name |
|---|---|---|---|---|---|
| 1 | 38.6 | 35.5[c] | 130 | 10300[c] | azetidin-1-yl[3-(4-chlorophenyl)imidazo[1,2-b]pyridazin-2-yl]methanone |
| 2 | 10.7 | 17.7 | 27.9 | 4340[c] | 3-(4-chlorophenyl)-N-cyclopropylimidazo[1,2-b]pyridazine-2-carboxamide |
| 3 | 12.7 | 29.1 | 51.9 | 2410 | azetidin-1-yl[3-(3,5-difluoro-4-methoxyphenyl)imidazo[1,2-b]pyridazin-2-yl]methanone |
| 4 | 187 | 380[c] | 561 | >27100[c] | N-cyclopropyl-3-(2-methoxypyrimidin-5-yl)imidazo[1,2-b]pyridazine-2-carboxamide |
| 5 | 40.2 | 89.5 | 208 | >26600 | 3-(6-cyanopyridin-3-yl)-N-cyclopropylimidazo[1,2-b]pyridazine-2-carboxamide |
| 6 | 64.4 | 49.3 | 326 | 4890[c] | N-cyclopropyl-3-([1,2,4]triazolo[1,5-a]pyridin-6-yl)imidazo[1,2-b]pyridazine-2-carboxamide |
| 7 | 2.77 | <1.89 | 2.35 | 34.5 | 3-(4-chloro-3-fluorophenyl)-N-(1-methyl-1H-pyrazol-4-yl)imidazo[1,2-b]pyridazine-2-carboxamide |
| 8 | 20.0 | 41.3[c] | 64.9 | 5440[c] | azetidin-1-yl[3-(pyrazolo[1,5-a]pyridin-6-yl)imidazo[1,2-b]pyridazin-2-yl]methanone |
| 9 | 3.83 | 10.5 | 40.9 | 1490 | 3-(4-chloro-2,5-difluorophenyl)-N-cyclopropylimidazo[1,2-b]pyridazine-2-carboxamide |
| 10 | 1.51 | 3.80[c] | 6.84 | 590[c] | 3-(4-chloro-3-fluorophenyl)-N-cyclopropylimidazo[1,2-b]pyridazine-2-carboxamide |
| 11 | ND | 1.60 | ND | 334[c] | N-cyclopropyl-3-(3,4-dichlorophenyl)imidazo[1,2-b]pyridazine-2-carboxamide |
| 12 | 14.4 | 35.8[c] | 89.6 | 5220[c] | 3-(4-chloro-2-methylphenyl)-N-cyclopropylimidazo[1,2-b]pyridazine-2-carboxamide |
| 13 | 5.13 | 4.63[c] | 17.3 | 669[c] | azetidin-1-yl[3-(4-chloro-3-fluorophenyl)imidazo[1,2- |

TABLE 3-continued

Biological data for Examples 1-104.

| Example Number | Human PDE4A FL; IC$_{50}$ (nM)[b] | Human PDE4B FL; IC$_{50}$ (nM)[b] | Human PDE4C FL; IC$_{50}$ (nM)[b] | Human PDE4D FL; IC$_{50}$ (nM)[b] | IUPAC Name |
|---|---|---|---|---|---|
| 14 | 73.7 | 79.1[c] | 108 | >8010[c] | b]pyridazin-2-yl]methanone 3-(5-chloropyridin-3-yl)-N-cyclopropylimidazo[1,2-b]pyridazine-2-carboxamide |
| 15 | 264 | 252[c] | 421 | >23700[c] | azetidin-1-yl[3-(5-chloropyridin-3-yl)imidazo[1,2-b]pyridazin-2-yl]methanone |
| 16 | ND | 552 | ND | >27500 | azetidin-1-yl[3-([1,2,4]triazolo[1,5-a]pyridin-6-yl)imidazo[1,2-b]pyridazin-2-yl]methanone |
| 17 | 89.9 | 175[c] | 216 | >18200[c] | 3-(4-cyano-2-fluoro-5-methylphenyl)-N-cyclopropylimidazo[1,2-b]pyridazine-2-carboxamide |
| 18 | 55.0 | 150 | 147 | 8200 | 4-[2-(azetidin-1-ylcarbonyl)imidazo[1,2-b]pyridazin-3-yl]-5-fluoro-2-methylbenzonitrile |
| 19 | 16.9 | 13.6 | 98.4 | 645 | 3-(4-cyano-5-fluoro-2-methylphenyl)-N-cyclopropylimidazo[1,2-b]pyridazine-2-carboxamide |
| 20 | 6.70 | 5.74[c] | 74.8 | 490[c] | 4-[2-(azetidin-1-ylcarbonyl)imidazo[1,2-b]pyridazin-3-yl]-2-fluoro-5-methylbenzonitrile |
| 21 | 53.7 | 91.3[c] | 170 | >12300[c] | 3-(4-chloro-3-fluorophenyl)-N-cyclopropyl-N-methylimidazo[1,2-b]pyridazine-2-carboxamide |
| 22 | 27.6 | 58.9 | 71.2 | 1890 | N-cyclopropyl-3-(pyrazolo[1,5-a]pyridin-6-yl)imidazo[1,2-b]pyridazine-2-carboxamide |
| 23 | 15.1 | 30.5 | 45.8 | 4130 | 4-[2-(azetidin-1-ylcarbonyl)imidazo[1,2-b]pyridazin-3-yl]-2-fluorobenzonitrile |
| 24 | 5.04 | 19.1 | 59.7 | >2150 | 4-[2-(azetidin-1-ylcarbonyl)imidazo[1,2-b]pyridazin-3-yl]-2,5-difluorobenzonitrile |
| 25 | 38.6 | 140 | 150 | 4970 | 3-(4-chloro-5-fluoro-2-methylphenyl)-N-methylimidazo[1,2-b]pyridazine-2-carboxamide |
| 26 | 85.5 | 114 | 111 | 3800[c] | 3-(4-chlorophenyl)-N-propylimidazo[1,2-b]pyridazine-2-carboxamide |
| 27 | 742 | 609 | 768 | 5620[c] | [3-(4-chlorophenyl)imidazo[1,2-b]pyridazin-2-yl](pyrrolidin-1-yl)methanone |
| 28 | 15.6 | 31.7 | 49.0 | 393[c] | 3-(3,5-dichlorophenyl)-N-propylimidazo[1,2- |

TABLE 3-continued

Biological data for Examples 1-104.

| Example Number | Human PDE4A FL; IC$_{50}$ (nM)[b] | Human PDE4B FL; IC$_{50}$ (nM)[b] | Human PDE4C FL; IC$_{50}$ (nM)[b] | Human PDE4D FL; IC$_{50}$ (nM)[b] | IUPAC Name |
|---|---|---|---|---|---|
| 29 | 3.48 | 5.05 | 13.8 | 409[c] | b]pyridazine-2-carboxamide 3-(4-chloro-3-fluorophenyl)-N-propylimidazo[1,2-b]pyridazine-2-carboxamide |
| 30 | 11.6 | 55.0 | 24.5 | 4000[c] | 3-(4-chlorophenyl)-N-(2-methylcyclopropyl)imidazo[1,2-b]pyridazine-2-carboxamide |
| 31 | 2820 | 2670 | 5810 | >26200 | [3-(4-chlorophenyl)imidazo[1,2-b]pyridazin-2-yl](3-methoxyazetidin-1-yl)methanone |
| 32 | 1030 | 419[c] | 469 | >30000[c] | 3-(4-chlorophenyl)-N-cyclopropyl-N-methylimidazo[1,2-b]pyridazine-2-carboxamide |
| 33 | 58.6 | 53.6 | 127 | 2330 | 3-(4-chlorophenyl)-N-(1-methylcyclopropyl)imidazo[1,2-b]pyridazine-2-carboxamide |
| 34 | 29.5 | 83.2[c] | 47.0 | 2110[c] | 3-(3-chloro-5-fluorophenyl)-N-propylimidazo[1,2-b]pyridazine-2-carboxamide |
| 35 | 35.7 | 48.0 | 37.0 | 1220 | 3-(3-chloro-5-fluorophenyl)-N-cyclopropylimidazo[1,2-b]pyridazine-2-carboxamide |
| 36 | 23.7 | 6.99 | 21.0 | 254 | 3-(3-chlorophenyl)-N-cyclopropylimidazo[1,2-b]pyridazine-2-carboxamide |
| 37 | 127 | 75.3 | 161 | 2570 | N-(bicyclo[1.1.1]pent-1-yl)-3-(4-chlorophenyl)imidazo[1,2-b]pyridazine-2-carboxamide |
| 38 | ND | 268 | ND | 11200 | N-cyclopropyl-3-(furo[3,2-b]pyridin-6-yl)imidazo[1,2-b]pyridazine-2-carboxamide |
| 39 | 14.8 | 26.5 | 67.8 | 3820[b] | 3-(1,3-benzoxazol-5-yl)-N-cyclopropylimidazo[1,2-b]pyridazine-2-carboxamide |
| 40 | 19.6 | 65.3 | 58.1 | 9020 | 3-(4-chloro-2-fluorophenyl)-N-cyclopropylimidazo[1,2-b]pyridazine-2-carboxamide |
| 41 | 3.13 | 8.05 | 16.8 | 467 | N-cyclopropyl-3-(3-fluoro-4-methylphenyl)imidazo[1,2-b]pyridazine-2-carboxamide |
| 42 | 415 | 393[c] | 357 | >12200[c] | N-cyclopropyl-3-[2-(trifluoromethyl)pyridin-4-yl]imidazo[1,2-b]pyridazine-2-carboxamide |
| 43 | ND | 270 | ND | >16900 | azetidin-1-yl{3-[2-(trifluoromethyl)pyridin- |

TABLE 3-continued

Biological data for Examples 1-104.

| Example Number | Human PDE4A FL; IC$_{50}$ (nM)[b] | Human PDE4B FL; IC$_{50}$ (nM)[b] | Human PDE4C FL; IC$_{50}$ (nM)[b] | Human PDE4D FL; IC$_{50}$ (nM)[b] | IUPAC Name |
|---|---|---|---|---|---|
| | | | | | 4-yl]imidazo[1,2-b]pyridazin-2-yl}methanone |
| 44 | ND | 3.92 | ND | 320 | 3-(4-chloro-3-fluorophenyl)-N-(2,2-difluorocyclopropyl)imidazo[1,2-b]pyridazine-2-carboxamide |
| 45 | 2.91 | 1.97 | 11.7 | 159 | 3-(4-chloro-3-fluorophenyl)-N-[(1R,2S)-2-fluorocyclopropyl]imidazo[1,2-b]pyridazine-2-carboxamide |
| 46 | 15.2 | 12.3 | 39.3 | 971 | 3-(4-chlorophenyl)-N-[(1R,2S)-2-fluorocyclopropyl]imidazo[1,2-b]pyridazine-2-carboxamide |
| 47 | 7.37 | 3.90[c] | 23.9 | 334[c] | azetidin-1-yl[3-(4-chloro-3,5-difluorophenyl)imidazo[1,2-b]pyridazin-2-yl]methanone |
| 48 | 768 | 322 | 212 | >7670 | 3-(5-chloropyridin-3-yl)-N-propylimidazo[1,2-b]pyridazine-2-carboxamide |
| 49 | 4.16 | 13.3 | 19.0 | 535[b] | azetidin-1-yl[3-(3-chloro-4-methylphenyl)imidazo[1,2-b]pyridazin-2-yl]methanone |
| 50 | 28.1 | 116 | 235 | 3140 | azetidin-1-yl[3-(2,3-dihydro-1-benzofuran-5-yl)imidazo[1,2-b]pyridazin-2-yl]methanone |
| 51 | ND | 42.9 | ND | 2810 | azetidin-1-yl[3-(4-chloro-3-methylphenyl)imidazo[1,2-b]pyridazin-2-yl]methanone |
| 52 | 24.3 | 37.3 | 113 | 5510 | azetidin-1-yl[3-(4-chloro-2-fluorophenyl)imidazo[1,2-b]pyridazin-2-yl]methanone |
| 53 | 17.8 | 63.3 | 153 | 3110 | azetidin-1-yl[3-(4-fluoro-3,5-dimethylphenyl)imidazo[1,2-b]pyridazin-2-yl]methanone |
| 54 | 103 | 107[c] | 136 | >20000[c] | azetidin-1-yl[3-(2-fluoro-4-methylphenyl)imidazo[1,2-b]pyridazin-2-yl]methanone |
| 55 | 176 | 200 | >1550 | >20900[c] | azetidin-1-yl[3-(3-fluoro-4-methoxyphenyl)imidazo[1,2-b]pyridazin-2-yl]methanone |
| 56 | 22.7 | 43.1[c] | 84.5 | 3930[c] | azetidin-1-yl[3-(4-chloro-2-methylphenyl)imidazo[1,2-b]pyridazin-2-yl]methanone |
| 57 | ND | 236 | ND | >21800 | 3-(4-chlorophenyl)-N-[2-(2-hydroxyphenyl)ethyl]imidazo[1,2-b]pyridazine-2- |

TABLE 3-continued

Biological data for Examples 1-104.

| Example Number | Human PDE4A FL; IC$_{50}$ (nM)[b] | Human PDE4B FL; IC$_{50}$ (nM)[b] | Human PDE4C FL; IC$_{50}$ (nM)[b] | Human PDE4D FL; IC$_{50}$ (nM)[b] | IUPAC Name |
|---|---|---|---|---|---|
| 58 | ND | 43.3 | ND | 831 | carboxamide, formate salt<br>3-(4-chlorophenyl)-N-(5-methyl-1,2-oxazol-3-yl)imidazo[1,2-b]pyridazine-2-carboxamide, trifluoroacetate salt |
| 59 | ND | 58.5 | ND | 749 | 3-(4-chlorophenyl)-N-(2-methyl-2H-1,2,3-triazol-4-yl)imidazo[1,2-b]pyridazine-2-carboxamide, trifluoroacetate salt |
| 60 | 269 | 196 | 287 | >4930 | [3-(4-chlorophenyl)imidazo[1,2-b]pyridazin-2-yl](3-fluoroazetidin-1-yl)methanone |
| 61 | 144 | 184 | 126 | 1930 | [3-(4-chlorophenyl)imidazo[1,2-b]pyridazin-2-yl](3,3-difluoroazetidin-1-yl)methanone |
| 62 | ND | 275 | ND | 11000 | azetidin-1-yl[3-(quinoxalin-6-yl)imidazo[1,2-b]pyridazin-2-yl]methanone, formate salt |
| 63 | ND | 17.7 | ND | 394 | 1-{3-[2-(azetidin-1-ylcarbonyl)imidazo[1,2-b]pyridazin-3-yl]-4-fluorophenyl}ethanone, formate salt |
| 64 | ND | 24.2 | ND | 844 | azetidin-1-yl[3-(5-chloro-2-methylphenyl)imidazo[1,2-b]pyridazin-2-yl]methanone |
| 65 | ND | 71.9 | ND | 3720 | azetidin-1-yl[3-(2,4-dichlorophenyl)imidazo[1,2-b]pyridazin-2-yl]methanone |
| 66 | ND | 41.0 | ND | 3390 | azetidin-1-yl[3-(3-chloro-2,4-dimethylphenyl)imidazo[1,2-b]pyridazin-2-yl]methanone, formate salt |
| 67 | ND | 59.8 | ND | 2260 | azetidin-1-yl[3-(2,3-dihydro-1,4-benzodioxin-6-yl)imidazo[1,2-b]pyridazin-2-yl]methanone, formate salt |
| 68 | 10.6 | 35.4 | 25.1 | 2620 | 3-(4-chloro-2-fluorophenyl)-N-[(1R,2S)-2-fluorocyclopropyl]imidazo[1,2-b]pyridazine-2-carboxamide |
| 69 | ND | 116 | ND | 3330 | 3-(5-chloropyridin-3-yl)-N-[(1R,2S)-2-fluorocyclopropyl]imidazo[1,2-b]pyridazine-2-carboxamide |
| 70 | 36.4 | 31.0[c] | 90.0 | 5760[c] | 3-(4-chloro-2-methylphenyl)-N-[(1R,2S)-2-fluorocyclopropyl]imidazo[1,2-b]pyridazine-2-carboxamide |

TABLE 3-continued

Biological data for Examples 1-104.

| Example Number | Human PDE4A FL; IC$_{50}$ (nM)[b] | Human PDE4B FL; IC$_{50}$ (nM)[b] | Human PDE4C FL; IC$_{50}$ (nM)[b] | Human PDE4D FL; IC$_{50}$ (nM)[b] | IUPAC Name |
|---|---|---|---|---|---|
| 71 | <0.669 | 2.82 | 2.00 | 113 | 3-(3-chloro-4-methylphenyl)-N-[(1R,2S)-2-fluorocyclopropyl]imidazo[1,2-b]pyridazine-2-carboxamide |
| 72 | ND | 192 | ND | 6590 | N-[(1R,2S)-2-fluorocyclopropyl]-3-(2-fluoro-4-methylphenyl)imidazo[1,2-b]pyridazine-2-carboxamide |
| 73 | 165 | 495 | 1440 | >24700 | azetidin-1-yl[3-(2-fluoro-4-methoxyphenyl)imidazo[1,2-b]pyridazin-2-yl]methanone |
| 74 | ND | 225 | ND | 10500 | azetidin-1-yl[3-(pyrazolo[1,5-a]pyrimidin-6-yl)imidazo[1,2-b]pyridazin-2-yl]methanone |
| 75 | 10.5 | 5.99[c] | 24.9 | 104[c] | N-cyclopropyl-3-[2-(difluoromethoxy)pyridin-4-yl]imidazo[1,2-b]pyridazine-2-carboxamide |
| 76 | 7.09 | 5.43[c] | 22.2 | 94.5[c] | azetidin-1-yl{3-[2-(difluoromethoxy)pyridin-4-yl]imidazo[1,2-b]pyridazin-2-yl}methanone |
| 77 | 46.1 | 80.4[c] | 186 | >16600[c] | azetidin-1-yl[3-(1,3-benzoxazol-6-yl)imidazo[1,2-b]pyridazin-2-yl]methanone |
| 78 | ND | 364 | ND | 6490 | N-cyclopropyl-3-(pyrazolo[1,5-a]pyrimidin-6-yl)imidazo[1,2-b]pyridazine-2-carboxamide |
| 79 | 48.8 | 190[c] | 297 | >25400[c] | 3-(4-cyano-2-fluorophenyl)-N-cyclopropylimidazo[1,2-b]pyridazine-2-carboxamide |
| 80 | ND | 344 | ND | >25400 | 3-(5-cyano-2-methylphenyl)-N-cyclopropylimidazo[1,2-b]pyridazine-2-carboxamide |
| 81 | 7.86 | 9.34[c] | 25.8 | 853[c] | 3-(4-chloro-3-fluorophenyl)-N-ethylimidazo[1,2-b]pyridazine-2-carboxamide |
| 82 | 12.0 | 5.14 | 43.4 | 56.5 | 3-(4-chloro-3-fluorophenyl)-N-(1H-pyrazol-4-yl)imidazo[1,2-b]pyridazine-2-carboxamide |
| 83 | 6.21 | 5.39 | 40.0 | 495 | azetidin-1-yl[3-(3,4-dichlorophenyl)imidazo[1,2-b]pyridazin-2-yl]methanone |
| 84 | 16.7 | 7.84[c] | 44.4 | 977[c] | azetidin-1-yl[3-(3-chlorophenyl)imidazo[1,2-b]pyridazin-2-yl]methanone |

TABLE 3-continued

Biological data for Examples 1-104.

| Example Number | Human PDE4A FL; IC$_{50}$ (nM)[b] | Human PDE4B FL; IC$_{50}$ (nM)[b] | Human PDE4C FL; IC$_{50}$ (nM)[b] | Human PDE4D FL; IC$_{50}$ (nM)[b] | IUPAC Name |
|---|---|---|---|---|---|
| 85 | 25.6 | 87.3[c] | 47.2 | 6700[c] | 3-(4-chlorophenyl)-N-ethylimidazo[1,2-b]pyridazine-2-carboxamide |
| 86 | 5.83 | 7.72 | 25.0 | 179 | azetidin-1-yl[3-(2,2-difluoro-1,3-benzodioxol-5-yl)imidazo[1,2-b]pyridazin-2-yl]methanone |
| 87 | 240 | 173 | 397 | 6790 | N-cyclopropyl-3-[6-(difluoromethoxy)pyridin-3-yl]imidazo[1,2-b]pyridazine-2-carboxamide |
| 88 | 45.0 | 39.2[c] | 136 | 10400[c] | 3-(1,3-benzoxazol-6-yl)-N-cyclopropylimidazo[1,2-b]pyridazine-2-carboxamide |
| 89 | 829 | 333 | 3760 | >17200 | N-cyclopropyl-3-(7-methyl[1,2,4]triazolo[1,5-a]pyridin-6-yl)imidazo[1,2-b]pyridazine-2-carboxamide |
| 90 | 21.4 | 43.7 | 25.5 | 2620 | 3-(4-cyano-3-fluorophenyl)-N-cyclopropylimidazo[1,2-b]pyridazine-2-carboxamide |
| 91 | 12.6 | 36.9 | 80.0 | 2250 | azetidin-1-yl[3-(4-chloro-2,5-difluorophenyl)imidazo[1,2-b]pyridazin-2-yl]methanone |
| 92 | 5.52 | 21.0 | 42.5 | >1440 | 3-(4-cyano-2,5-difluorophenyl)-N-cyclopropylimidazo[1,2-b]pyridazine-2-carboxamide |
| 93 | 62.9 | 276 | 134 | 4110 | 3-(4-chloro-2,5-difluorophenyl)-N-methylimidazo[1,2-b]pyridazine-2-carboxamide |
| 94 | 24.9 | 253 | 65.0 | 5380 | 3-(4-chloro-3-fluorophenyl)-N-methylimidazo[1,2-b]pyridazine-2-carboxamide |
| 95 | ND | 306 | ND | 14800 | 3-(4-chloro-2-methylphenyl)-N-ethylimidazo[1,2-b]pyridazine-2-carboxamide |
| 96 | 4.58 | 33.2 | 29.2 | 908 | 3-(4-chloro-2,5-difluorophenyl)-N-ethylimidazo[1,2-b]pyridazine-2-carboxamide |
| 97 | 5.48 | 23.3 | 20.0 | >1850 | 3-(4-chloro-5-fluoro-2-methylphenyl)-N-(propan-2-yl)imidazo[1,2-b]pyridazine-2-carboxamide |
| 98 | 26.6 | 62.7 | 107 | 3320 | 3-(4-cyano-5-fluoro-2-methylphenyl)-N-ethylimidazo[1,2-b]pyridazine-2-carboxamide |
| 99 | 19.8 | 36.2 | 138 | 1550 | 3-(4-cyano-5-fluoro-2-methylphenyl)-N- |

TABLE 3-continued

Biological data for Examples 1-104.

| Example Number | Human PDE4A FL; IC$_{50}$ (nM)[b] | Human PDE4B FL; IC$_{50}$ (nM)[b] | Human PDE4C FL; IC$_{50}$ (nM)[b] | Human PDE4D FL; IC$_{50}$ (nM)[b] | IUPAC Name |
|---|---|---|---|---|---|
| 100 | ND | 49.1 | ND | 766 | 3-(4-chloro-2,5-difluorophenyl)-N-(propan-2-yl)imidazo[1,2-b]pyridazine-2-carboxamide |
| 101 | 268[a] | 861 | 1179[a] | >25900 | 3-(4-chlorophenyl)-N-(pyrimidin-2-yl)imidazo[1,2-b]pyridazine-2-carboxamide |
| 102 | 59.9 | 103 | 76.0 | 5010 | 3-(4-chlorophenyl)-N-(cyclopropylmethyl)imidazo[1,2-b]pyridazine-2-carboxamide |
| 103 | 62.7 | 249 | 203 | 1550 | 3-(4-chlorophenyl)-N-(1H-pyrazol-5-yl)imidazo[1,2-b]pyridazine-2-carboxamide |
| 104 | <0.488 | 1.59 | 4.69 | 145 | 3-(4-chloro-3,5-difluorophenyl)-N-cyclopropylimidazo[1,2-b]pyridazine-2-carboxamide |

[a]Values represents 1 determination
[b]Values represent the geometric mean of 2-9 determinations, unless otherwise indicated.
[c]Value represents the geometric mean of ≥ 10 determinations
ND. Value not determined

What is claimed:

1. A method of treating a patient suffering from a disease or condition mediated by PDE4 isozymes, comprising administering a therapeutically effective amount of a compound, or a pharmaceutical composition comprising said compound and a pharmaceutically acceptable excipient, wherein the compound has a structure of Formula I:

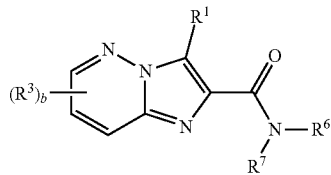

or a pharmaceutically acceptable salt thereof, wherein:
$R^1$ is selected from the group consisting of —(CH$_2$)$_m$—(C$_3$-C$_8$)cycloalkyl, —(CH$_2$)$_m$-(4- to 10-membered)heterocycloalkyl, —(CH$_2$)$_m$—(C$_6$-C$_{10}$)aryl and —(CH$_2$)$_m$-(5- to 14-membered)heteroaryl, and, where chemically permissible, the (C$_3$-C$_8$)cycloalkyl, (4- to 10-membered)heterocycloalkyl, (C$_6$-C$_{10}$)aryl and (5- to 14-membered)heteroaryl moieties are optionally substituted with one to five $R^2$;
when present, each $R^2$ is independently selected from the group consisting of halogen, oxo, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, —N(R$^4$)(R$^5$), —N(R$^4$)(C=(O)R$^5$), —C(=O)N(R$^4$)(R$^5$), —C(=O)—O—N(R$^4$)(R$^5$), —C(=O)—R$^4$, —C(=O)—OR$^4$, and optionally substituted (C$_3$-C$_8$)cycloalkyl;
when present, each $R^3$ is independently selected from the group consisting of halogen, cyano, hydroxy, —SF$_5$, nitro, optionally substituted (C$_1$-C$_6$)alkyl, optionally substituted (C$_2$-C$_6$)alkenyl, optionally substituted (C$_2$-C$_6$)alkynyl, optionally substituted (C$_1$-C$_6$)alkylthio, optionally substituted (C$_1$-C$_6$)alkoxy, —N(R$^4$)(R$^5$), —N(R$^4$)(C=(O)R$^5$), —C(=O)N(R$^4$)(R$^5$), —C(=O)—O—N(R$^4$)(R$^5$), —C(=O)—R$^4$, and —C(=O)—OR$^4$;
$R^4$ and $R^5$ are each independently selected from the group consisting of hydrogen and optionally substituted (C$_1$-C$_6$)alkyl;
$R^6$ and $R^7$ are each independently selected from the group consisting of hydrogen, optionally substituted (C$_1$-C$_6$)alkyl, —(CH$_2$)$_n$—(C$_3$-C$_8$)cycloalkyl, —(CH$_2$)$_n$-(4- to 10-membered) heterocycloalkyl, —(CH$_2$)$_n$—(C$_6$-C$_{10}$)aryl, and —(CH$_2$)$_n$-(5- to 10-membered)heteroaryl, and where chemically permissible, the (C$_3$-C$_8$)cycloalkyl, (4- to 10-membered)heterocycloalkyl, (C$_6$-C$_{10}$)aryl, and (5- to 10-membered)heteroaryl are optionally substituted with one to five $R^8$; or
$R^6$ and $R^7$ taken together with the nitrogen to which they are attached form a (4- to 10-membered)heterocycloalkyl, and where chemically permissible, the (4- to 10-membered)-heterocycloalkyl is optionally substituted with one to five $R^9$;

when present, each $R^8$ is independently selected from the group consisting of halogen, oxo, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$) alkylthio, optionally substituted ($C_1$-$C_6$)alkoxy, —$N(R^4)(R^5)$, —$N(R^4)(C$=$(O)R^5)$, —$C($=$O)N(R^4)(R^5)$, —$C($=$O)$—$O$—$N(R^4)(R^5)$, —$C($=$O)$—$R^4$, and —$C($=$O)$—$OR^4$;

when present, each $R^9$ is independently selected from the group consisting of halogen, oxo, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$) alkylthio, optionally substituted ($C_1$-$C_6$)alkoxy, —$N(R^4)(R^5)$, —$N(R^4)(C$=$(O)R^5)$, —$C($=$O)N(R^4)(R^5)$, —$C($=$O)$—$O$—$N(R^4)(R^5)$, —$C($=$O)$—$R^4$, and —$C($=$O)$—$OR^4$;

b is represented by an integer selected from 0, 1, 2, or 3;
m is represented by an integer selected from 0, 1, or 2; and
n is represented by an integer selected from 0, 1, 2, 3 or 4, wherein the disease or condition is selected from schizophrenia, depression, anxiety, Alzheimer's disease, psychosis, Parkinson's disease, multiple sclerosis, chronic obstructive pulmonary disease, inflammation, stroke, asthma, psoriatic arthritis, autoimmune diseases, allergic rhinitis, and behavioral disorders due to the use of alcohol, opioids, cannabinoids, sedatives, hypnotics or cocaine.

2. The method according to claim 1, wherein in the compound of Formula I or pharmaceutically acceptable salt thereof, m is 0 and $R^1$ is a (4- to 10-membered)heterocycloalkyl optionally substituted with one to three $R^2$, wherein the optionally substituted heterocycloalkyl is selected from the group consisting of azetidinyl, dihydrofuranyl, dihydrothiophenyl, tetrahydrothiophenyl, tetrahydrofuranyl, tetrahydrotriazinyl, tetrahydropyrazolyl, tetrahydrooxazinyl, tetrahydropyrimidinyl, octahydrobenzofuranyl, octahydrobenzimidazolyl, octaohydrobenzothiazolyl, imidazolidinyl, pyrrolidinyl, piperidinyl, piperazinyl, oxazolidinyl, isothiazolidinyl, thiazolidinyl, pyrazolidinyl, thiomorpholinyl, tetrahydropyranyl, tetrahydrothiazinyl, tetrahydrothiadiazinyl, tetrahydrooxazolyl, morpholinyl, oxetanyl, tetrahydrodiazinyl, oxazinyl, oxathiazinyl, quinuclidinyl, chromanyl, isochromanyl, dihydrobenzodioxinyl, benzodioxolyl, benzoxazinyl, indolinyl, dihydrobenzofuranyl, tetrahydroquinolyl, isochromyl, dihydro-1H-isoindolyl, 2-azabicyclo[2.2.1]heptanonyl, 3-azabicyclo[3.1.0]hexanyl, and 3-azabicyclo[4.1.0]heptanyl.

3. The method according to claim 1, wherein in the compound of Formula I or pharmaceutically acceptable salt thereof, m is 0 and $R^1$ is a ($C_6$-$C_{10}$)aryl optionally substituted with one to three $R^2$, wherein the optionally substituted ($C_6$-$C_{10}$)aryl is phenyl or naphthyl.

4. The method according to claim 3, wherein in the compound of Formula I or pharmaceutically acceptable salt thereof, the $R^1$ optionally substituted ($C_6$-$C_{10}$)aryl is phenyl.

5. The method according to claim 1, wherein in the compound of Formula I or pharmaceutically acceptable salt thereof, m is 0 and $R^1$ is a (5- to 14-membered)heteroaryl optionally substituted with one to three $R^2$, wherein the optionally substituted (5- to 14-membered)heteroaryl is selected from the group consisting of triazolyl, imidazolyl, furanyl, isoxazolyl, isothiazolyl, 1,2,3-, 1,2,4, 1,2,5-, or 1,3,4-oxadiazolyl, oxazolyl, thiophenyl, thiazolyl, isothiazolyl, pyrazolyl, pyridinyl, pyrazinyl, pyrimidinyl, pyridazinyl, indolyl, indazolyl, benzofuranyl, benzimidazolyl, benzothienyl, benzoxadiazolyl, benzothiazolyl, isobenzothiofuranyl, benzothiofuranyl, benzisoxazolyl, benzoxazolyl, benzodioxolyl, furanopyridinyl, purinyl, imidazopyridinyl, imidazopyrimidinyl, pyrrolopyridinyl, pyrazolopyridinyl, pyrazolopyrimidinyl, thienopyridinyl, triazolopyrimidinyl, triazolopyridinyl, quinolinyl, isoquinolinyl, cinnolinyl, quinazolinyl, oxochromenyl, and 1,4-benzoxazinyl.

6. The method according to claim 5, wherein in the compound of Formula I or pharmaceutically acceptable salt thereof, the $R^1$ heteroaryl is a (5- to 10-membered)nitrogen-containing heteroaryl selected from the group consisting of triazolyl, imidazolyl, pyrazolyl pyridinyl, pyrazinyl, pyrimidinyl, pyridazinyl, triazolopyridinyl, pyrazolopyridinyl, pyrazolopyrimidinyl, or quinoxalinyl.

7. The method according to claim 6, wherein in the compound of Formula I or pharmaceutically acceptable salt thereof, the $R^1$ heteroaryl is selected from:
i) a (5-membered)nitrogen-containing heteroaryl; or
ii) a (6-membered)nitrogen-containing heteroaryl.

8. The method according to claim 1, wherein in the compound of Formula I or pharmaceutically acceptable salt thereof, each $R^2$ is independently selected from the group consisting of halogen, oxo, cyano, hydroxy, optionally substituted ($C_1$-$C_6$)alkyl, and optionally substituted ($C_1$-$C_6$) alkoxy.

9. The method according to claim 8, wherein in the compound of Formula I or pharmaceutically acceptable salt thereof, $R^2$ is selected from:
i) a halogen selected from fluoro or chloro;
ii) an optionally substituted ($C_1$-$C_6$)alkyl selected from methyl, ethyl or propyl, and the methyl, ethyl and propyl are optionally substituted with one to three fluorine atoms; or
iii) an optionally substituted ($C_1$-$C_6$)alkoxy selected from methoxy, ethoxy or propoxy and the methoxy, ethoxy and propoxy are optionally substituted with one to three fluorine atoms.

10. The method according to claim 1, wherein in the compound of Formula I or pharmaceutically acceptable salt thereof, $R^6$ and $R^7$ are each independently selected from the group consisting of hydrogen, optionally substituted ($C_1$-$C_6$)alkyl, —$(CH_2)_n$—($C_3$-$C_8$)cycloalkyl, —$(CH_2)_n$—($C_6$-$C_{10}$)aryl, and —$(CH_2)_n$-(5- to 6-membered)heteroaryl, and where chemically permissible, the ($C_3$-$C_8$)cycloalkyl, ($C_6$-$C_{10}$)aryl, and (5- to 6-membered)heteroaryl are optionally substituted with one to three $R^8$; or $R^6$ and $R^7$ taken together with the nitrogen to which they are attached form a (4- to 6-membered)heterocycloalkyl, and where chemically permissible, the (4- to 6-membered)-heterocycloalkyl is optionally substituted with one to three $R^9$;

when present each $R^8$ is independently selected from the group consisting of halogen, oxo, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$) alkylthio, optionally substituted ($C_1$-$C_6$)alkoxy, —$N(R^4)(R^5)$, —$N(R^4)(C$=$(O)R^5)$, —$C($=$O)N(R^4)(R^5)$, —$C($=$O)$—$O$—$N(R^4)(R^5)$, —$C($=$O)$—$R^4$, and —$C($=$O)$—$OR^4$; and when present each $R^9$ is independently selected from the group consisting of halogen, oxo, cyano, hydroxy, —$SF_5$, nitro, optionally substituted ($C_1$-$C_6$)alkyl, optionally substituted ($C_2$-$C_6$)alkenyl, optionally substituted ($C_2$-$C_6$)alkynyl, optionally substituted ($C_1$-$C_6$)

alkylthio, optionally substituted (C₁-C₆)alkoxy, —N(R⁴)(R⁵), —N(R⁴)(C(=O)R⁵), —C(=O)N(R⁴)(R⁵), —C(=O)—O—N(R⁴)(R⁵), —C(=O)—R⁴, and —C(=O)—OR⁴.

11. The method according to claim 10, wherein in the compound of Formula I or pharmaceutically acceptable salt thereof, one of R⁶ and R⁷ is hydrogen and the other is an optionally substituted (C₁-C₆)alkyl selected from the group consisting of methyl, ethyl, propyl, isopropyl, butyl, tert-butyl, pentyl and hexyl, and the methyl, ethyl, propyl, isopropyl, butyl, tert-butyl, pentyl and hexyl is optionally substituted with one or more fluorine atoms.

12. The method according to claim 10, wherein in the compound of Formula I or pharmaceutically acceptable salt thereof, one of R⁶ and R⁷ is hydrogen and the other is —(CH₂)ₙ—(C₃-C₈)cycloalkyl selected from cyclopropyl, cyclobutyl, cyclopentyl, cyclohexyl, cyclooctyl or bicyclo[1.1.1]pentyl, wherein the cycloalkyl is optionally substituted with one to three R⁸.

13. The method according to claim 10, wherein in the compound of Formula I or pharmaceutically acceptable salt thereof, one of R⁶ and R⁷ is hydrogen and the other is —(CH₂)ₙ—(C₆-C₁₀)aryl, wherein the aryl is optionally substituted with one to three R⁸.

14. The method according to claim 10, wherein in the compound of Formula I or pharmaceutically acceptable salt thereof, one of R⁶ and R⁷ is hydrogen and the other is —(CH₂)ₙ-(5- to 6-membered)heteroaryl selected from triazolyl, imidazolyl, furanyl, isoxazolyl, isothiazolyl, 1,2,3-, 1,2,4, 1,2,5-, or 1,3,4-oxadiazolyl, oxazolyl, thiophenyl, thiazolyl, isothiazolyl, pyrazolyl, pyridinyl, pyrazinyl, pyrimidinyl, or pyridazinyl, wherein the heteroaryl is optionally substituted with one to three R⁸.

15. The method according to claim 10, wherein in the compound of Formula I, each R⁸ is independently selected from the group consisting of halogen, oxo, cyano, hydroxy, or pharmaceutically acceptable salt thereof, optionally substituted (C₁-C₆)alkyl, and optionally substituted (C₁-C₆)alkoxy.

16. The method according to claim 10, wherein in the compound of Formula I or pharmaceutically acceptable salt thereof, R⁶ and R⁷ taken together with the nitrogen to which they are attached form a (4- to 6-membered)heterocycloalkyl optionally substituted with one to three R⁹, wherein the heterocycloalkyl is selected from azetidinyl, tetrahydropyrazolyl, tetrahydrooxazinyl, tetrahydropyrimidinyl, imidazolidinyl, piperidinyl, piperazinyl, oxazolidinyl, or pyrrolidinyl.

17. The method according to claim 16, wherein in the compound of Formula I or pharmaceutically acceptable salt thereof, the heterocycloalkyl that is formed by R⁶ and R⁷ is azetidinyl.

18. The method according to claim 16, wherein in the compound of Formula I or pharmaceutically acceptable salt thereof, each R⁹ is independently selected from the group consisting of halogen, oxo, cyano, hydroxy, optionally substituted (C₁-C₆)alkyl, and optionally substituted (C₁-C₆)alkoxy.

19. The method according to claim 1, wherein in the compound of Formula I or pharmaceutically acceptable salt thereof, b is an integer selected from 0, 1 or 2 and, when present, each R³ is independently selected from the group consisting of halogen, cyano, hydroxy, —SF₅, nitro, optionally substituted (C₁-C₆)alkyl, and optionally substituted (C₁-C₆)alkoxy.

20. A method of treating a patient suffering from a disease or condition associated with PDE4 isozymes, comprising administering to said patient a therapeutically effective amount of a compound, or a pharmaceutical composition comprising said compound and a pharmaceutically acceptable excipient, wherein the compound is selected from the group consisting of:

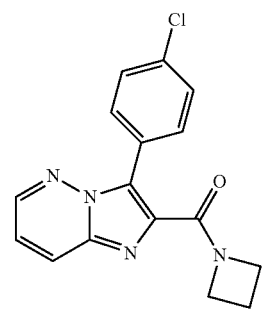

1

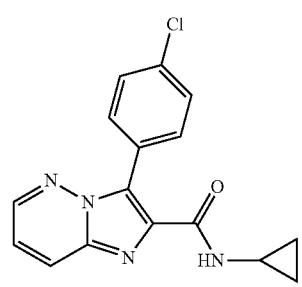

2

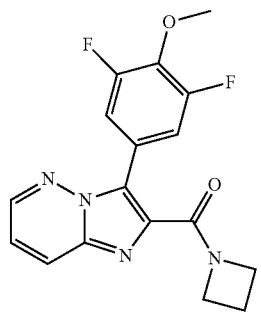

3

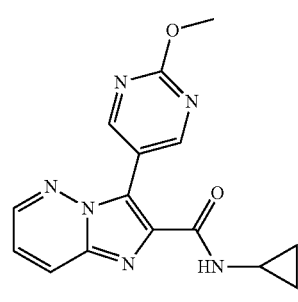

4

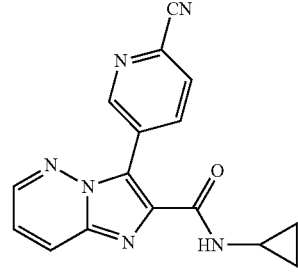

5

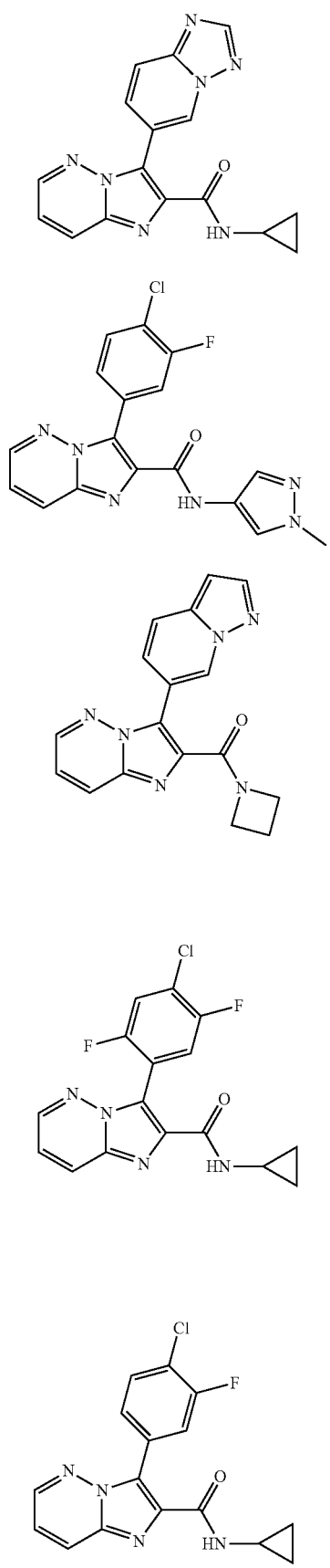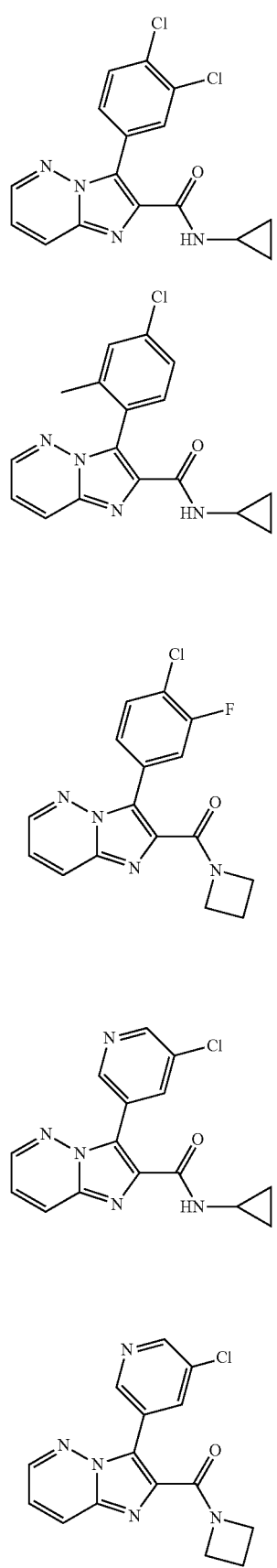

| | |
|---|---|
| 16 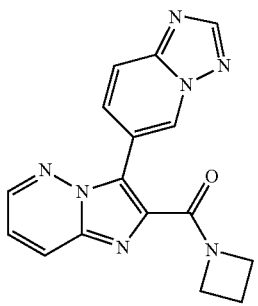 | 21 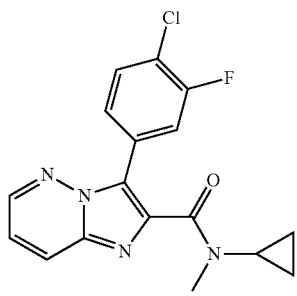 |
| 17 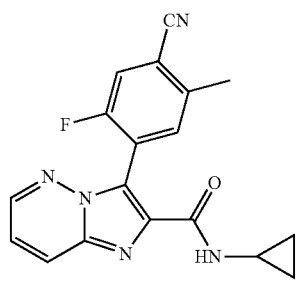 | 22 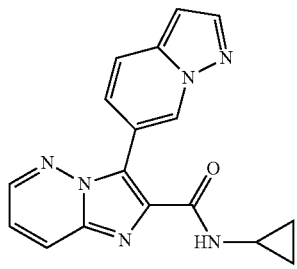 |
| 18 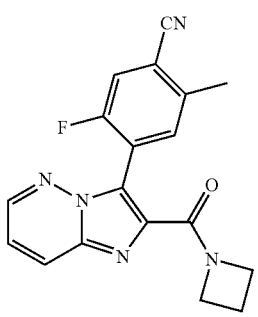 | 23 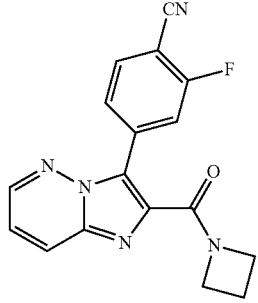 |
| 19 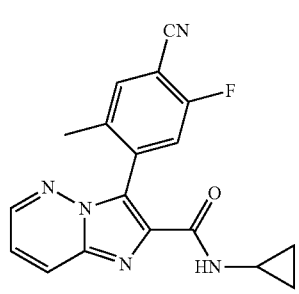 | 24 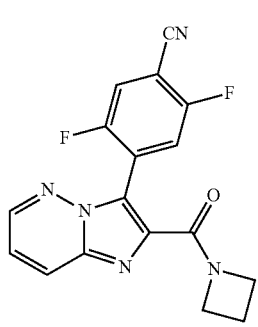 |
| 20 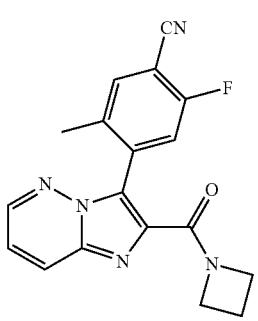 | 25 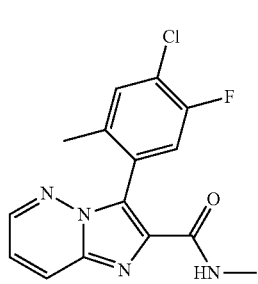 |

| | |
|---|---|
| 26 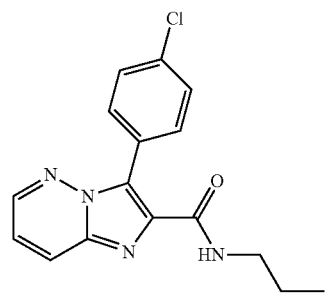 | 31 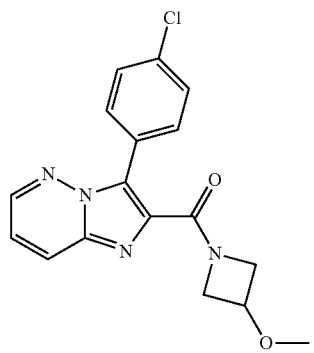 |
| 27 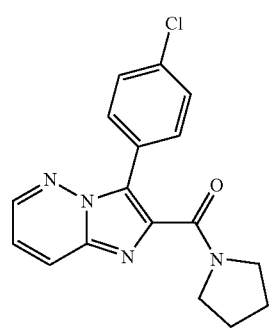 | 32 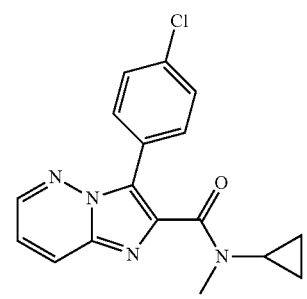 |
| 28 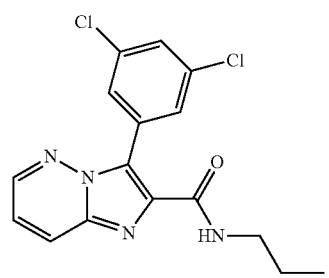 | 33 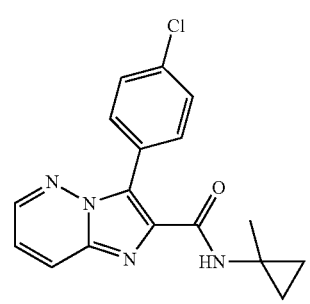 |
| 29 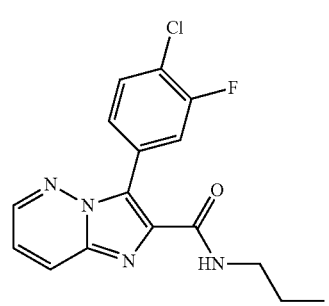 | 34 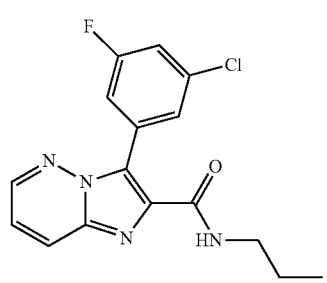 |
| 30 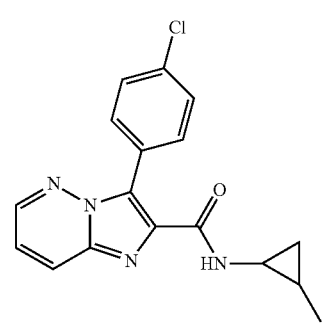 | 35 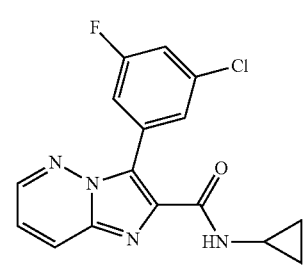 |

| 36 | 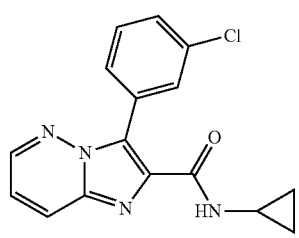 |
| 37 | 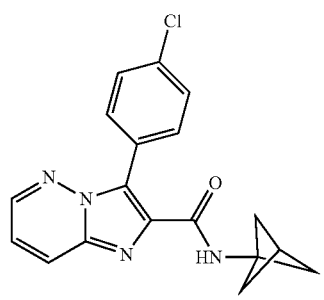 |
| 38 | 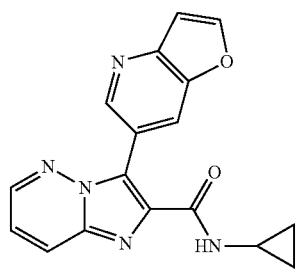 |
| 39 | 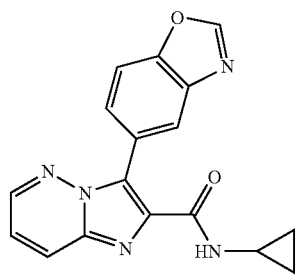 |
| 40 | 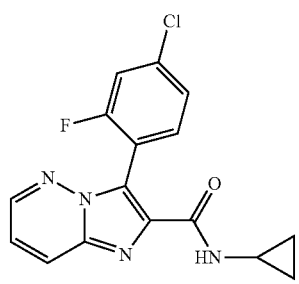 |
| 41 | 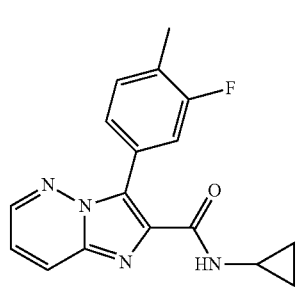 |
| 42 | 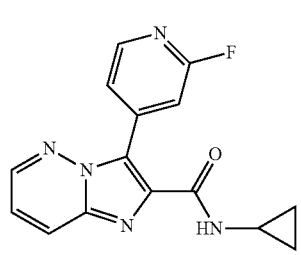 |
| 43 | 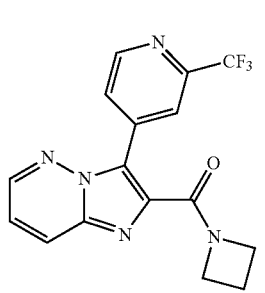 |
| 44 | 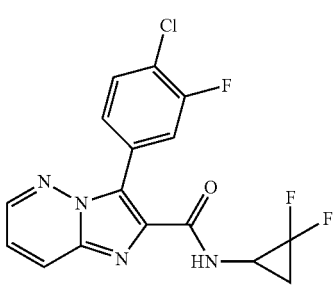 |
| 45 | 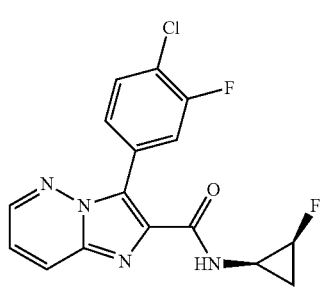 |
| 46 | 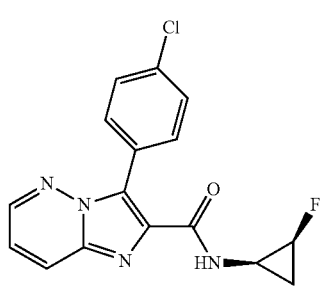 |

47
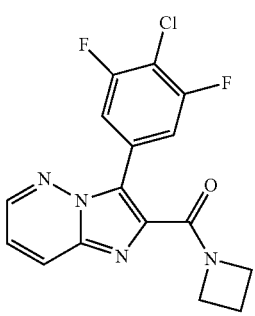
48
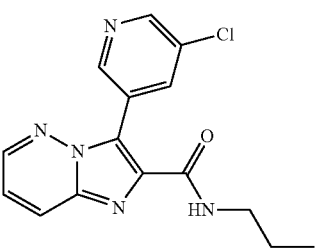
49
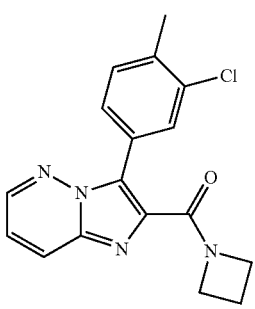
50
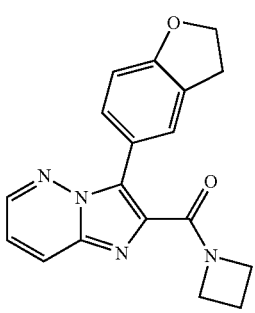
51
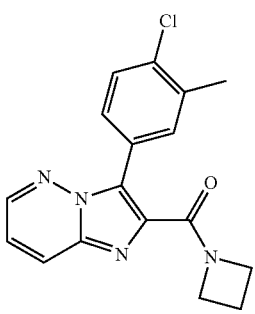
52
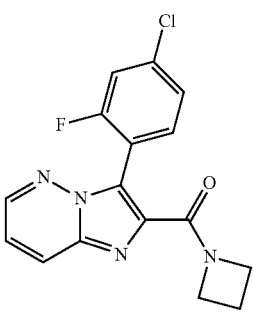
53
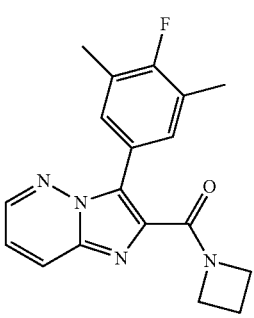
54
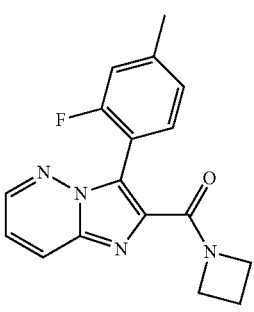
55
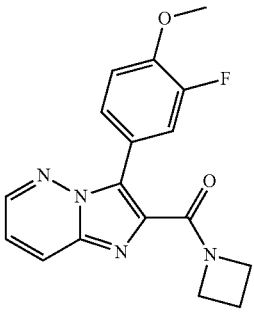
56
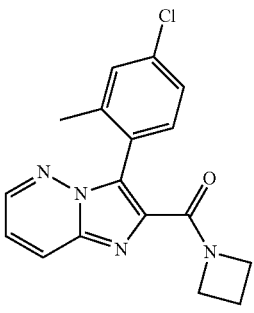

57
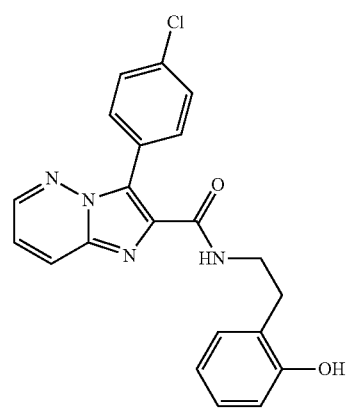
58
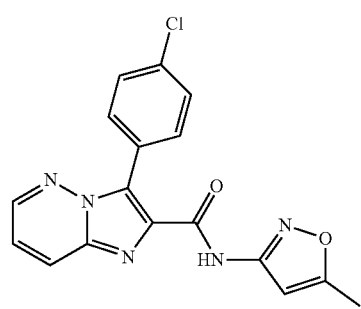
59
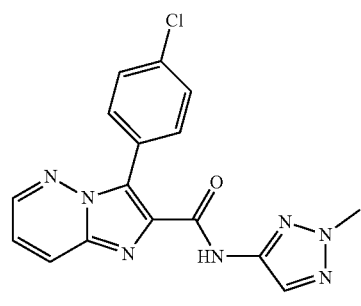
60
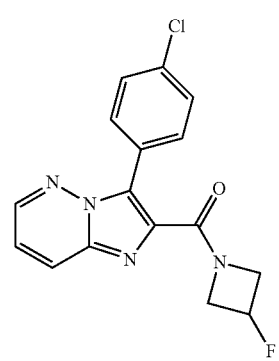
61
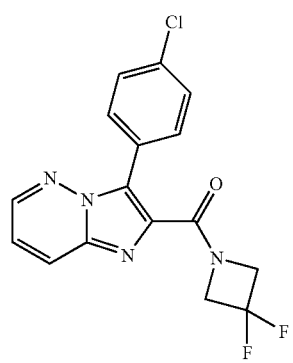
62
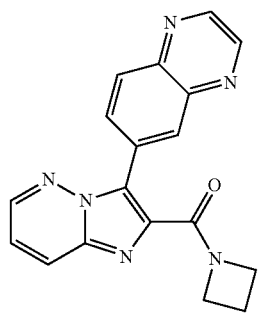
63
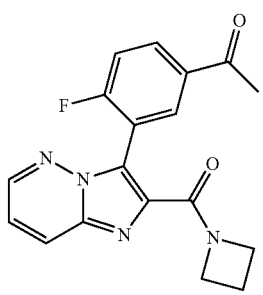
64
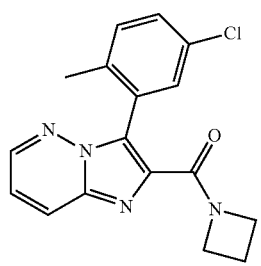
65
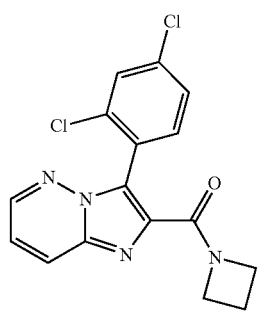

66 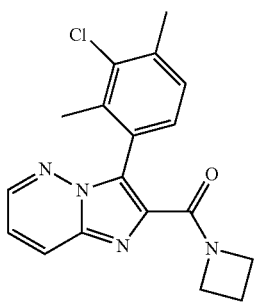
67 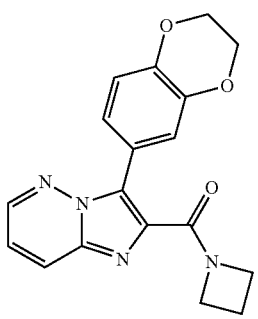
68 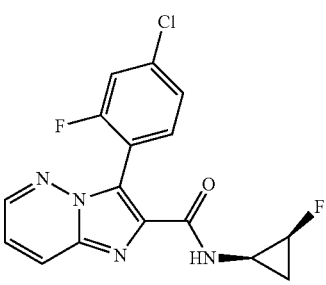
69 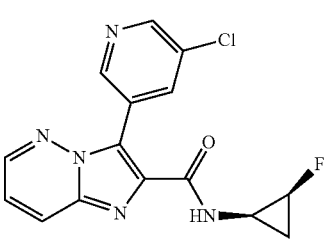
70 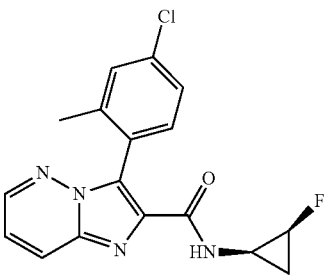
71 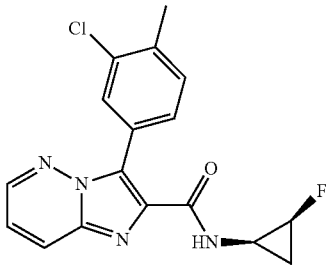
72 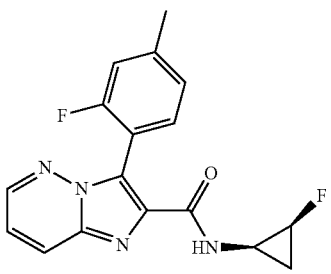
73 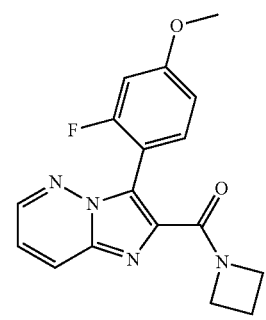
74 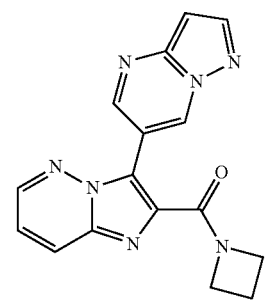
75 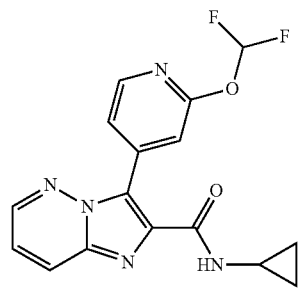

| | |
|---|---|
| 76 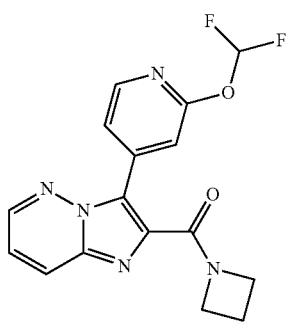 | 81 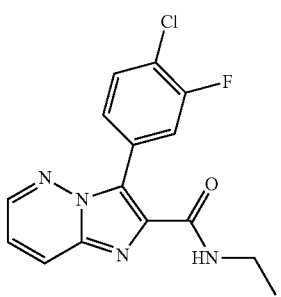 |
| 77 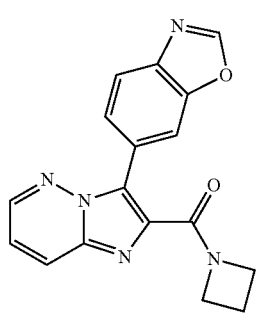 | 82 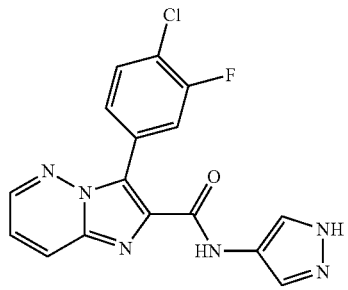 |
| 78 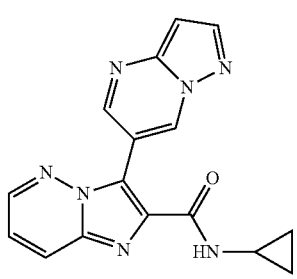 | 83 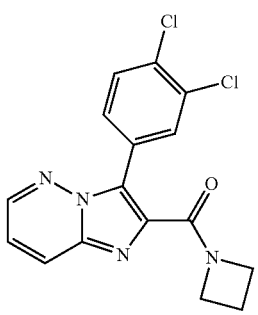 |
| 79 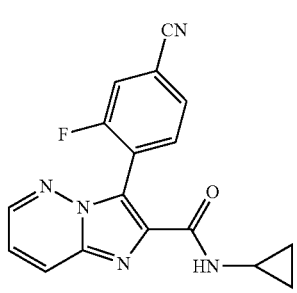 | 84 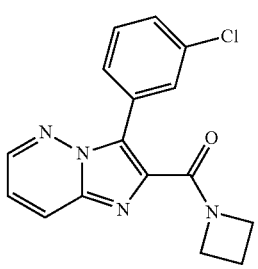 |
| 80 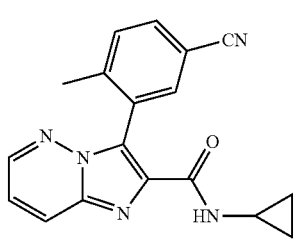 | 85 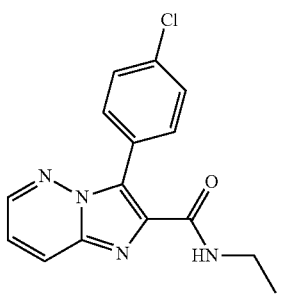 |

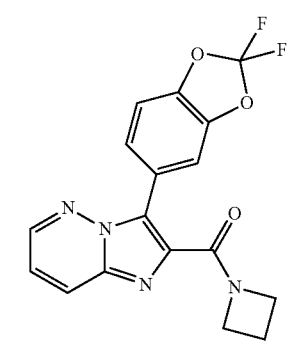
86
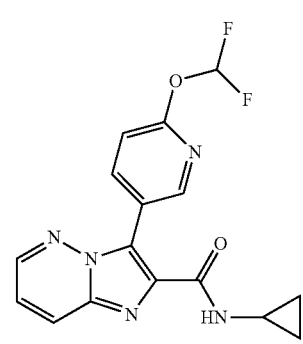
87
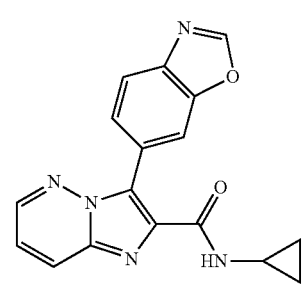
88
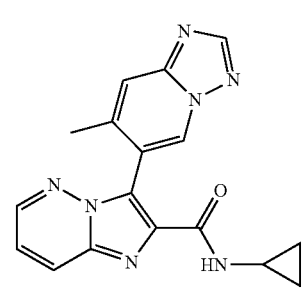
89
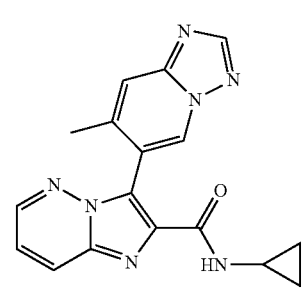
90
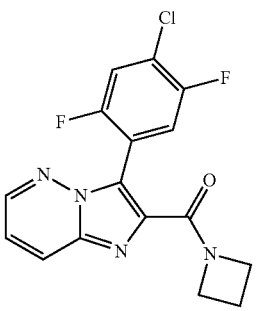
91
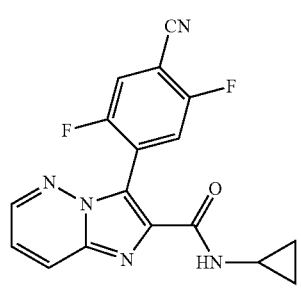
92
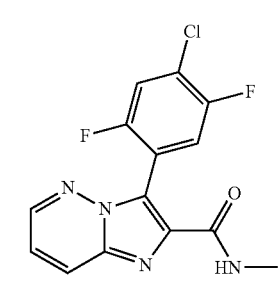
93
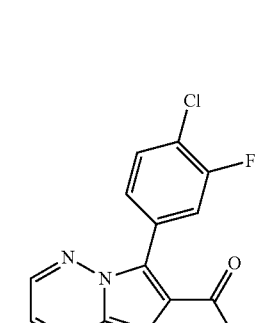
94
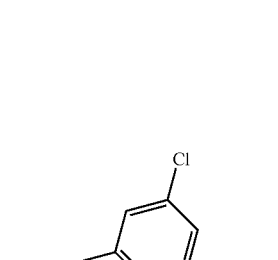
95

96 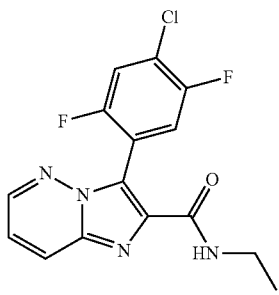

97 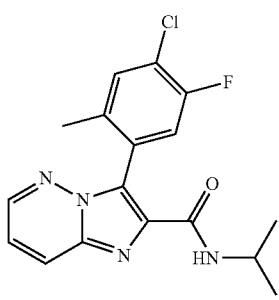

98 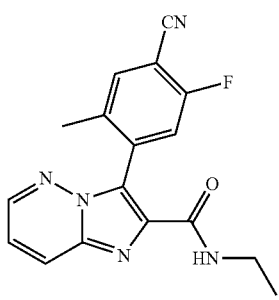

99 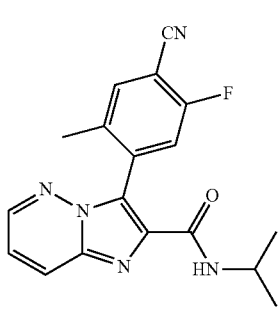

100 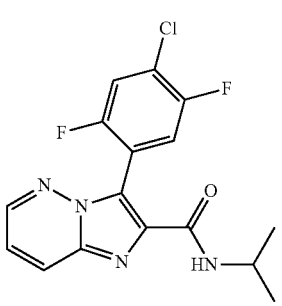

101 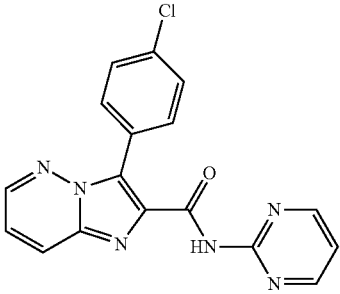

102 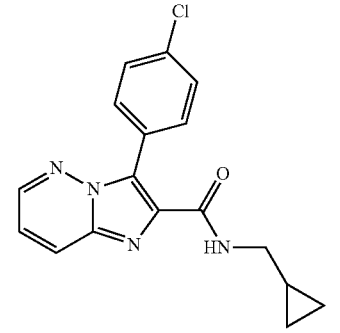

103 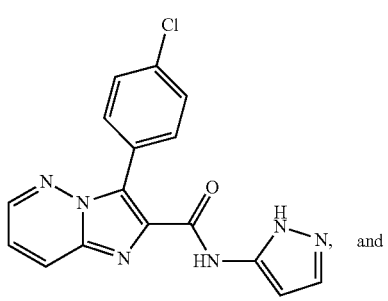

and

104 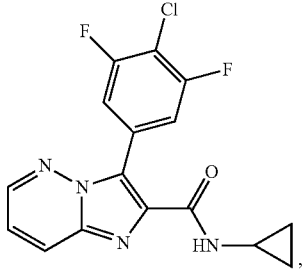

or a pharmaceutically acceptable salt thereof,
wherein the disease or condition is selected from schizophrenia, depression, anxiety, Alzheimer's disease, psychosis, Parkinson's disease, multiple sclerosis, chronic obstructive pulmonary disease, inflammation, stroke, asthma, psoriatic arthritis, autoimmune diseases, allergic rhinitis, and behavioral disorders due to the use of alcohol, opioids, cannabinoids, sedatives, hypnotics or cocaine.

21. A method of treating a patient suffering from a disease or condition associated with PDE4 isozymes, comprising administering to said patient a therapeutically effective amount of a compound, or a pharmaceutical composition comprising said compound and a pharmaceutically acceptable excipient, wherein the compound has the structure,

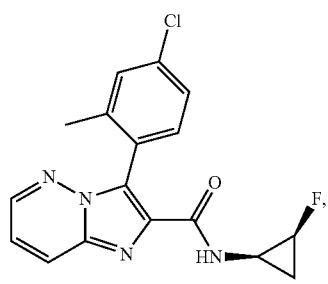 [SMILES: Cc1cc(Cl)ccc1-c1c(C(=O)N[C@@H]2C[C@@H]2F)nc2cccnn12]

or a pharmaceutically acceptable salt thereof,
  wherein the disease or condition is selected from schizophrenia, depression, anxiety, Alzheimer's disease, psychosis, Parkinson's disease, multiple sclerosis, chronic obstructive pulmonary disease, inflammation, stroke, asthma, psoriatic arthritis, autoimmune diseases, allergic rhinitis, and behavioral disorders due to the use of alcohol, opioids, cannabinoids, sedatives, hypnotics or cocaine.

22. A method of treating a patient suffering from a disease or condition associated with PDE4 isozymes, comprising administering to said patient a therapeutically effective amount of a compound, or a pharmaceutical composition comprising said compound and a pharmaceutically acceptable excipient, wherein the compound has the structure,

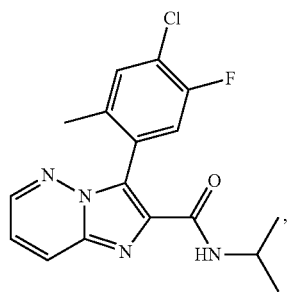 [SMILES: Cc1cc(Cl)c(F)cc1-c1c(C(=O)NC(C)C)nc2cccnn12]

or a pharmaceutically acceptable salt thereof,
  wherein the disease or condition is selected from schizophrenia, depression, anxiety, Alzheimer's disease, psychosis, Parkinson's disease, multiple sclerosis, chronic obstructive pulmonary disease, inflammation, stroke, asthma, psoriatic arthritis, autoimmune diseases, allergic rhinitis, and behavioral disorders due to the use of alcohol, opioids, cannabinoids, sedatives, hypnotics or cocaine.

* * * * *

UNITED STATES PATENT AND TRADEMARK OFFICE
CERTIFICATE OF CORRECTION

PATENT NO. : 10,669,279 B2  
APPLICATION NO. : 16/455020  
DATED : June 2, 2020  
INVENTOR(S) : Thomas Allen Chappie et al.

Page 1 of 1

It is certified that error appears in the above-identified patent and that said Letters Patent is hereby corrected as shown below:

In the Claims

In Claim 20, Column 108, Line 10, replace 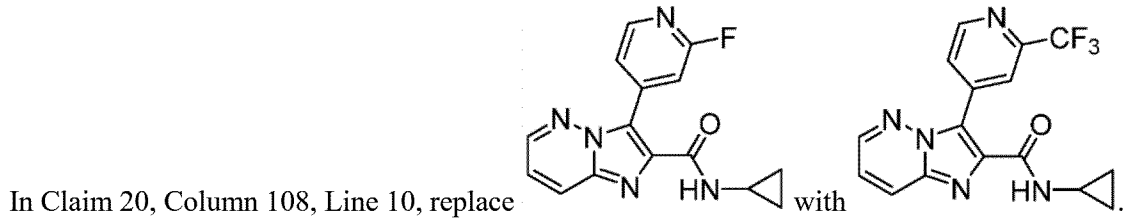.

In Claim 20, Column 114, Line 50, replace .

Signed and Sealed this  
Fourteenth Day of July, 2020

Andrei Iancu  
*Director of the United States Patent and Trademark Office*